US012807583B2

(12) United States Patent
Keillor et al.

(10) Patent No.: US 12,807,583 B2
(45) Date of Patent: Nov. 24, 2026

(54) ARYLACETYL INHIBITORS OF TG2 AND USES THEREOF

(71) Applicant: UNIVERSITY OF OTTAWA, Ottawa (CA)

(72) Inventors: Jeffrey Keillor, Ottawa (CA); Nicole McNeil, Gloucester (CA)

(73) Assignee: UNIVERSITY OF OTTAWA, Ottawa (CA)

(*) Notice: Subject to any disclaimer, the term of this patent is extended or adjusted under 35 U.S.C. 154(b) by 412 days.

(21) Appl. No.: 18/554,358

(22) PCT Filed: Apr. 7, 2022

(86) PCT No.: PCT/CA2022/050528

§ 371 (c)(1),
(2) Date: Oct. 6, 2023

(87) PCT Pub. No.: WO2022/213198

PCT Pub. Date: Oct. 13, 2022

(65) Prior Publication Data

US 2024/0383869 A1 Nov. 21, 2024

Related U.S. Application Data

(60) Provisional application No. 63/221,625, filed on Jul. 14, 2021, provisional application No. 63/172,452, filed on Apr. 8, 2021.

(51) Int. Cl.

| | |
|---|---|
| ***C07D 295/192*** | (2006.01) |
| ***A61K 31/495*** | (2006.01) |
| ***A61K 31/496*** | (2006.01) |
| ***A61P 25/28*** | (2006.01) |
| ***A61P 35/00*** | (2006.01) |
| ***C07D 213/81*** | (2006.01) |
| ***C07D 213/82*** | (2006.01) |
| ***C07D 233/90*** | (2006.01) |
| ***C07D 401/12*** | (2006.01) |

(52) U.S. Cl.

CPC ........ *C07D 295/192* (2013.01); *A61K 31/495* (2013.01); *A61K 31/496* (2013.01); *C07D 213/81* (2013.01); *C07D 213/82* (2013.01); *C07D 233/90* (2013.01)

(58) Field of Classification Search

CPC ............. C07D 295/192; C07D 213/81; C07D 213/82; C07D 233/90; C07D 401/12; A61K 31/495; A61K 31/496; A61P 25/28; A61P 35/00

See application file for complete search history.

(56) References Cited

U.S. PATENT DOCUMENTS

| | | | |
|---|---|---|---|
| 9,656,987 | B2 | 5/2017 | Griffin et al. |
| 2015/0232420 | A1 | 8/2015 | Dominguez et al. |

OTHER PUBLICATIONS

Mcneil, N. et al., Structure-activity relationships of N-terminal variants of peptidomimetic tissue transglutaminase inhibitors, European Journal of Medicinal Chemistry, Elsevier Masson, vol. 232, pp. 114172-114195, Feb. 3, 2022.

Supplementary European Search Report issued in co-pending European patent application No. 22783734.1 on Jan. 16, 2025.

International Search Report and Written opinion issued in corresponding International application No. PCT/CA2022/050528 on Aug. 1, 2022.

Wodtke et al., Ne-Acryloyllysine piperazides as irreversible inhibitors of transglutaminase 2: Synthesis, structure-activity relationships, and pharmacokinetic profiling, J. Med. Chem., 2018, vol. 61, pp. 4528-4560.

*Primary Examiner* — Brenda L Coleman

(74) *Attorney, Agent, or Firm* — BCF LLP

(57) ABSTRACT

There are provided Tissue Transglutaminase (TG2) inhibitor compounds, and compositions and methods of use thereof for the prevention or treatment of a disease state mediated by TG2, such as a cancer, a neurodegenerative disease such as Huntington's disease, fibrosis, or Celiac disease. Compounds of Formula I, and pharmaceutically acceptable salts thereof, are provided: Formula (I).

(I)

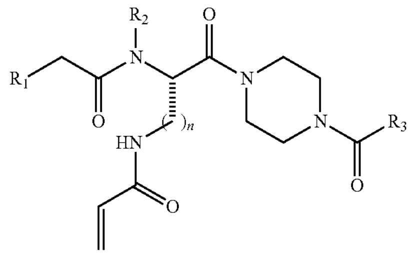

19 Claims, 7 Drawing Sheets

ARYLACETYL INHIBITORS OF TG2 AND USES THEREOF

CROSS-REFERENCE TO RELATED APPLICATIONS

This application is a national stage entry under 35 U.S.C. § 371 of PCT/CA2022/050528, filed Apr. 7, 2022, which claims the benefit of priority from U.S. Provisional Patent Application No. 63/172,452, filed Apr. 8, 2021, and from U.S. Provisional Patent Application No. 63/221,625, filed Jul. 14, 2021, each of which are hereby incorporated by reference in their entirety.

FIELD

The present disclosure relates to arylacetyl inhibitors of Tissue Transglutaminase 2 (TG2), and compositions and methods of use thereof for treating diseases mediated by TG2.

BACKGROUND

Tissue transglutaminase 2 (TG2) is a multifunctional protein that plays a role in many different cellular processes including differentiation, neuronal growth, inflammation, development and wound healing. TG2 is the most frequently occurring transglutaminase in eukaryotes and is present in almost all mammalian cells. TG2 can act as a scaffold or linker protein to mediate protein-protein interactions both extracellularly and intracellularly. TG2 is known to catalyze protein cross-linking in the extracellular matrix (ECM) and to participate in GTP-binding inside the cell.

In addition to catalyzing calcium-dependent transamidation reactions, TG2 binds and hydrolyzes GTP, and GTP binding inhibits the transamidation activity. Under normal physiological conditions, due to low calcium levels and high GTP levels, intracellular TG2 is likely a latent enzyme with respect to transamidation activity. However, in pathological conditions with high intracellular calcium and decreased GTP reserves, increases in TG2 transamidation activity likely occur. A significant outcome of calcium binding is that concurrent with activation, TG2 undergoes an extraordinary conformational change that results in an extended structure. In contrast, in the GTP bound state, TG2 exists in a compact and closed structure that decreases the accessibility of the active site. Therefore, calcium binding and GTP binding inversely regulate the conformational state of TG2, as well as the transamidation activity.

TG2 has been implicated in a wide range of physiological and pathophysiological conditions, including fibrotic and neoplastic processes, neurodegenerative diseases such as Huntington's disease, and gluten sensitivity diseases such as Celiac disease. Consequently, TG2 is considered a promising therapeutic target for such diseases. Recent studies have shown that TG2 likely plays a significant role in tumor cell biology. For example, TG2 expression has been correlated with various types of malignancies, including glioblastomas, lung and breast cancers, suggesting an important role for TG2 in tumor proliferation and survival. TG2 is markedly overexpressed in some cancer cells and has been implicated in maintaining and enhancing EMT in breast and ovarian cancer. Two different TG2 inhibitors (monodansylcadaverine (MDC), a non-specific competitive inhibitor, and the active site directed inhibitor, Z-DON) have been shown to reduce proliferation in two out of three glioblastoma multiforme (GBM) cell lines tested (Zhang, J. et al., Cell Reports 3(6): 2008-2020, 2013). TG2 has also been implicated in epidermal cancer stem (ECS) cell survival and EMT regulation. It has been shown that TG2 expression is upregulated in drug resistant cells and that TG2 inhibitors may increase sensitivity of certain GBM cells to chemotherapy. TG2 is thus a promising target for addressing cancer recurrence, metastasis, and chemoresistance.

Despite intensive research, cancer remains one of the leading causes of mortality in North America, with metastasis and drug resistance accounting for the majority of cancer related deaths. Recent evidence has suggested a few reasons for the ineffectiveness of some chemotherapeutic approaches: 1) An increasing body of evidence has demonstrated the existence of cancer stem cells (CSCs) in many of the most common and most lethal tumours. CSCs have been identified in human blood cell-derived cancers as well as solid organ tumours of the colon, breast, lung, prostate, brain, pancreas and skin. These stem cells may not be removed by excision of the tumour, and fewer than 100 CSCs are capable of regenerating a tumour. 2) Some tumour cells can undergo epithelial to mesenchymal transition (EMT), taking on the properties of stem cells and initiating metastasis. 3) Most anti-cancer drugs target the rapidly dividing cells of epithelial tumours. However, CSCs and cells undergoing EMT proliferate slowly, and alternative pathways for inducing EMT have been discovered, such that these refractory cancer cells are resistant to most chemotherapeutic agents. Drug resistance has also been linked to cells undergoing EMT, particularly for drugs that target cell growth pathways, such as doxorubicin and the most common chemotherapeutics. Novel approaches for anti-cancer therapies are therefore needed, particularly to target CSCs and cells undergoing EMT, both of which have proven refractory to current inhibitors.

Wityak et al. describes a series of irreversible transglutaminase 2 inhibitors starting from a known lysine dipeptide bearing an acrylamide warhead (Wityak, J. et al., "SAR development of lysine-based irreversible inhibitors of Transglutaminase 2 for Huntington's Disease." *ACS Med. Chem. Lett.* 2012 (3), 1024-1028). Wityak et al. established new structure-activity relationships (SARs) resulting in compounds demonstrating improved potency and better physical and calculated properties. Transglutaminase selectivity profiling and in vitro ADME properties of selected compounds were also reported.

International PCT Application Publication No. WO 2014/047288 teaches transglutaminase TG2 inhibitors, pharmaceutical compositions, and methods of use thereof for treating patients suffering from certain disease states responsive to the inhibition of transglutaminase TG2 activity. These disease states include neurodegenerative disorders such as Huntington's disease and gluten sensitivity disease such as Celiac disease, although the described TG2 inhibitor compounds are shown to possess a high P-glycoprotein efflux rate and therefore be unsuitable candidates for treatments of disease where BBB permeability is desired. Methods of treatment including administering at least one compound or pharmaceutically acceptable salt thereof as a single active agent or administering at least one compound or pharmaceutically acceptable salt thereof in combination with one or more other therapeutic agents are also described.

Wodtke, R. et al. reports synthesis and kinetic characterization of $N^{\varepsilon}$-acryloyllysine piperazides as irreversible inhibitors of TG2 (Wodtke, R. et al., "Acryloyllysine piperazides as irreversible inhibitors of transglutaminase 2—synthesis, structure-activity relationships and pharmacokinetic profiling." *J. Med. Chem.* 2018, 61, 4528-4560).

Systematic structural modifications on 54 new compounds were performed with a major focus on fluorine-bearing substituents due to the potential of such compounds to serve as radiotracer candidates for positron emission tomography. The determined inhibitory activities ranged from 100 to 10 000 $M^{-1}$ $s^{-1}$, which resulted in comprehensive structure-activity relationships. An initial pharmacokinetic profiling of selected inhibitors was performed, including the assessment of potential membrane permeability and liver microsomal stability.

International PCT Application Publication No. WO 2017/179018 (U.S. Pat. No. 10,894,777) teaches TG2 inhibitor compounds, and compositions and methods of use thereof for the prevention or treatment of a cancer. The TG2 inhibitor compounds are covalent inhibitors that react with intracellular TG2, locking it in an open conformation and abolishing its ability to bind GTP.

There is a need for more potent TG2 inhibitors for therapeutic use.

SUMMARY

It is an object of the present invention to ameliorate at least some of the deficiencies present in the prior art. Embodiments of the present technology have been developed based on the inventors' appreciation that there is a need for improved Tissue Transglutaminase 2 (TG2) inhibitor compounds.

In a first broad aspect there are provided compounds of Formula I, or pharmaceutically acceptable salts thereof:

Formula I

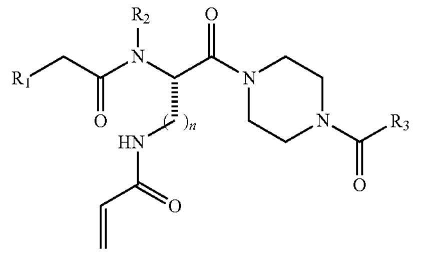

wherein:

$R_1$ is substituted or unsubstituted aryl or substituted or unsubstituted heteroaryl;

$R_2$ is hydrogen or substituted or unsubstituted $C_{1-6}$ alkyl;

$R_3$ is substituted or unsubstituted aryl or substituted or unsubstituted heteroaryl; and n is 1, 2, 3, or 4;

provided that, when $R_1$ is phenyl; $R_2$ is hydrogen; and n is 4, $R_3$ is not 4-fluorophenyl, 4-nitrophenyl or 6-chloro-2-pyridinyl.

In some embodiments of Formula I, $R_1$ is substituted or unsubstituted aryl.

In some embodiments of Formula I, $R_1$ is unsubstituted aryl.

In other embodiments of Formula I, $R_1$ is substituted aryl, e.g., substituted by hydroxyl, amino, carboxyl, sulfonate, carboxylic ester, amide, carbamate, or aminoalkyl.

In some embodiments of Formula I, $R_1$ is selected from:

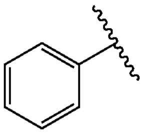,
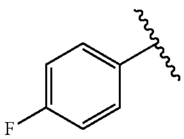,
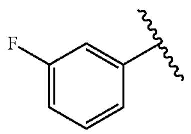,
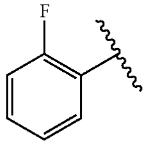,
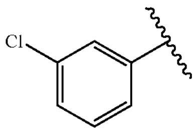,
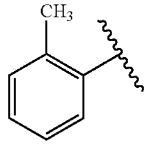,
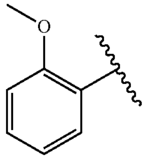,
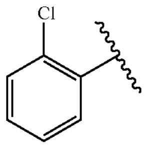,
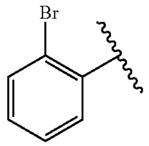,
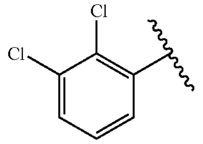,
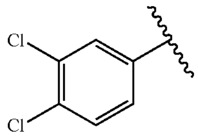, and
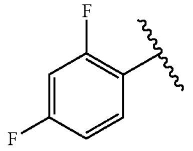.

In some embodiments of Formula I, $R_2$ is hydrogen.

In other embodiments of Formula I, $R_2$ is substituted $C_{1-6}$ alkyl, e.g., substituted methyl. In other embodiments of Formula I, $R_2$ is unsubstituted $C_{1-6}$ alkyl, e.g., unsubstituted methyl.

In some embodiments of Formula I, $R_3$ is selected from:

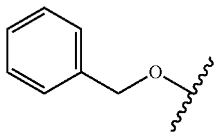,
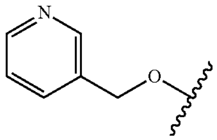,
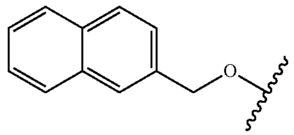,
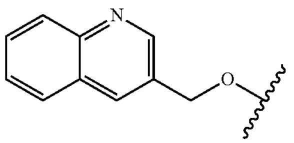,
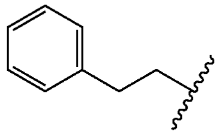,
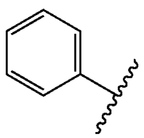,
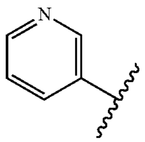,
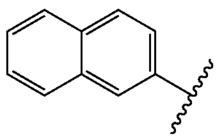, -continued

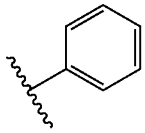,
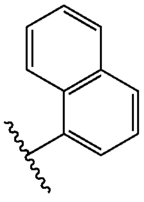,
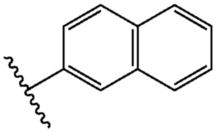,

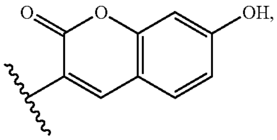

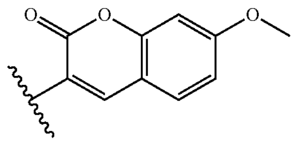, and 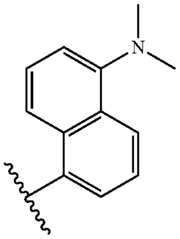.

In some embodiments of Formula I, $R_3$ is

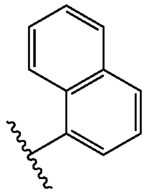.

In some embodiments of Formula I, n is 1. In some embodiments of Formula I, n is 2. In some embodiments of Formula I, n is 3. In some embodiments of Formula I, n is 4.

In some embodiments of Formula I, $R_1$ is substituted or unsubstituted aryl; $R_2$ is hydrogen; $R_3$ is

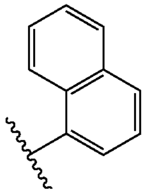;

and n is 4.

In some embodiments of Formula I, $R_1$ is unsubstituted aryl; $R_2$ is hydrogen;

$R_3$ is

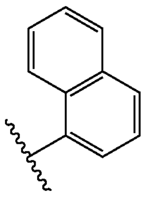;

and n is 4.

In some embodiments of Formula I, the compound is any one of compounds 67-81, or a pharmaceutically acceptable salt thereof.

In some embodiments of Formula I, the compound is compound 72 or 74, or a pharmaceutically acceptable salt thereof:

72

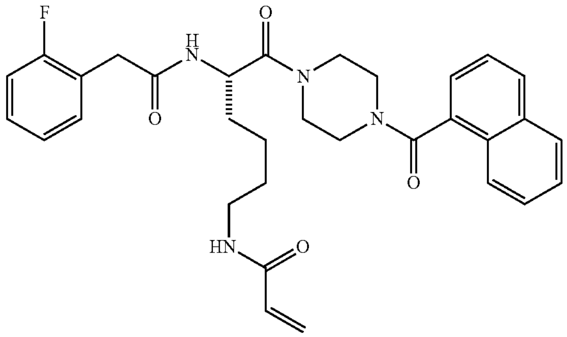

74

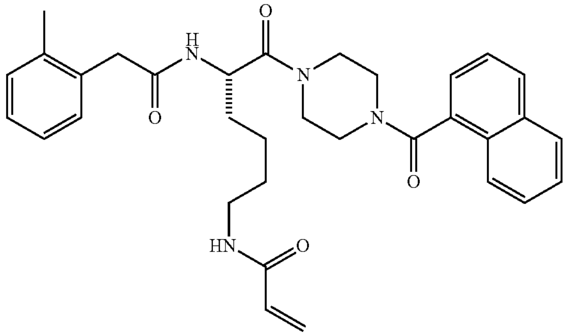

In some embodiments of Formula I, the compound is a compound shown in Table 4, or a pharmaceutically acceptable salt thereof.

In some embodiments, compounds of Formula I are TG2 inhibitor compounds. In an embodiment, compounds provided herein inhibit one or more activity of TG2, e.g., GTP binding, GTPase activity, deamidation and/or transamidation activity. In some embodiments, compounds provided herein act as conformational modulators of TG2, holding the TG2 in an open conformation that does not bind GTP, in addition to abrogating transamidation activity through covalent binding to the active site. In some embodiments, compounds provided herein are irreversible TG2 inhibitors.

In a second broad aspect there are provided compounds of Formula II, or pharmaceutically acceptable salts thereof:

Formula II

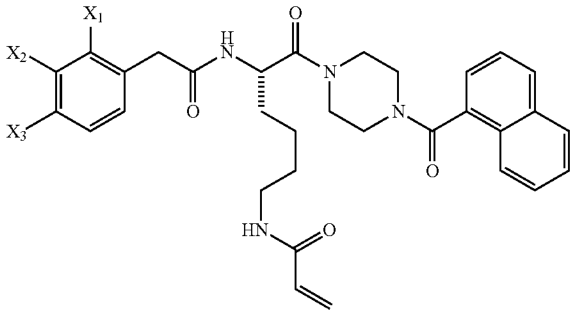

wherein:

$X_1$, $X_2$ and $X_3$ are independently selected from hydrogen, halogen, substituted or unsubstituted $C_{1-6}$ alkyl, and substituted or unsubstituted $C_{1-6}$ alkoxy.

In some embodiments of Formula II, $X_1$ is hydrogen, halogen, substituted or unsubstituted $C_{1-6}$ alkyl, or substituted or unsubstituted $C_{1-6}$ alkoxy, and $X_2$ and $X_3$ are hydrogen.

In some embodiments of Formula II, $X_2$ is hydrogen, halogen, substituted or unsubstituted $C_{1-6}$ alkyl, or substituted or unsubstituted $C_{1-6}$ alkoxy, and $X_1$ and $X_3$ are hydrogen.

In some embodiments of Formula II, $X_3$ is hydrogen, halogen, substituted or unsubstituted $C_{1-6}$ alkyl, or substituted or unsubstituted $C_{1-6}$ alkoxy, and $X_1$ and $X_2$ are hydrogen.

In some embodiments of Formula II, $X_1$ is halogen, substituted or unsubstituted $C_{1-6}$ alkyl, or substituted or unsubstituted $C_{1-6}$ alkoxy, and $X_2$ and $X_3$ are hydrogen. In some such embodiments, $X_1$ is F, Cl or Br. In some such embodiments, $X_1$ is F. In some such embodiments, $X_1$ is Me. In some such embodiments, $X_1$ is OMe.

In some embodiments of Formula II, $X_2$ is halogen, and $X_1$ and $X_3$ are hydrogen. In some such embodiments, $X_2$ is F, Cl or Br. In some such embodiments, $X_2$ is F. In some such embodiments, $X_2$ is Cl.

In some embodiments of Formula II, $X_3$ is halogen, and $X_1$ and $X_2$ are hydrogen. In some such embodiments, $X_3$ is F, Cl or Br. In some such embodiments, $X_3$ is F. In some such embodiments, $X_3$ is Cl.

In some embodiments of Formula II, $X_1$, $X_2$ and $X_3$ are hydrogen.

In some embodiments of Formula II, $X_1$ and $X_2$ are halogen and $X_3$ is hydrogen. In some such embodiments, $X_1$ and $X_2$ are F. In some such embodiments, $X_1$ and $X_2$ are Cl. In some such embodiments, $X_1$ and $X_2$ are Br.

In some embodiments of Formula II, $X_1$ and $X_3$ are halogen and $X_2$ is hydrogen. In some such embodiments, $X_1$ and $X_3$ are F. In some such embodiments, $X_1$ and $X_3$ are Cl. In some such embodiments, $X_1$ and $X_3$ are Br.

In some embodiments of Formula II, $X_2$ and $X_3$ are halogen and $X_1$ is hydrogen. In some such embodiments, $X_2$ and $X_3$ are F. In some such embodiments, $X_2$ and $X_3$ are Cl. In some such embodiments, $X_2$ and $X_3$ are Br.

In a third broad aspect there are provided compounds of Formula III, or pharmaceutically acceptable salts thereof.

Formula III

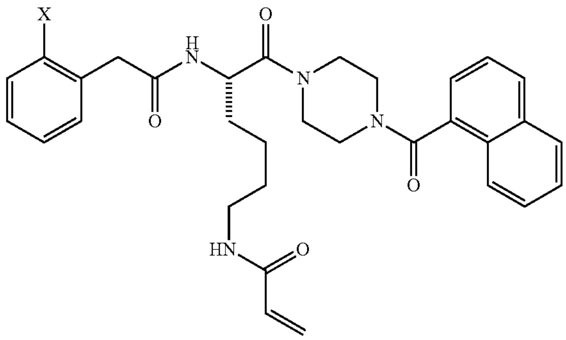

wherein:

X is hydrogen, halogen, substituted or unsubstituted $C_{1-6}$ alkyl, or substituted or unsubstituted $C_{1-6}$ alkoxy.

In some embodiments of Formula III, X is halogen. In some such embodiments, X is F, Cl or Br.

In other embodiments of Formula III, X is hydrogen.

In other embodiments of Formula III, X is substituted or unsubstituted $C_{1-6}$ alkyl. In some such embodiments, X is $C_1$-alkyl (i.e. —$CH_3$ or "Me"). In some such embodiments, X is trifluoromethyl ($CF_3$).

In other embodiments of Formula III, X is substituted or unsubstituted $C_{1-6}$ alkoxy. In some such embodiments, X is $C_1$-alkoxy (OMe).

In some embodiments of Formula III, X is hydrogen, F, Cl, Br, Me, OMe, or $CF_3$.

In some embodiments of Formula III, X is F.

In some embodiments of Formula III, X is Me.

In another broad aspect, there are provided pharmaceutical compositions comprising a compound described herein, or a pharmaceutically acceptable salt thereof, and a pharmaceutically acceptable carrier. In some embodiments, there are provided pharmaceutical compositions comprising a compound of Formula I or a pharmaceutically acceptable salt thereof, and a pharmaceutically acceptable carrier. In some embodiments, there are provided pharmaceutical compositions comprising a compound of Formula II, or a pharmaceutically acceptable salt thereof, and a pharmaceutically acceptable carrier. In some embodiments, there are provided pharmaceutical compositions comprising a compound of Formula III, or a pharmaceutically acceptable salt thereof, and a pharmaceutically acceptable carrier.

In yet another aspect, there are provided methods of inhibiting TG2, comprising contacting the TG2 in vitro with a compound described herein, or a pharmaceutically acceptable salt thereof, in an amount sufficient to inhibit one or more activity of the TG2. For example, GTPase, GTP binding, deamidation activity, and/or transamidation activity of TG2 may be inhibited or reduced, and/or TG2 may be held in an open conformation by the compound or the pharmaceutically acceptable salt. The compound may be, e.g., a compound of Formula I, Formula II, or Formula III, or a pharmaceutically acceptable salt thereof.

In another broad aspect, there are provided methods of inhibiting TG2 in a subject, comprising administering to the subject an effective amount of a compound described herein, or a pharmaceutically acceptable salt thereof, so as to inhibit one or more activity of TG2 in the subject. For example, GTPase activity, GTP binding activity, deamidation activity, and/or transamidation activity of TG2 may be inhibited or reduced in the subject, and/or TG2 may be held in an open conformation. Consequently, there are provided methods of treating or preventing a disease state mediated by TG2 in a subject in need of such treatment, comprising administering to the subject an effective amount of at least one compound or pharmaceutically acceptable salt thereof, or composition thereof, as described herein.

In some embodiments of methods provided herein, the compound is a compound of Formula I, as described above, or a pharmaceutically acceptable salt thereof. In some embodiments of methods provided herein, the compound is a compound of Formula II, as described above, or a pharmaceutically acceptable salt thereof. In some embodiments of methods provided herein, the compound is a compound of Formula III, as described above, or a pharmaceutically acceptable salt thereof.

In some embodiments of methods provided herein, the compound is a compound shown in Table 4, or a pharmaceutically acceptable salt thereof.

In some embodiments of methods provided herein, the compound is any one of compounds 67-81, or a pharmaceutically acceptable salt thereof.

In another broad aspect, therapeutic methods of use of the compounds and compositions described herein for the prevention and treatment of cancer are provided. In an embodiment, there are provided methods of treating a cancer in a subject in need thereof, comprising administering to the subject an effective amount of a compound described herein, or a pharmaceutically acceptable salt thereof, so as to treat the cancer in the subject. In some embodiments, the compound is a compound of Formula I or Formula II or Formula III as described above, or a compound of Table 4, or a pharmaceutically acceptable salt thereof. In some embodiments, one or more activity of TG2 activity is inhibited in the subject, e.g., GTPase activity, GTP binding, deamidation activity, and/or transglutaminase activity are inhibited or reduced in the subject.

In some embodiments, the cancer is a blood-cell derived cancer such as, without limitation, a lymphoma, a leukemia, or a myeloma. In some embodiments, the cancer is a solid organ tumor such as, without limitation, a tumor of the colon, breast, lung, prostate, brain, pancreas, ovary, or skin. In an embodiment, the cancer is an epidermal squamous cell carcinoma (SCC). In another embodiment, the cancer is a glioma, such as a malignant glioma or a glioblastoma, e.g., glioblastoma multiforme (GBM).

In some embodiments, the cancer is drug- or chemo-resistant. In some embodiments, the cancer is drug- or chemo-resistant and the compound or pharmaceutically acceptable salt acts to sensitize or re-sensitize the cancer to the drug or chemotherapy, e.g., the compound or pharmaceutically acceptable salt acts to increase the sensitivity of refractory cancer cells to chemotoxic agents or to overcome resistance to chemotherapy.

In some embodiments, cancer recurrence is prevented or inhibited in the subject, e.g., recurrence after surgical removal of a tumor is prevented or inhibited.

In some embodiments, metastasis is prevented or inhibited in the subject. EMT is the first critical step in metastasis, which is the most important feature of malignant tumors. During the morphogenetic process of EMT, epithelial cells lose epithelial characteristics and take on invasive mesenchymal properties. In some embodiments, therefore, the EMT transition is prevented or inhibited.

In some embodiments, cancer stem cell (CSC) survival or proliferation is prevented or inhibited. In an embodiment, epidermal cancer stem (ECS) cell survival or proliferation is prevented or inhibited. In an embodiment, CSC or ECS spheroid formation is prevented or inhibited.

In some embodiments, cancer (e.g., tumor) progression, growth, migration, and/or invasion is prevented or inhibited. For example, migration of cancer cells, e.g., GBM cells, may be prevented or inhibited by the compound or pharmaceutically acceptable salt. Cancer invasion, e.g., malignant glial cell (MGC) invasion, may be inhibited. In an embodiment, progression of a cancer is delayed.

In another embodiment, there is provided a method for enhancing the efficacy of a cancer therapy for the treatment of a cancer, comprising administering a compound described herein, or a pharmaceutically acceptable salt thereof, to a subject in need thereof, and simultaneously, separately or sequentially administering the cancer therapy. Non-limiting examples of the cancer therapy include surgical resection, chemotherapy, radiation therapy, immunotherapy, and gene therapy.

In another broad aspect, therapeutic methods of use of the compounds and compositions described herein for the prevention and treatment of a neurodegenerative disease are provided. The neurodenerative disease may be, for example and without limitation, Huntington's disease, Parkinson's disease, or Alzheimer's disease. In an embodiment, there are provided methods of treating a neurodegenerative disease in a subject in need thereof, comprising administering to the subject an effective amount of a compound described herein, or a pharmaceutically acceptable salt thereof, so as to treat the neurodegenerative disease in the subject. In some embodiments, the compound is a compound of Formula I or Formula II or Formula III as described above, or a compound of Table 4, or a pharmaceutically acceptable salt thereof. In some embodiments, one or more activity of TG2 activity is inhibited in the subject, e.g., GTPase activity, GTP binding, deamidation activity, and/or transglutaminase activity are inhibited or reduced in the subject.

In another broad aspect, therapeutic methods of use of the compounds and compositions described herein for the prevention and treatment of Celiac disease are provided. In an embodiment, there are provided methods of treating Celiac disease in a subject in need thereof, comprising administering to the subject an effective amount of a compound described herein, or a pharmaceutically acceptable salt thereof, so as to treat the Celiac disease in the subject. In some embodiments, the compound is a compound of Formula I or Formula II or Formula III as described above, or a compound of Table 4, or a pharmaceutically acceptable salt thereof. In some embodiments, one or more activity of TG2 activity is inhibited in the subject, e.g., GTPase activity, GTP binding, deamidation activity, and/or transglutaminase activity are inhibited or reduced in the subject.

In another broad aspect, therapeutic methods of use of the compounds and compositions described herein for the prevention and treatment of fibrosis are provided. In an embodiment, there are provided methods of treating fibrosis in a subject in need thereof, comprising administering to the subject an effective amount of a compound described herein, or a pharmaceutically acceptable salt thereof, so as to treat fibrosis in the subject. In some embodiments, the compound is a compound of Formula I or Formula II or Formula III as described above, or a compound of Table 4, or a pharmaceutically acceptable salt thereof. In some embodiments, one or more activity of TG2 activity is inhibited in the subject, e.g., GTPase activity, GTP binding, deamidation activity, and/or transglutaminase activity are inhibited or reduced in the subject.

In another broad aspect, therapeutic methods of use of the compounds and compositions described herein for the prevention and treatment of multiple sclerosis (MS) are provided. In an embodiment, there are provided methods of treating MS in a subject in need thereof, comprising administering to the subject an effective amount of a compound described herein, or a pharmaceutically acceptable salt thereof, so as to treat the MS in the subject. In some embodiments, the compound is a compound of Formula I or Formula II or Formula III as described above, or a compound of Table 4, or a pharmaceutically acceptable salt thereof. In some embodiments, one or more activity of TG2 activity is inhibited in the subject, e.g., GTPase activity, GTP binding, deamidation activity, and/or transglutaminase activity are inhibited or reduced in the subject.

In another broad aspect, therapeutic methods of use of the compounds and compositions described herein for the prevention and treatment of central nervous system (CNS) injury are provided. In an embodiment, there are provided methods of treating CNS injury in a subject in need thereof, comprising administering to the subject an effective amount of a compound described herein, or a pharmaceutically acceptable salt thereof, so as to treat the CNS injury in the subject. In some embodiments, the compound is a compound of Formula I or Formula II or Formula III as described above, or a compound of Table 4, or a pharmaceutically acceptable salt thereof. In some embodiments, one or more activity of TG2 activity is inhibited in the subject, e.g., GTPase activity, GTP binding, deamidation activity, and/or transglutaminase activity are inhibited or reduced in the subject. Non-limiting examples of CNS injuries include traumatic brain injury (TBI), spinal cord injury (SCI), stroke, and surgery to the CNS (e.g., placing an electrode for deep-brain stimulation, temporal lobe resection, or other invasive trauma). In some such embodiments, the compound or composition is administered topically and/or locally at the site of injury.

In some embodiments, there are provided methods of treating spinal cord injury (SCI) in a subject in need thereof, comprising administering to the subject an effective amount of a compound described herein, or a pharmaceutically acceptable salt thereof, so as to treat SCI in the subject. In some embodiments, functional recovery after SCI is improved in the subject. In some embodiments, the compound is a compound of Formula I or Formula II or Formula III as described above, or a compound of Table 4, or a pharmaceutically acceptable salt thereof. In some embodiments, one or more activity of TG2 activity is inhibited in the subject, e.g., GTPase activity, GTP binding, deamidation activity, and/or transglutaminase activity are inhibited or reduced in the subject. In some such embodiments, the compound or composition is administered topically and/or locally at the site of SCI.

In some embodiments, there are provided methods of treating stroke in a subject in need thereof, comprising administering to the subject an effective amount of a compound described herein, or a pharmaceutically acceptable salt thereof, so as to treat stroke in the subject. In some embodiments, the compound is a compound of Formula I or Formula II or Formula III as described above, or a compound of Table 4, or a pharmaceutically acceptable salt thereof. In some embodiments, one or more activity of TG2 activity is inhibited in the subject, e.g., GTPase activity, GTP binding, deamidation activity, and/or transglutaminase activity are inhibited or reduced in the subject. In some such embodiments, the compound or composition is administered topically and/or locally at the site of stroke.

In some embodiments, there are provided methods of inhibiting reactive gliosis in a subject in need thereof, comprising administering to the subject an effective amount of a compound described herein, or a pharmaceutically acceptable salt thereof, so as to inhibit reactive gliosis in the subject. In some embodiments, the compound is a compound of Formula I or Formula II or Formula III as described above, or a compound of Table 4, or a pharmaceutically acceptable salt thereof. In some embodiments, one or more activity of TG2 activity is inhibited in the subject, e.g., GTPase activity, GTP binding, deamidation activity, and/or transglutaminase activity are inhibited or reduced in the subject. In some such embodiments, the compound or composition is administered topically and/or locally in the CNS, e.g., at the site of neural injury or damage.

In some embodiments of methods of the disclosure, astrocyte function is modulated in the subject, e.g., reactive gliosis is inhibited and/or glial scarring is blocked or reduced.

In a further aspect, there are provided kits for treating a disease state mediated by TG2 in a subject in need thereof, comprising a compound (or a pharmaceutically acceptable salt thereof) or a pharmaceutical composition, as described herein; optionally one or more additional component such as acids, bases, buffering agents, inorganic salts, solvents, antioxidants, preservatives, or metal chelators; and instructions for use thereof.

BRIEF DESCRIPTION OF THE DRAWINGS

For a better understanding of the invention and to show more clearly how it may be carried into effect, reference will now be made by way of example to the accompanying drawings, which illustrate aspects and features according to embodiments of the present invention, and in which:

FIGS. 2A-2E show transglutaminase isozyme selectivity of inhibitor compounds AA9 and 72 using an appropriate activity assay, wherein: FIG. 2A shows inhibition of FXIIIa; FIG. 2B shows inhibition of TG3a; FIG. 2C shows inhibition of TG1; FIG. 2D shows inhibition of TG6; and FIG. 2E shows inhibition of TG2. Red line: enzyme activity; black line: enzyme activity in presence of AA9; blue line: enzyme activity in presence of compound 72.

FIGS. 3A-3E show transglutaminase isozyme selectivity of inhibitor compound 74 using an appropriate activity assay, wherein: FIG. 3A shows inhibition of FXIIIa; FIG. 3B shows inhibition of TG3a; FIG. 3C shows inhibition of TG1; FIG. 3D shows inhibition of TG6; and FIG. 3E shows inhibition of TG2. In FIGS. 3A-3B, the blue line shows enzyme activity and the purple line shows enzyme activity in presence of compound 74. In FIGS. 3C-3E, the blue line shows enzyme activity, and the red and green lines show two different measurements of the enzyme activity in the presence of compound 74.

DETAILED DESCRIPTION

Figure 1:
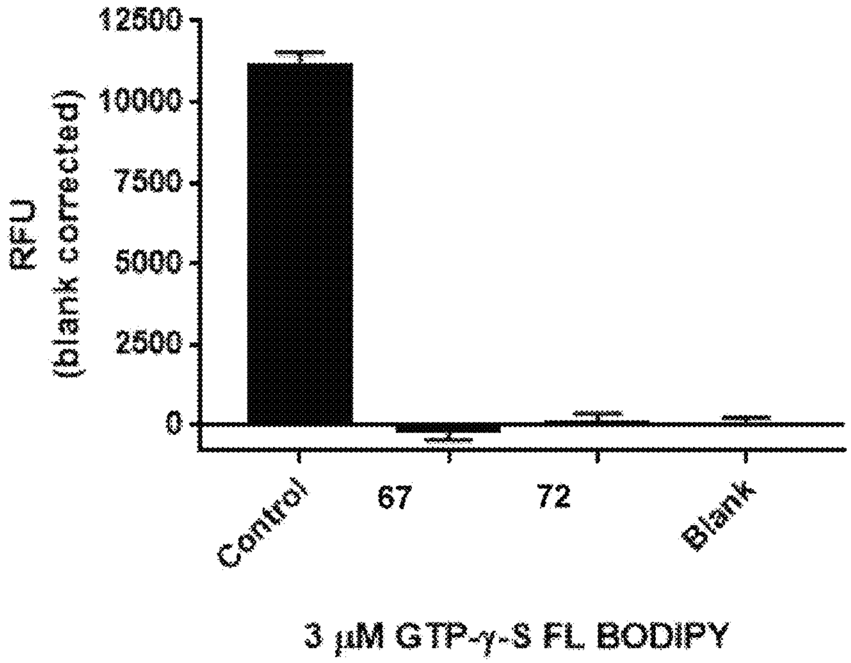
FIG. 1 shows inhibition of GTP binding of human TG2 (hTG2) by inhibitor compounds 67 and 72 in an in vitro GTP binding assay.
Figure 2A:
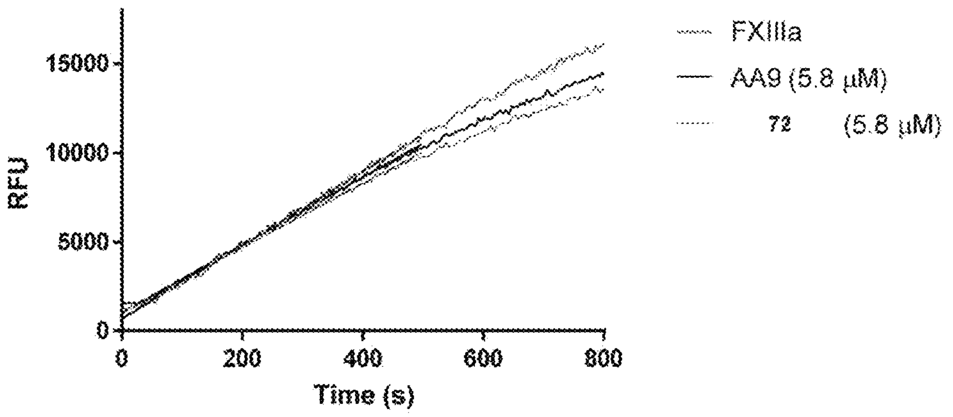
Figure 2B:
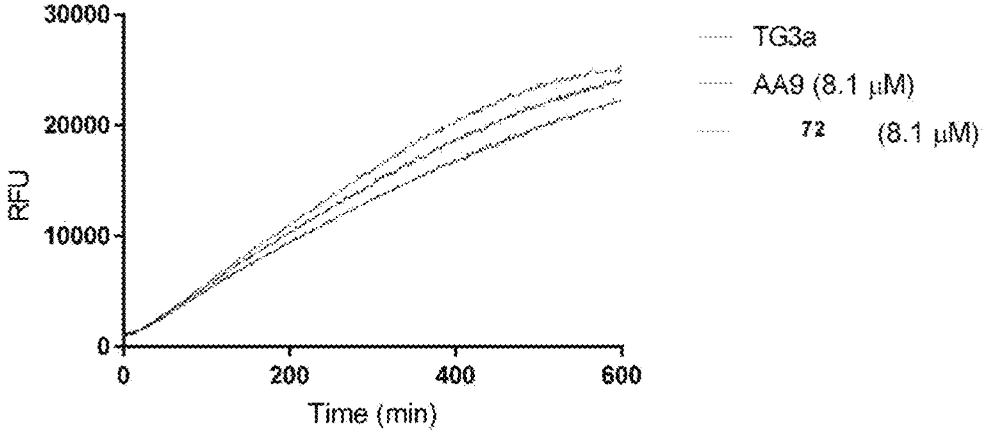
Figure 2C:
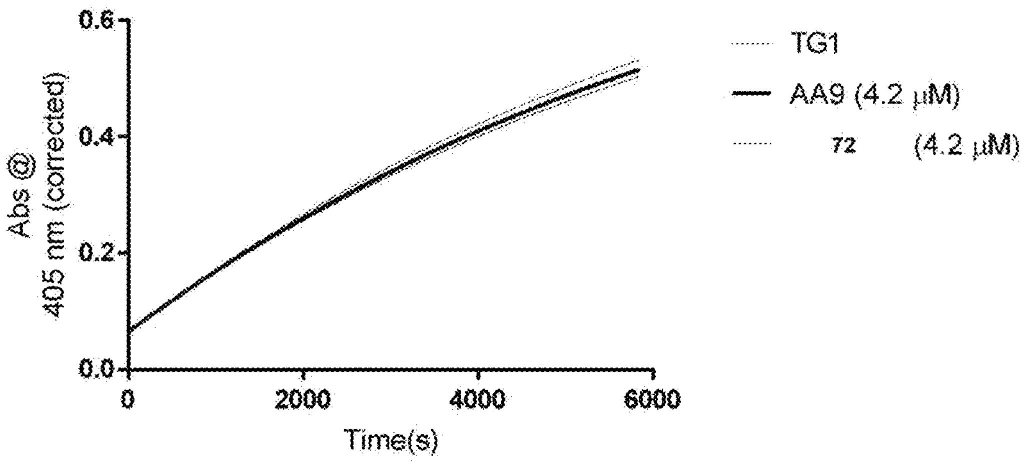
Figure 2D:
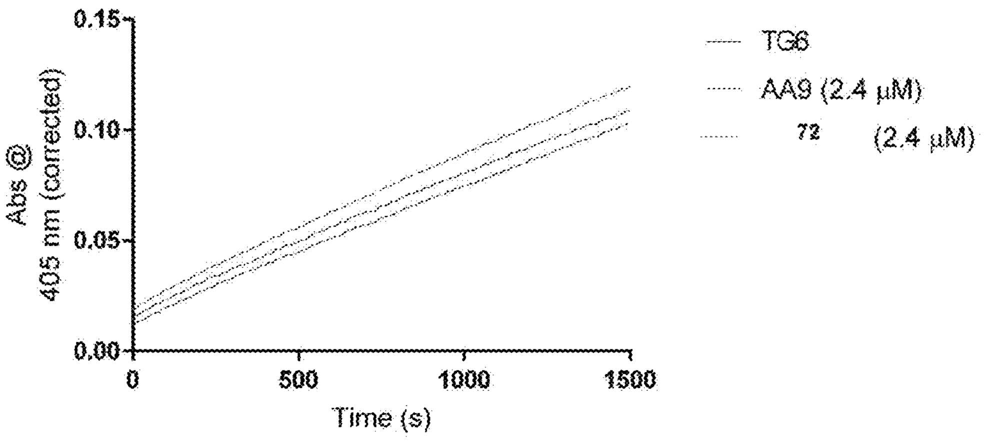
Figure 2E:
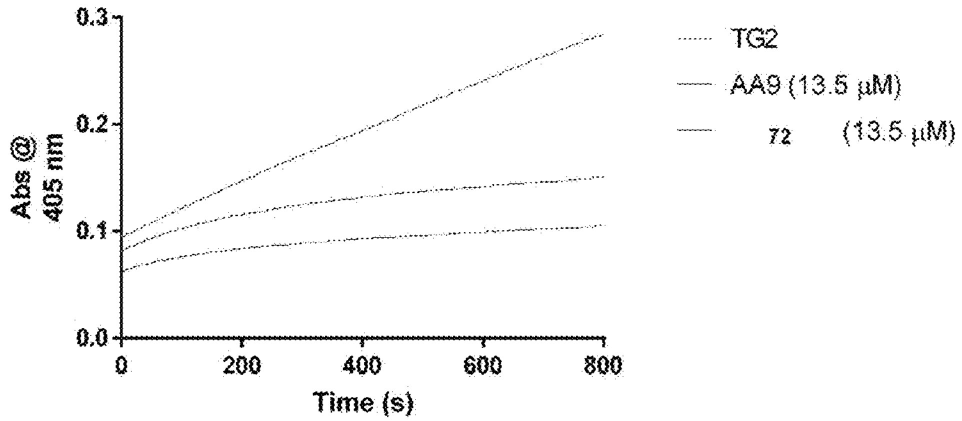
Figure 3A:
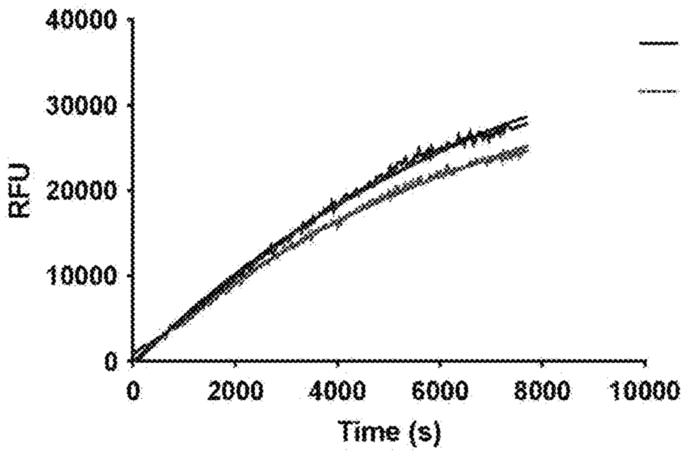
Figure 3B:
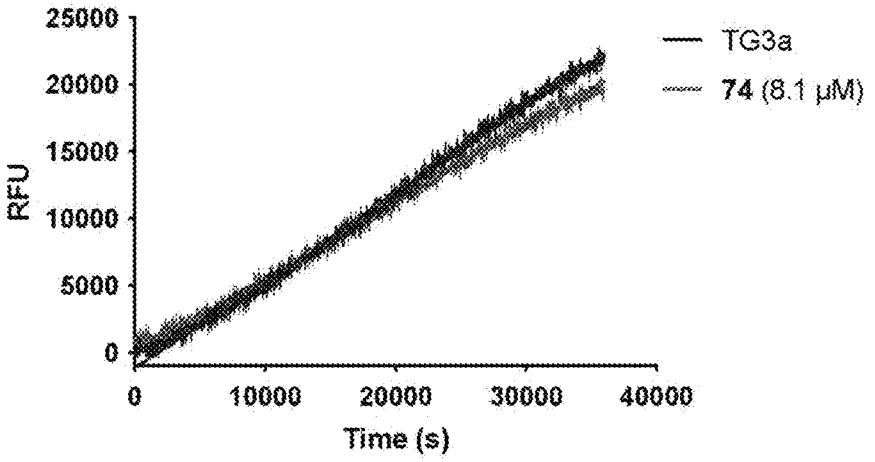
Figure 3C:
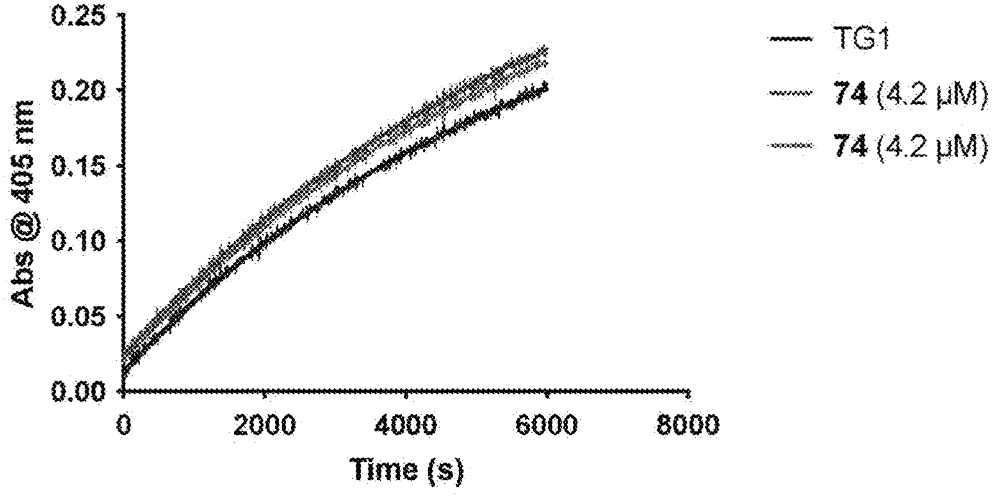
Figure 3D:
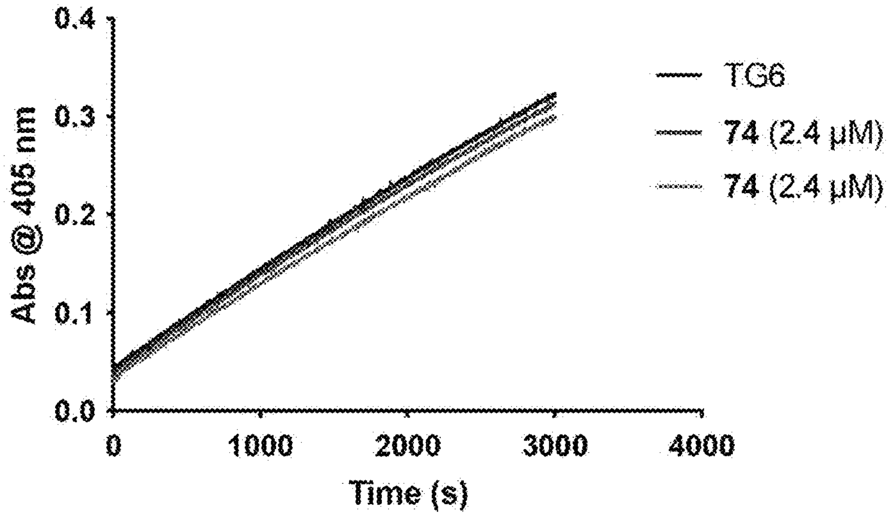
Figure 3E:
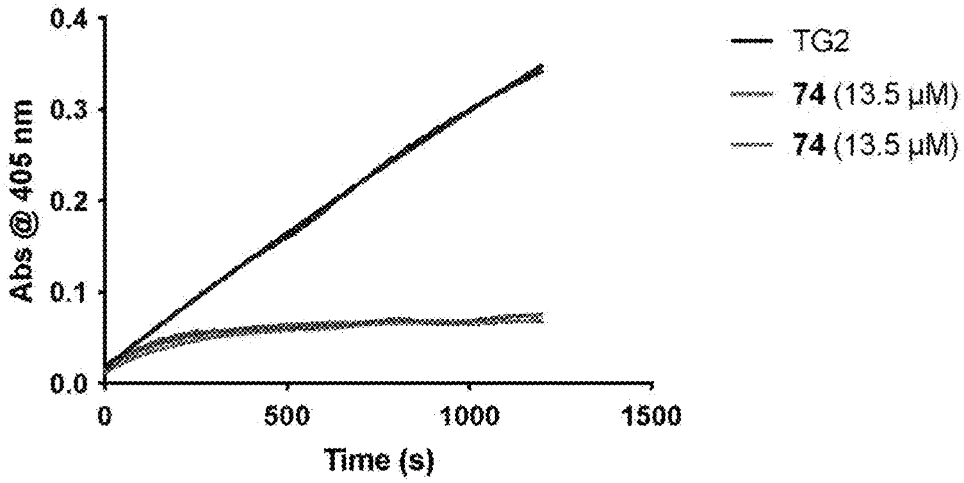

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes an inherent variation of error for the device or the method being employed to determine the value.

The term "derivative" as used herein, is understood as being a substance similar in structure to another compound but differing in some slight structural detail.

The present description refers to a number of chemical terms and abbreviations used by those skilled in the art. Nevertheless, definitions of selected terms are provided for clarity and consistency.

As used herein, the terms "alkyl" and "$C_{1-6}$ alkyl" can be straight-chain or branched. Examples of alkyl residues containing from 1 to 6 carbon atoms are methyl, ethyl, propyl, butyl, pentyl, hexyl, the n-isomers of all these residues, isopropyl, isobutyl, isopentyl, neopentyl, isohexyl, 3-methylpentyl, sec-butyl, tert-butyl, or tert-pentyl. Alkyl residues may be substituted or unsubstituted. In some embodiments, for example, alkyl may be substituted by hydroxyl, amino, carboxyl, carboxylic ester, amide, carbamate, or aminoalkyl.

As used herein, the term "cycloalkyl" can be monocyclic or polycyclic, for example monocyclic, bicyclic or tricyclic, i.e., they can for example be monocycloalkyl residues, bicycloalkyl residues and tricycloalkyl residues, provided they have a suitable number of carbon atoms and the parent hydrocarbon systems are stable. A bicyclic or tricyclic cycloalkyl residue has to contain at least 4 carbon atoms. In an embodiment, a bicyclic or tricyclic cycloalkyl residue contains at least 5 carbon atoms. In a further embodiment, a bicyclic or tricyclic cycloalkyl residue contains at least 6 carbon atoms and up to the number of carbon atoms specified in the respective definition. Cycloalkyl residues can be saturated or contain one or more double bonds within the ring system. In particular they can be saturated or contain one double bond within the ring system. In unsaturated cycloalkyl residues the double bonds can be present in any suitable positions. Monocycloalkyl residues are, for example, cyclopropyl, cyclobutyl, cyclopentyl, cyclopentenyl, cyclohexyl, cyclohexenyl, cycloheptyl, cycloheptenyl, cyclooctyl, cyclononyl, cyclodecyl, cycloundecyl, cyclododecyl or cyclotetradecyl, which can also be substituted, for example by $C_{1-4}$ alkyl. Examples of substituted cycloalkyl residues are 4-methylcyclohexyl and 2,3-dimethylcyclopentyl. Examples of parent structures of bicyclic ring systems are norbornane, bicyclo[2.2.1]heptane, bicyclo[2.2.2]octane and bicyclo[3.2.1]octane.

As used herein, the term "aryl" means an aromatic substituent that is a single ring or multiple rings fused together. When formed of multiple rings, at least one of the constituent rings is aromatic. In an embodiment, aryl substituents include phenyl, naphthyl and anthracyl groups.

The term "heteroaryl", as used herein, is understood as being aromatic rings of five or six atoms containing one or two O- and/or S-atoms and/or one to four N-atoms, provided that the total number of hetero-atoms in the ring is 4 or less. The heteroaryl ring is attached by way of an available carbon or nitrogen atom. Non-limiting examples of heteroaryl groups include 2-, 3-, or 4-pyridyl, 4-imidazolyl, 4-thiazolyl, 2- and 3-thienyl, and 2- and 3-furyl. The term "heteroaryl", as used herein, is understood as also including bicyclic rings wherein the five or six membered ring containing O, S and N-atoms as defined above is fused to a benzene or pyridyl ring. Non-limiting examples of bicyclic rings include but are not limited to 2- and 3-indolyl as well as 4- and 5-quinolinyl.

As used herein, the term "arylalkyl" means an aryl group that is attached through an alkylene group to the parent moiety, wherein aryl and alkyl are as defined herein. Non-limiting examples of arylalkyl include benzyl, naphthalene-1-ylmethyl, and naphthalene-2-ylmethyl.

As used herein, the term "halogen" includes fluorine (F), chlorine (Cl), bromine (Br), and iodine (I). Similarly, the term "halo" includes fluoro, chloro, bromo, and iodo.

TG2 Inhibitor Compounds

In a broad aspect, the present disclosure relates to TG2 inhibitor compounds, and their use as therapeutics. It is noted that the TG2 enzyme catalyzes a transamidation reaction between protein-bound glutamine and lysine residues, resulting in the cross-linking of proteins. This acyl-transfer reaction is mediated by a catalytic triad that resembles that of the calpain-type cysteine proteases. TG2 transamidation activity is important among other things for stabilizing the extracellular matrix (ECM). TG2 also binds GTP in the cytosol and modulates signal transduction by participating in G protein signaling.

TG2 transamidation and GTP-binding activities are mutually exclusive and ligand dependent; calcium is required for transamidation activity, whereas the presence of guanosine nucleotides suppresses it. Early spectroscopic studies suggested this was due to significant conformational changes, for which crystallographic studies have since provided direct structural evidence. TG2 has been crystallized in two strikingly different forms, both of which comprise four structurally distinct domains. In the presence of GDP, the enzyme adopts a "closed" conformation, wherein these four domains are arranged in a compact tertiary structure. In contrast, after reaction with an irreversible inhibitor in the presence of calcium, the enzyme was crystallized in an "open" conformation, where the same four domains are arranged in an extended linear tertiary structure (Pinkas, D. M. et al., *PLoS Biol.* 5: e327, 2007).

Without wishing to be limited by theory, it is believed that TG2 inhibitor compounds described herein may act as active site directed irreversible inhibitors of TG2 that lock the enzyme in its "open" conformation which does not bind GTP. Thus, TG2 inhibitor compounds described herein may exploit the reactivity of the active site residues to covalently attach to the enzyme, and upon binding they lock the enzyme in a conformation that cannot bind GTP, thereby abolishing that activity in addition to transglutaminase activity. TG2 inhibitor compounds described herein are thus distinct from previously known inhibitors of TG2 that may bind the catalytic active site, blocking transamidation activity, but do not inhibit GTP binding.

In an embodiment, there is provided a compound of Formula I, Formula II, or Formula III, or a pharmaceutically acceptable salt thereof, as described herein.

In an embodiment, there is provided a compound of Table 4, i.e., compounds 67-81, as described herein, or a pharmaceutically acceptable salt thereof.

In some embodiments, compounds described herein inhibit one or more activity of TG2, e.g., GTPase activity, GTP binding activity, deamidation activity, and/or transamidation activity. In some embodiments, compounds described herein hold the TG2 in an open conformation, e.g., in a conformation that does not bind to TG2.

In some embodiments, compounds described herein are irreversible inhibitors of TG2. Pharmaceutical compositions and therapeutic methods comprising the compounds described herein or pharmaceutically acceptable salts thereof, are also encompassed.

As would be understood by a person of ordinary skill in the art, the recitation of "a compound" is intended to include salts, solvates, oxides, and inclusion complexes of that compound as well as any stereoisomeric form, or a mixture of any such forms of that compound in any ratio. Thus, in accordance with some embodiments of the invention, a compound as described herein, including in the contexts of pharmaceutical compositions and methods of treatment is provided as the salt form.

Compounds described herein include, but are not limited to, their optical isomers, racemates, and other mixtures thereof. In those situations, the single enantiomers or diastereomer, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, such compounds include Z- and E-forms (or cis- and trans-forms) of compounds with carbon-carbon double bonds. Where compounds described herein exist in various tautomeric forms, the term "compound" is intended to include all tautomeric forms of the compound. Such compounds also include crystal forms including polymorphs and clathrates. Similarly, the term "salt" is intended to include all tautomeric forms and crystal forms of the compound.

The configuration of any carbon-carbon double bond appearing herein is selected for convenience only and is not intended to designate a particular configuration; thus a carbon-carbon double bond depicted arbitrarily herein as E may be Z, E, or a mixture of the two in any proportion.

The term "solvate" refers to a compound in the solid state, where molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

For compounds provided herein, it is intended that, in some embodiments, salts thereof are also encompassed, including pharmaceutically acceptable salts. Those skilled in the art will appreciate that many salt forms (e.g., TFA salt, tetrazolium salt, sodium salt, potassium salt, etc) are possible; appropriate salts are selected based on considerations known in the art. The term "pharmaceutically acceptable salt" refers to salts prepared from pharmaceutically acceptable non-toxic acids or bases including inorganic acids and bases and organic acids and bases. For example, for compounds that contain a basic nitrogen, salts may be prepared from pharmaceutically acceptable non-toxic acids including inorganic and organic acids. Suitable pharmaceutically acceptable acid addition salts for the compounds of the present invention include without limitation acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include without limitation metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine), and procaine.

Compositions

There are provided pharmaceutical compositions comprising a compound described herein, or a pharmaceutically acceptable salt thereof, and a pharmaceutically acceptable carrier.

In an embodiment, there is provided a pharmaceutical composition comprising a compound of Formula I, Formula II, or Formula III, or a pharmaceutically acceptable salt thereof, and a pharmaceutically acceptable carrier. In an embodiment, there is provided a pharmaceutical composition comprising any one of compounds 67-81, or a pharmaceutically acceptable salt thereof, and a pharmaceutically acceptable carrier. In another embodiment, there is provided a pharmaceutical composition comprising compound 72 or 74, or a pharmaceutically acceptable salt thereof, and a pharmaceutically acceptable carrier.

The preparation of pharmaceutical compositions can be carried out as known in the art (see, for example, Remington: The Science and Practice of Pharmacy, $20^{th}$ Edition, 2000). For example, a therapeutic compound and/or composition, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine. Pharmaceutical preparations can also contain additives, of which many are known in the art, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The term "pharmaceutical composition" means a composition comprising a compound as described herein and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

The term "pharmaceutically acceptable carrier" is used to mean any carrier, diluent, adjuvant, excipient, or vehicle, as described herein. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of a subject, e.g., humans and animals, without undue toxicity, irritation, allergic response, and the like, and are commensurate with a reasonable benefit/risk ratio.

A pharmaceutically acceptable carrier may include any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier may be suitable for intravenous, intraperitoneal, intramuscular, sublingual or oral administration. In other embodiments, the carrier is suitable for topical administration or for administration via inhalation. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions provided herein is contemplated. Supplementary active compounds can also be incorporated into the compositions. For example, a pharmaceutical composition provided herein may further comprise at least one additional therapeutic, e.g., an additional cancer therapeutic, as discussed below.

A pharmaceutical composition provided herein can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, creams, tinctures, sprays or transdermal therapeutic systems, or the inhalative administration in the form of nasal sprays or aerosol mixtures, or, for example, microcapsules, implants or wafers.

Pharmaceutical compositions typically must be sterile and stable under the conditions of manufacture and storage. A composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of injectable compositions can be brought about by including in the composition an agent which delays absorption, for example, monostearate salts and gelatin. Moreover, a compound can be administered in a time release formulation, for example in a composition which includes a slow-release polymer. The compound can be prepared with carriers that will protect against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG).

Many methods for the preparation of such formulations are generally known to those skilled in the art. Sterile injectable solutions can be prepared by incorporating an active compound, such as a TG2 inhibitor compound provided herein, in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, common methods of preparation are vacuum drying and freeze-drying which yields a powder of the active ingredient plus any additional desired ingredient from a previously sterile-filtered solution thereof. Compounds may also be formulated with one or more additional compounds that enhance their solubility.

It is often advantageous to formulate compositions (such as parenteral compositions) in dosage unit form for ease of administration and uniformity of dosage. The term "unit dosage form" refers to a physically discrete unit suitable as unitary dosages for human subjects and other animals, each unit containing a predetermined quantity of active material calculated to produce the desired therapeutic effect, in association with a suitable pharmaceutical carrier. The specification for the dosage unit forms of the invention may vary and are dictated by and directly dependent on (a) the unique characteristics of the therapeutic compound and the particular therapeutic effect to be achieved, and (b) the limitations inherent in the art of compounding such a therapeutic compound for the prevention or treatment of cancer. Dosages are discussed further below.

In some embodiments, there are provided pharmaceutical compositions that comprise an effective amount of a compound and/or composition described herein, and a pharmaceutically acceptable carrier. In an embodiment, there are provided pharmaceutical compositions for the treatment or prevention of a TG2-associated disease or disorder, such as for example a cancer, comprising a compound described herein, or a pharmaceutically acceptable salt thereof, and a pharmaceutically acceptable carrier.

In an embodiment, there is provided a pharmaceutical composition for the delay of progression of a cancer, for the inhibition of cancer invasion, e.g., malignant glial cell (MGC) invasion, for inhibition of cancer stem cell growth, survival, spheroid formation and/or proliferation, for inhibition of metastasis, for inhibition of cancer recurrence, and/or for overcoming chemoresistance of a cancer, the composition comprising a compound described herein, or a pharmaceutically acceptable salt thereof, and a pharmaceutically acceptable carrier.

Methods of Use of Compounds and Compositions

There are provided methods of treating or preventing a disease state mediated by TG2 in a subject in need of such treatment, comprising administering to the subject an effective amount of at least one compound or pharmaceutically acceptable salt thereof, or composition thereof, as described herein.

As used herein, the terms “disease state mediated by TG2” and “TG2-associated disease or disorder” are used interchangeably to refer to any pathological medical condition that would benefit from treatment with a TG2 inhibitor compound of the disclosure or pharmaceutical composition thereof as described herein. This includes chronic and acute disorders or diseases including those pathological conditions that predispose the subject to the disease or disorder in question. A TG2-associated disease or disorder is thus a disease or disorder that may be ameliorated through inhibition of one or more activity of TG2 including without limitation GTP binding, GTPase activity, deamidation, and/or transamidation. As such, there are provided methods for prevention or treatment of a TG2-associated disease or disorder in a subject, the methods comprising administering a therapeutically effective amount of the inhibitor compound or pharmaceutical composition described herein. Inhibitor compounds are generally administered in the form of a pharmaceutical composition. A subject may be in need of such treatment, i.e., having, suspected of having, or at risk of having a disease or disorder associated with TG2.

In some embodiments, TG2-associated diseases or disorders include, for example and without limitation, neurodegenerative diseases, gluten sensitivity diseases such as Celiac disease, protein misfolding disorders, hepatic and renal injury, kidney disease, renal failure, neuropathy, cancer metastasis, leukemia, melanoma, autoimmune diseases, inflammatory diseases, degenerative joint disease such as osteoarthritis, psoriasis, cardiovascular disorders, ischemia, atherosclerosis, fibrosis, diabetes, lamellar ichthyosis, supranuclear palsey, Hb Koln and sickle cell disorders, acne, cataracts, myopia, immune system diseases, diabetic nephropathy, muscular dystrophies, wound remodelling and repair, multiple sclerosis, and central nervous system (CNS) injury such as traumatic brain injury (TBI), spinal cord injury (SCI), and stroke. In some embodiments, the TG2-associated disease or disorder is chosen from acne, cataracts, immune system diseases, psoriasis, neuropathy, neurodegenerative disease, such as Alzheimer’s disease, Huntington’s disease, and Parkinson’s disease, Celiac disease, cancer metastasis, inflammation, fibrosis, diabetes, autoimmune diseases, lamellar ichthyosis, psoriasis, supranuclear palsy, and renal failure. In some embodiments, the TG2-associated disease or disorder is a gluten sensitivity disease. In some embodiments, the TG2-associated disease or disorder is Celiac disease. In some embodiments, the TG2-associated disease or disorder is fibrosis. In some embodiments, the neurodegenerative disease is chosen from Alzheimer’s disease, amyotrophic lateral sclerosis, Huntington’s disease, Parkinson’s' disease, Prion disease, multiple sclerosis and spinocerebellar ataxias. In some embodiments, the neurodegenerative disease is Huntington’s disease. In some embodiments, the neurodegenerative disease is multiple sclerosis. In some embodiments, TG2-associated diseases or disorders include, for example and without limitation, a CNS injury such as TBI, SCI, and stroke.

In some embodiments, TG2-associated diseases or disorders include conditions associated with reactive gliosis. When the CNS is injured, astrocytes can undergo a process called “reactive gliosis” or “reactive astrogliosis”. The terms “reactive gliosis” and “reactive astrogliosis” are used interchangeably herein to refer to the morphological and/or functional changes that occur in astrocytes in response to CNS injury and other neurological diseases and conditions. Compared with nonreactive astrocytes, reactive astrocytes show altered expression of many genes and exhibit distinct morphological and functional features. Reactive gliosis is believed to be a defensive reaction aimed at handling acute stress in the CNS, limiting tissue damage, and restoring homeostasis. However, it can also inhibit adaptive neural plasticity mechanisms underlying functional recovery (Pekny, M. and Pekna, M., Physiol. Rev. (2013), 94(4): 1077-98). Therefore, inhibiting reactive gliosis can promote CNS repair and reduce neurological impairment after injury. As used herein, a “condition associated with reactive gliosis” refers to any disease or disorder of the CNS in which reactive gliosis occurs. For example and without limitation, conditions associated with reactive gliosis include TBI, SCI, stroke, trauma, ischemic damage, viral encephalopathy, surgery to the CNS (e.g., placing an electrode for deep-brain stimulation, temporal lobe resection, or other invasive trauma), neuroinflammation, and neurodegeneration (e.g., associated with Alzheimer’s disease, Parkinson’s disease, mild cognitive impairment, senility, etc.). In some embodiments, TG2-associated diseases or disorders include, for example and without limitation, a cancer. A cancer may be a blood-cell derived cancer such as, without limitation, a lymphoma, a leukemia, or a myeloma, or a solid organ tumor such as, without limitation, a tumor of the colon, breast, lung, prostate, brain, pancreas, ovary, or skin. In an embodiment, the cancer is an epidermal squamous cell carcinoma (SCC). In another embodiment, the cancer is a glioma, such as a malignant glioma or a glioblastoma, e.g., glioblastoma multiforme (GBM).

Consequently, in some embodiments there are provided methods for treating cancer, such as glioma, e.g., glioblastoma or GBM, or SCC, in a subject in need thereof, comprising administering a compound or a composition as described herein to the subject. In some embodiments, there is provided a method for delaying the progression of cancer, such as glioma, e.g., glioblastoma or GBM, or SCC, in a subject in need thereof, comprising administering a compound or a composition as described herein to a subject. In some embodiments, there are further provided methods for inhibiting or reducing the migration or invasiveness of tumor cells, e.g., cells of glioma such as glioblastoma, comprising administering a compound or composition provided herein to a subject in need thereof. In other embodiments, there are provided methods for sensitizing refractory cancer cells to chemotoxic agents; preventing or inhibiting cancer stem cell (CSC) growth, survival and/or proliferation; preventing or inhibiting CSC spheroid formation; and/or preventing or inhibiting metastasis, e.g., the EMT transition. In some embodiments, there are provided methods for preventing or inhibiting a cancer (e.g., tumor) progression, growth, migration, and/or invasion.

In some embodiments, there are provided methods for preventing or inhibiting recurrence of a cancer after treatment, e.g., after drug treatment or surgical excision. In some embodiments, there are provided methods for delaying the progression of a cancer, wherein cancer re-growth is delayed by more than 30%, or by more than 50%, or by more than 70%, and/or wherein the survival periods of affected subjects is increased. In one embodiment, there is provided a method for inhibiting brain cancer invasion, for example MGC invasion. In another embodiment, there is provided a method for inhibiting progression of SCC.

There is further provided a method for enhancing the efficacy of cancer therapies for the treatment of cancer, selected from the group comprising resection, chemotherapy, radiation therapy, immunotherapy, and/or gene therapy, comprising administering a TG2 inhibitor compound or composition as described herein, and simultaneously, separately or sequentially administrating said cancer therapy. The term "enhancing the efficacy of a cancer therapy", as used herein, refers to an improvement of conventional cancer treatments and includes reduction of the amount of the anti-cancer composition which is applied during the conventional cancer treatment, e.g. amount of radiation in radiotherapy, of chemotherapeutics in chemotherapy, of immunotherapeutics in immunotherapy or of vectors in gene based therapies, and/or to an increase in efficacy of the conventional therapy and the anti-cancer composition when applied at conventional doses or amounts during the conventional cancer therapy. In one embodiment, enhancing the efficacy of a cancer therapy refers to prolonging the survival rate of subjects receiving the therapy.

It should be understood that compounds and/or compositions provided herein may be used alone or in combination with other therapeutic agents, e.g., other cancer therapies. Non-limiting examples of other cancer therapies include resection of the cancer, chemotherapy, radiation therapy, immunotherapy, and/or gene-based therapy. The term "resection" refers to the surgical removal or excision of part or all of a tumor. The term "radiation therapy" refers to the treatment of cancer using radiation. The term "chemotherapy" refers to the treatment of cancer with chemical substances, so-called chemotherapeutics. The term "immunotherapy" as used herein refers to the stimulation of the reactivity of the immune system towards eliminating the cancer cells by using immunotherapeutics. The term "gene-based therapy" refers to the treatment of cancer based upon the transfer of genetic material (DNA, or possibly RNA) into an individual. Non-limiting examples of such other cancer therapies include: chemotherapeutics including but not limited to temozolomide, doxorubicin, vincristine, vinorelbine, procarbazine, carmustine, lomustine, taxol, taxotere, tamoxifen, retinoic acid, 5-fluorouracil, cyclophosphamide and thalidomide; immunotherapeutics such as but not limited to activated T cells and pulsed dendritic cells; gene transfer of CD3, CD7 and CD45 in glioma cells, concomitantly with the delivery of a compound or composition as defined herein.

Thus, compounds and/or compositions described herein may be administered alone or in combination with one or more additional therapy, e.g., one or more additional cancer therapy. The latter can be administered before, after or simultaneously with the administration of the compounds and/or compositions described herein.

In some embodiments, there are provided methods for treating a neurodegenerative disease in a subject in need of such treatment, comprising administering a compound or a composition as described herein to the subject. For example, there are provided methods for treating Huntington's disease, Parkinson's disease and/or Alzheimer's disease.

In a particular embodiment, there is provided a method for treating Huntington's disease in a subject in need thereof, comprising administering a therapeutically effective amount of a compound or composition as described herein to the subject. Such methods may include treating memory and/or cognitive impairment associated with Huntington's disease. In some embodiments, there are provided methods for treating Huntington's disease, including treating memory and/or cognitive impairment associated with Huntington's disease, comprising administering to a subject, simultaneously or sequentially, at least one compound or pharmaceutically acceptable salt thereof described herein and one or more additional agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone. In methods using simultaneous administration, the agents can be present in a combined composition or can be administered separately. As a result, also provided are pharmaceutical compositions comprising at least one compound or pharmaceutically acceptable salt thereof described herein and one or more additional pharmaceutical agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone. Similarly, also provided are packaged pharmaceutical compositions containing a pharmaceutical composition comprising at least one compound or pharmaceutically acceptable salt thereof described herein, and another composition comprising one or more additional pharmaceutical agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone.

In another embodiment, there is provided a method for treating Parkinson's disease in a subject in need thereof, comprising administering a therapeutically effective amount of a compound or composition as described herein to the subject. Such methods may include treating memory and/or cognitive impairment associated with Parkinson's disease. In some embodiments, there are provided methods for treating Parkinson's disease, including treating memory and/or cognitive impairment associated with Parkinson's disease, comprising administering to a subject, simultaneously or sequentially, at least one compound or pharmaceutically acceptable salt thereof described herein and one or more additional agents used in the treatment of Parkinson's disease such as, but not limited to, Levodopa, Parlodel, Permax, Mirapex, Tasmar, Contan, Kemadin, Artane, and Cogentin. In methods using simultaneous administration, the agents can be present in a combined composition or can be administered separately. Also provided are pharmaceutical compositions comprising at least one compound or pharmaceutically acceptable salt thereof described herein, and one or more additional pharmaceutical agents used in the treatment of Parkinson's disease, such as, but not limited to, Levodopa, Parlodel, Permax, Mirapex, Tasmar, Contan, Kemadin, Artane, and Cogentin. Also provided are packaged pharmaceutical compositions containing a pharmaceutical composition comprising at least one compound or pharmaceutically acceptable salt thereof described herein, and another composition comprising one or more additional pharmaceutical agents gent used in the treatment of Parkinson's disease such as, but not limited to, Levodopa, Parlodel, Permax, Mirapex, Tasmar, Contan, Kemadin, Artane, and Cogentin.

In another embodiment, there is provided a method for treating Alzheimer's disease in a subject in need thereof, comprising administering a therapeutically effective amount of a compound or composition as described herein to the subject. Such methods may include treating memory and/or cognitive impairment associated with Alzheimer's disease. In some embodiments, there are provided methods for treating Alzheimer's disease, including memory and/or cognitive impairment associated with Alzheimer's disease, comprising administering to a subject, simultaneously or sequentially, at least one compound or pharmaceutically acceptable salt thereof described herein and one or more additional agents used in the treatment of Alzheimer's disease such as, but not limited to, Reminyl®, Cognex®, Aricept®, Exelon®, Akatinol®, Neotropin®, Eldepryl®, Estrogen and Cliquinol®. In methods using simultaneous administration, the agents can be present in a combined composition or can be administered separately. Also provided are pharmaceutical compositions comprising at least one compound or pharmaceutically acceptable salt thereof described herein, and one or more additional pharmaceutical agents used in the treatment of Alzheimer's disease such as, but not limited to, Reminyl®, Cognex®, Aricept®, Exelon®, Akatinol®, Neotropin®, Eldepryl®, Estrogen and Cliquinol®. Similarly, also provided are packaged pharmaceutical compositions containing a pharmaceutical composition comprising at least one compound or pharmaceutically acceptable salt thereof described herein, and another composition comprising one or more additional pharmaceutical agents used in the treatment of Alzheimer's disease such as, but not limited to Reminyl®, Cognex®, Aricept®, Exelon®, Akatinol®, Neotropin®, Eldepryl®, Estrogen and Cliquinol®.

In another embodiment, there is provided a method for treating Celiac disease in a subject in need thereof, comprising administering a therapeutically effective amount of a compound or composition as described herein to the subject. In some embodiments, there are provided methods for treating Celiac disease comprising administering to a subject, simultaneously or sequentially, at least one compound or pharmaceutically acceptable salt thereof described herein and one or more additional agents used in the treatment of Celiac disease. In some embodiments, the at least one compound or pharmaceutically acceptable salt thereof and the one or more additional agents are present in a combined composition. In some embodiments, the at least one compound or pharmaceutically acceptable salt thereof and the one or more additional agents are administered separately. Also provided are pharmaceutical compositions comprising at least one compound or pharmaceutically acceptable salt thereof described herein and one or more additional pharmaceutical agents used in the treatment of Celiac disease. Similarly, also provided are packaged pharmaceutical compositions containing a first pharmaceutical composition comprising at least one compound or pharmaceutically acceptable salt thereof described herein, and another composition comprising one or more additional pharmaceutical agents used in the treatment of Celiac disease.

It should be understood that the methods for treating Celiac disease, as provided herein, may be useful for both prophylactic and therapeutic purposes. Evidence of therapeutic effect may be any diminution in the severity of disease, particularly diminution of the severity of such symptoms as fatigue, chronic diarrhea, malabsorption of nutrients, weight loss, abdominal distension, and anemia. Other indicators of Celiac disease include the presence of antibodies specific for glutens, antibodies specific for tissue transglutaminase, the presence of pro-inflammatory T cells and cytokines, and degradation of the villus structure of the small intestine. Application of the methods and compositions provided herein can result in the improvement of any or all of these indicators of Celiac disease. In some embodiments, subjects suitable for prophylaxis in accordance with the Celiac disease treatment methods provided herein may be identified by genetic testing for predisposition, e.g., by human leukocyte antigen (HLA) typing; by family history, and by other methods known in the art.

Multiple sclerosis (MS) is a chronic inflammatory, neurodegenerative disease that results in demyelinated lesions in the central nervous system. TG2 is upregulated in astrocytes in active MS lesions, and it has been suggested that TG2 may contribute to astrocyte adhesion and migration, and possibly glial scarring (van Strien, M. E. et al., Brain pathology, 2011, 21(1):44-54; van Strien, M. E. et al., PloS one, 2011, 6(9):e25037). Treatment of a rodent model of MS with a TG2 inhibitor dramatically lessened clinical deficits and demyelination, suggesting that TG2 inhibition may be a viable therapeutic strategy for the treatment of MS (van Strien, M. E. et al., Brain, behavior, and immunity, 2015, 50:141-154). Additional studies in a different rodent model with other TG2 inhibitors suggested that they have the potential to ameliorate MS motor deficits (Chrobok, N. L. et al., PloS one, 2018, 13(4):e0196433). In another embodiment, there is provided a method for treating MS in a subject in need thereof, comprising administering a therapeutically effective amount of a compound or composition as described herein to the subject. In some such embodiments, there are provided methods for treating MS comprising administering to a subject, simultaneously or sequentially, at least one compound or pharmaceutically acceptable salt thereof described herein and one or more additional agent used in the treatment of MS. In some embodiments, the at least one compound or pharmaceutically acceptable salt thereof and the one or more additional agents are present in a combined composition. In some embodiments, the at least one compound or pharmaceutically acceptable salt thereof and the one or more additional agents are administered separately. Also provided are pharmaceutical compositions comprising at least one compound or pharmaceutically acceptable salt thereof described herein and one or more additional pharmaceutical agent used in the treatment of MS. Similarly, also provided are packaged pharmaceutical compositions containing a first pharmaceutical composition comprising at least one compound or pharmaceutically acceptable salt thereof described herein, and another composition comprising one or more additional pharmaceutical agents used in the treatment of MS. TG2 expression has also been shown to be significantly elevated in multiple forms of central nervous system (CNS) injury, such as, for example and without limitation, traumatic brain injury (TBI), spinal cord injury (SCI) and stroke (Tolentino, P. J. et al., Journal of neurochemistry, 2002, 80(4): 579-88; Festoff, B. W. et al., Journal of neurochemistry, 2002, 81(4): 708-18; Tolentino, P. J. et al., Journal of neurochemistry, 2004, 89(5): 1301-7; Lentile, R. et al., Neuroscience letters, 2004, 363(2): 173-7). Treatment of astrocytes with an irreversible TG2 inhibitor has been shown to phenocopy the effect of TG2 deletion in a stroke model (Feola, J. et al., Brain research, 2017, 1668: 1-11). Deletion of TG2 in astrocytes resulted in a significant improvement in motor function following SCI in TG2 knockout mice, and inhibition of TG2 in wild type mice significantly improved functional recovery after SCI, similar to what was observed using the genetic model (Elahi, A. et al., Cells, 2021, 10: 2942-2957). Further, deletion of TG2 from astrocytes was shown to result in a significant attenuation of reactive gliosis after SCI (Elahi et al., 2021).

These findings suggest that TG2 inhibition may be a viable therapeutic strategy for the treatment of such disorders. In another embodiment, there is provided a method for treating CNS injury in a subject in need thereof, comprising administering a therapeutically effective amount of a compound or composition as described herein to the subject. In some such embodiments, there is provided a method for treating TBI in a subject in need thereof, comprising administering a therapeutically effective amount of a compound or composition as described herein to the subject. In some such embodiments, there is provided a method for treating SCI in a subject in need thereof, comprising administering a therapeutically effective amount of a compound or composition as described herein to the subject. In some such embodiments, there is provided a method for treating stroke in a subject in need thereof, comprising administering a therapeutically effective amount of a compound or composition as described herein to the subject. In some such embodiments. there are provided methods for treating CNS injury comprising administering to a subject, simultaneously or sequentially, at least one compound or pharmaceutically acceptable salt thereof described herein and one or more additional agent used in the treatment of the CNS injury. In some embodiments, the at least one compound or pharmaceutically acceptable salt thereof and the one or more additional agents are present in a combined composition. In some embodiments, the at least one compound or pharmaceutically acceptable salt thereof and the one or more additional agents are administered separately. Also provided are pharmaceutical compositions comprising at least one compound or pharmaceutically acceptable salt thereof described herein and one or more additional pharmaceutical agent used in the treatment of CNS injury. Similarly, also provided are packaged pharmaceutical compositions containing a first pharmaceutical composition comprising at least one compound or pharmaceutically acceptable salt thereof described herein, and another composition comprising one or more additional pharmaceutical agents used in the treatment of CNS injury.

In some embodiments, there is provided a method of inhibiting reactive gliosis in a subject in need thereof, comprising administering a therapeutically effective amount of a compound or composition as described herein to the subject. In some such embodiments, the subject suffers from or is at risk of developing a condition associated with reactive gliosis, e.g., TBI, SCI, stroke, trauma, ischemic damage, viral encephalopathy, surgery to the CNS, neuroinflammation, and/or neurodegeneration (e.g., associated with Alzheimer's disease, Parkinson's disease, mild cognitive impairment, senility, and the like). In some such embodiments, functional recovery is improved in the subject. In some such embodiments, glial scarring is reduced in the subject.

Consequently, there are provided methods for inhibition of TG2 in a subject by administering an effective amount of a compound or composition described herein. The term "subject" includes living organisms with a TG2-associated disease or disorder (e.g., a cancer, Huntington's disease, Celiac disease), or who are susceptible to or at risk of a TG2-associated disease or disorder, e.g., due to a genetic predisposition, environmental exposure to carcinogens, and the like. Examples of subjects include humans, monkeys, cows, rabbits, sheep, goats, pigs, dogs, cats, rats, mice, and transgenic species thereof. The term "subject" generally includes animals susceptible to states mediated by TG2, such as without limitation cancer and/or tumor growth, e.g., mammals, e.g. primates, e.g. humans. The animal can also be an animal model for a disorder, e.g., a cancer mouse model, a xenograft recipient, and the like.

In some embodiments, a subject is in need of treatment by the methods provided herein and is selected for treatment based on this need. A subject in need of treatment is art-recognized, and includes subjects that have been identified as having a disease or condition (e.g., cancer, e.g., having a tumor or a cancerous growth), or having a symptom of such a disease or condition, or being at risk of such a disease or condition, and would be expected, based on diagnosis, e.g., medical diagnosis, to benefit from treatment (e.g., curing, healing, preventing, alleviating, relieving, altering, remedying, ameliorating, improving, or affecting the disease or disorder, the symptom of the disease or disorder, or the risk of the disease or disorder).

As used herein, "treating" or "treatment" of a disease or condition refers, in some embodiments, to ameliorating at least one disease or condition (i.e., arresting or reducing the development of a disease or condition or at least one of the clinical symptoms thereof). In certain embodiments "treating" or "treatment" refers to ameliorating at least one physical parameter, such as e.g. tumor size, growth, or migration. In certain embodiments, "treating" or "treatment" refers to inhibiting or improving a disease or condition, either physically (e.g., stabilization of a discernible symptom), physiologically (e.g., stabilization of a physical parameter), or both. In certain embodiments, "treating" or "treatment" refers to delaying the onset (or recurrence) of a disease or condition. The term "treating" or "treatment" may refer to any indicia of success in the treatment or amelioration of a disease or condition, including any objective or subjective parameter such as abatement; remission; diminishing of symptoms or making the disease or condition more tolerable to the subject; improving a subject's physical or mental well-being, such as reducing pain experienced by the patient; and, in some situations additionally improving at least one parameter of a disease or condition, such as, for example and without limitation, reducing tumor growth rate, reducing tumor volume, reducing or slowing tumor migration, invasion, and/or metastasis, overcoming chemoresistance, increasing sensitivity to chemotherapies, slowing migration, reducing cancer stem cell proliferation, and the like.

As used herein, "preventing" or "prevention" is intended to refer at least to the reduction of the likelihood of, or the risk of, or susceptibility to acquiring a disease or disorder (i.e., causing at least one of the clinical symptoms of the disease not to develop in a patient that may be exposed to or predisposed to or at risk of the disease but does not yet experience or display symptoms of the disease). The term "prevention" or "preventing" is also used to describe the administration of a compound or composition described herein to a subject who is at risk of (or susceptible to) such a disease or condition. Subjects amenable to treatment for prevention of a disease or condition include individuals at risk of the disease or condition but not showing symptoms, as well as patients presently showing symptoms. In some embodiments, "prevention" or "preventing" is used to describe the administration of a compound or composition described herein to a subject who has been diagnosed with or treated for a disease or condition and is at risk of recurrence of the disease or condition.

In some embodiments, treatment or prevention are within the context of the present invention if there is a measurable difference between the performances of subjects treated using the compounds and methods provided herein as compared to members of a placebo group, historical control, or between subsequent tests given to the same subject.

The term "inhibition" or "inhibiting" is used herein to refer generally to reducing, slowing, restricting, delaying, suppressing, blocking, hindering, or preventing a process, such as without limitation reducing or slowing growth, spread or survival of e.g., a cancer, e.g., a tumor.

The term "effective amount" as used herein means that amount or dose of a compound or composition, upon single or multiple dose administration to a subject, which provides the desired effect (e.g., the desired biological or medicinal response, e.g., to ameliorate, lessen or prevent a disease, disorder or condition) in the subject being treated. In some embodiments, an effective amount is an amount or dose of a compound or composition that prevents or treats a TG2-associated disease or disorder in a subject, as described herein. In some embodiments, an effective amount is an amount or dose of a compound or composition that inhibits one or more activity of TG2 in a subject, as described herein. The terms "effective amount" and "therapeutically effective amount" are used interchangeably herein.

It should be understood that the dosage or amount of a compound and/or composition used, alone or in combination with one or more active compounds to be administered, depends on the individual case and is, as is customary, to be adapted to the individual circumstances to achieve an optimum effect. Dosing and administration regimens are within the purview of the skilled artisan, and appropriate doses depend upon a number of factors within the knowledge of the ordinarily skilled physician, veterinarian, or researcher (e.g., see Wells et al. eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif (2000)). For example, dosing and administration regimens depend on the nature and the severity of the disorder to be treated, and also on the sex, age, weight and individual responsiveness of the human or animal to be treated, on the efficacy and duration of action of the compounds used, on whether the therapy is acute or chronic or prophylactic, and/or on whether other active compounds are administered in addition to the therapeutic molecule(s).

Thus the dose(s) of a compound or composition will vary depending upon a variety of factors including, but not limited to: the activity, biological and pharmacokinetic properties and/or side effects of the compound being used; the age, body weight, general health, gender, and diet of the subject; the time of administration, the route of administration, the rate of excretion, and any drug combination, if applicable; the effect which the practitioner desires the compound to have upon the subject; and the properties of the compound being administered (e.g. bioavailability, stability, potency, toxicity, etc). Such appropriate doses may be determined as known in the art. When one or more of the compounds of the invention is to be administered to humans, a physician may for example, prescribe a relatively low dose at first, subsequently increasing the dose until an appropriate response is obtained.

There are no particular limitations on the dose of each of the compounds for use in compositions provided herein. Exemplary doses include milligram or microgram amounts of the compound per kilogram of subject or sample weight (e.g., about 50 micrograms per kilogram to about 500 milligrams per kilogram, about 1 milligram per kilogram to about 100 milligrams per kilogram, about 1 milligram per kilogram to about 50 milligrams per kilogram, about 1 milligram per kilogram to about 10 milligrams per kilogram, or about 3 milligrams per kilogram to about 5 milligrams per kilogram). Additional exemplary doses include doses of about 5 to about 500 mg, about 25 to about 300 mg, about 25 to about 200 mg, about 50 to about 150 mg, or about 50, about 100, about 150 mg, about 200 mg or about 250 mg, and, for example, daily or twice daily, or lower or higher amounts.

In some embodiments, the dose range for adult humans is generally from 0.005 mg to 10 g/day orally. Tablets or other forms of presentation provided in discrete units may conveniently contain an amount of a compound (e.g., of Formula I or Formula II) which is effective at such dosage or as a multiple of the same, for instance, units containing 5 mg to 500 mg, usually around 10 mg to 200 mg. A dosage unit (e.g., an oral dosage unit) can include from, for example, 1 to 30 mg, 1 to 40 mg, 1 to 100 mg, 1 to 300 mg, 1 to 500 mg, 2 to 500 mg, 3 to 100 mg, 5 to 20 mg, 5 to 100 mg (e.g. 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, or 500 mg) of a compound described herein.

Administration of compounds and compositions provided herein can be carried out using known procedures, at dosages and for periods of time effective to achieve a desired purpose. Dosage regimens can be adjusted to provide the optimum therapeutic response. For example, several divided doses may be administered daily, or the dose may be proportionally reduced as indicated by the exigencies of the therapeutic situation. In some embodiments, a compound or composition is administered at an effective dosage sufficient to prevent or treat a TG2-associated disease or disorder, e.g., a cancer, in a subject. Further, a compound or composition may be administered using any suitable route or means, such as without limitation via oral, parenteral, intravenous, intraperitoneal, intramuscular, sublingual, topical, or nasal administration, via inhalation, or via such other routes as are known in the art.

Without intending to be limited by theory, the present inventors contemplate that the therapeutic benefits of inhibiting one or more activity of TG2 including without limitation GTP binding, GTPase activity, deamidation activity, and/or transamidation activity, may be mediated in some embodiments by: sensitizing refractory cancer cells to chemotoxic agents; overcoming cancer cell resistance to chemotherapy; preventing or inhibiting cancer stem cell (CSC) survival and/or proliferation; preventing or inhibiting CSC spheroid formation; preventing or inhibiting cancer recurrence, e.g., recurrence after a therapy such as surgical excision; and/or preventing or inhibiting metastasis, e.g., the EMT transition. In some embodiments, cancer (e.g., tumor)

progression, growth, migration, and/or invasion is prevented or inhibited. In some embodiments, invasion of cancer cells, e.g., malignant glial cells or GBM cells, is prevented or inhibited. In an embodiment, recurrence of a cancer after treatment, e.g., after surgical excision, is inhibited. For example, malignant glioma invasion is a primary cause of brain cancer treatment failure. In some embodiments malignant glial cell (MGC) invasion is inhibited, thereby reducing or delaying the cancer invasion into adjacent healthy tissues, such as the brain in the case of glioma. In an embodiment, progression of a cancer is inhibited.

Kits

Compound and compositions provided herein may be packaged as part of a kit, optionally including a container (e.g. packaging, a box, a vial, etc). The kit may be commercially used according to the methods described herein and may include instructions for use in such methods. Additional kit components may include acids, bases, buffering agents, inorganic salts, solvents, antioxidants, preservatives, or metal chelators. The additional kit components may be present as pure compositions, or as aqueous or organic solutions that incorporate one or more additional kit components. Any or all of the kit components optionally further comprise buffers.

EXAMPLES

The present invention will be more readily understood by referring to the following examples, which are provided to illustrate the invention and are not to be construed as limiting the scope thereof in any manner.

Unless defined otherwise or the context clearly dictates otherwise, all technical and scientific terms used herein have the same meaning as commonly understood by one of ordinary skill in the art to which this invention belongs. It should be understood that any methods and materials similar or equivalent to those described herein can be used in the practice or testing of the invention.

Example 1. Design and Synthesis of TG2 Inhibitor Compounds

Previously we described targeted covalent inhibitors of TG2 designed to react with the enzyme active site of the open conformation, preventing it thereafter from adopting its closed conformation, thus abolishing GTP binding (see WO 2017/179018, issued as U.S. Pat. No. 10,894,777). Examples of the inhibitor compounds described previously include NC9, VA4, and AA9, as shown here:

NC9

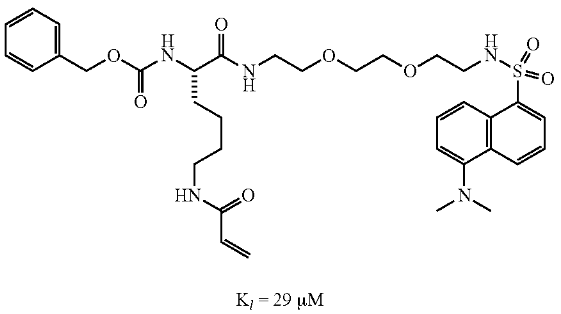

$K_I$ = 29 μM
$k_{inact}$ = 0.41 $min^{-1}$
$k_{inact}/K_I$ = 14 × $10^3$ $M^{-1}min^{-1}$ -continued

VA4

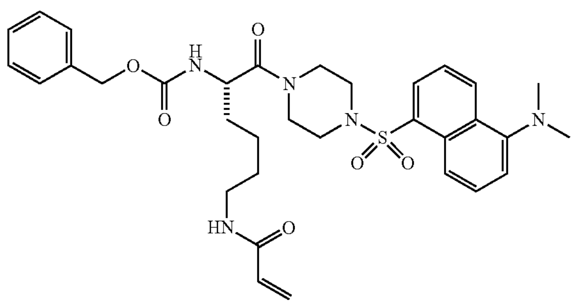

$K_I$ = 3.8 μM
$k_{inact}$ = 0.38 $min^{-1}$
$k_{inact}/K_I$ = 100 × $10^3$ $M^{-1}min^{-1}$

AA9

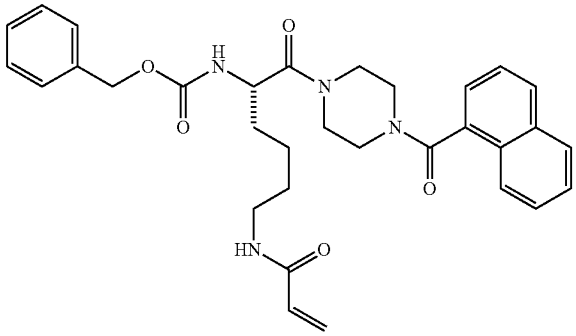

$K_I$ = 4.8 μM
$k_{inact}$ = 1.2 $min^{-1}$
$k_{inact}/K_I$ = 244 × $10^3$ $M^{-1}min^{-1}$ In our previous studies we identified AA9 as a strong TG2 inhibitor. In the present work, under experimental conditions used herein, we measured a $k_{inact}/K_I$ of 244±75×$10^3$ $M^{-1}$ $min^{-1}$ for AA9.

Starting with AA9 as a benchmark inhibitor, we have studied the effect of the N-terminal functional group on the efficiency (e.g., affinity, reactivity) of TG2 inhibitor compounds. To do so, we synthesized and tested a series of compounds with different structures at the N-terminal.

First, we planned a synthetic route that would provide a common intermediate (amine 11) amenable to late-stage diversification. The synthesis of the key intermediate amine 11 is shown in Scheme 1. Briefly, this amine was prepared by first making naphthoyl piperazine 4 and reacting it with the NHS ester 6—a lysine derivative, whose alpha amino group was protected with a Boc and whose epsilon amino group was protected with a Cbz. The resulting peptidomimetic 7 was then selectively deprotected to give amine 8, whose epsilon amino group was reacted with acryloyl chloride to give amide 10. This Boc-protected derivative could be prepared in large quantity and was very stable. Removal of the Boc group is facile, giving amine 11 that could be subsequently diversified broadly, to provide different classes of inhibitors for testing.

Amine 11 was modified as described below to provide heteroaryl, alkyl carbonyl, aryl, arylalkyl, and sulfonamide derivative compounds for testing.

Scheme 1 Synthesis of key intermediate amine 11.
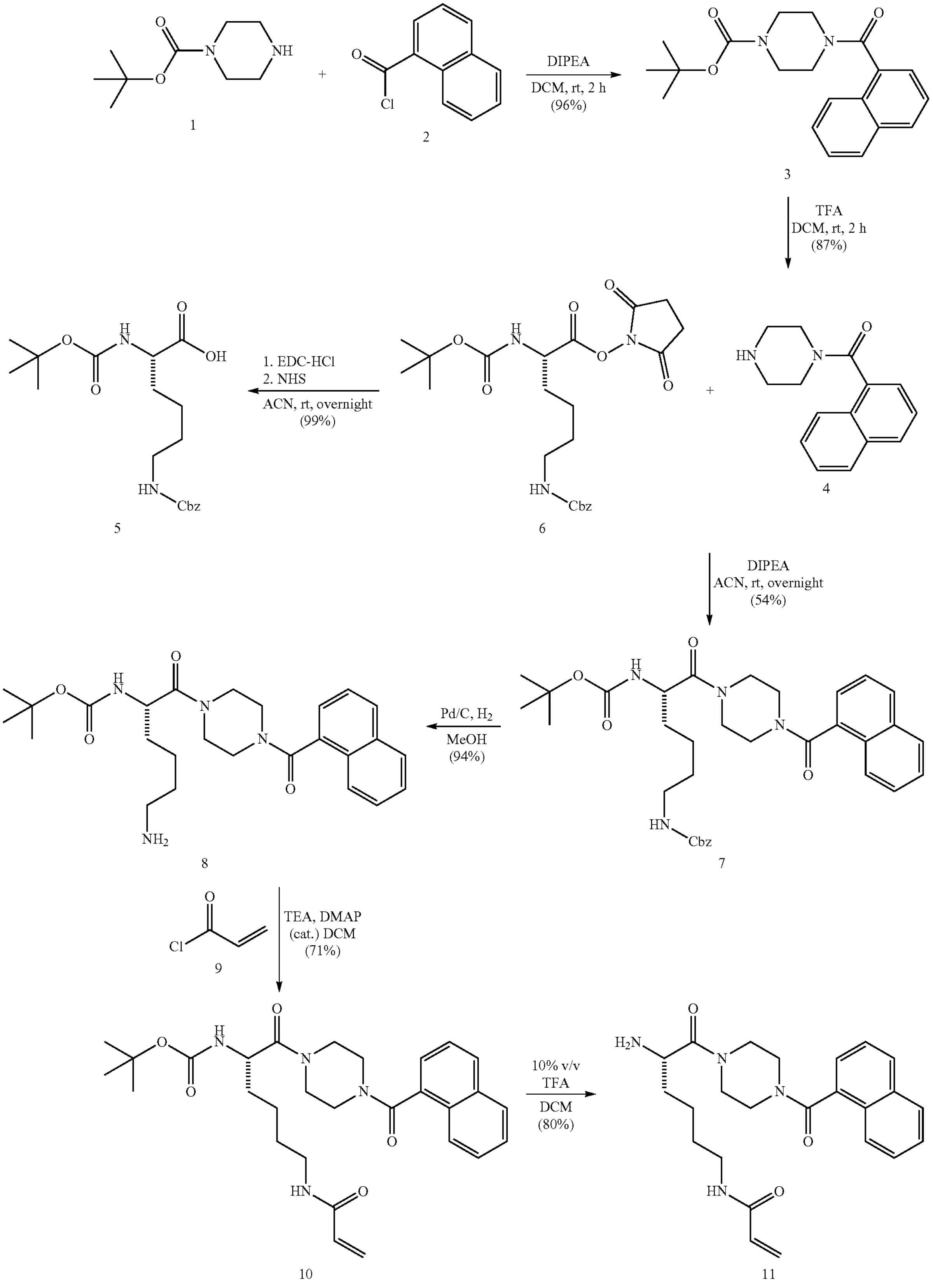

Heteroaryl compounds (18-23). Commercially available heteroaryl carboxylic acids were transformed into their NHS esters and coupled with amine 11 to give inhibitors 18-23, as shown in Scheme 2.

Scheme 2 Acylation of amine 11 to give heteroaryl inhibitors 18-23.

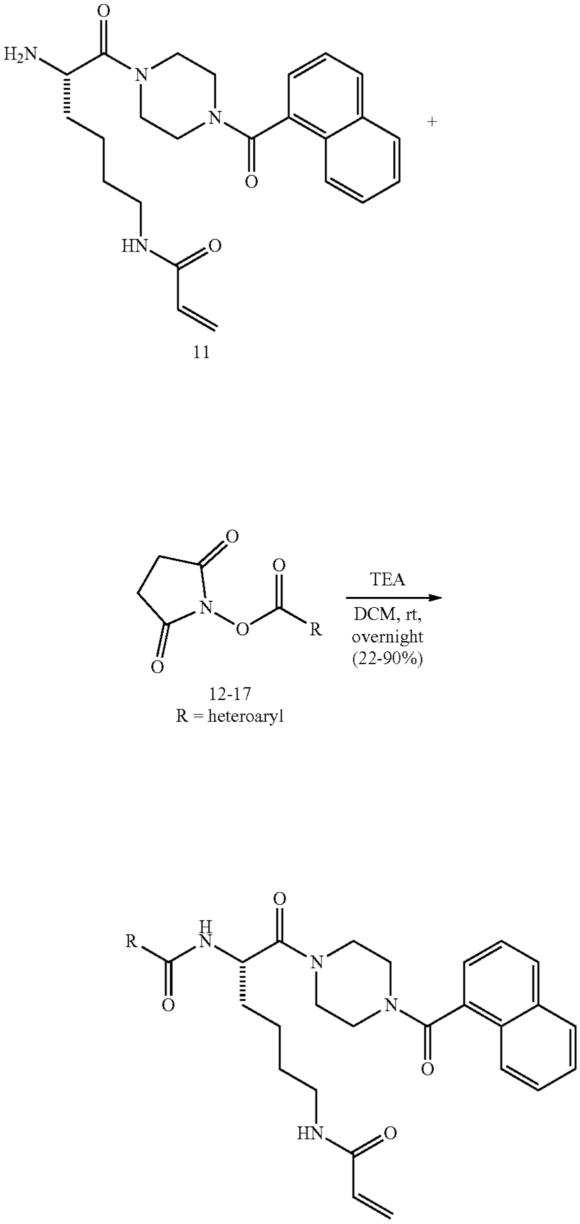

11

12-17
R = heteroaryl 18-23

Alkyl carbonyl compounds (33-41). A series of commercially available alkyl carboxylic acids were transformed into their NHS esters, acid chlorides or anhydrides, which were coupled with amine 11 to give inhibitors 33-41, as shown in Scheme 3.

Scheme 3 Acylation of amine 11 to give alkyl inhibitors 33-41.

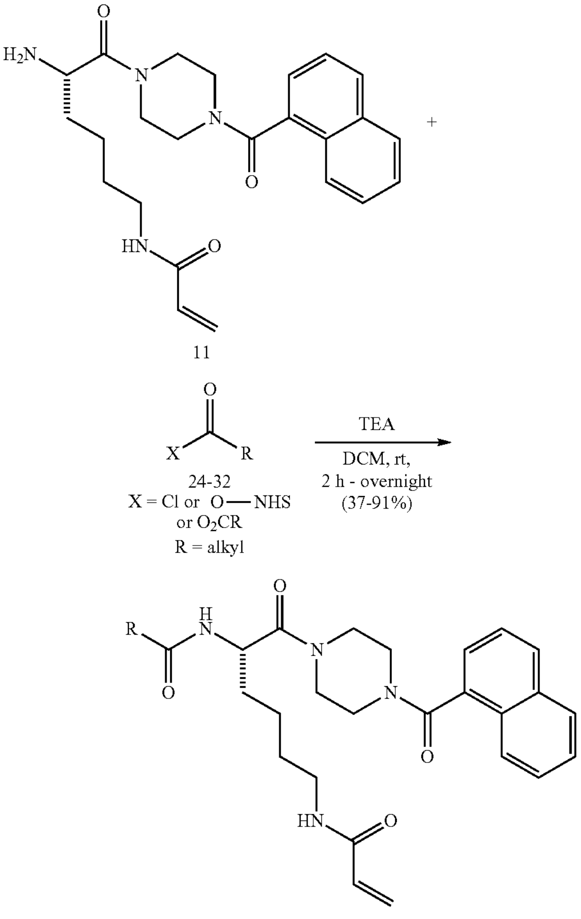

11

24-32
X = Cl or O—NHS
or $O_2CR$
R = alkyl 33-41

Aryl and arylalkyl compounds (61-81). Synthesis of aryl and alkylaryl N-terminal derivatives was achieved by transforming commercially available alkyl and alkylaryl carboxylic acids into the corresponding NHS esters or acid chlorides 2, 42-60. The activated intermediates were then coupled to amine 11 with triethylamine to yield aryl and alkylaryl inhibitors 61-81, as shown in Scheme 4.

Scheme 4 Acylation of amine 11 to give aryl and arylalkyl inhibitors 61-81.

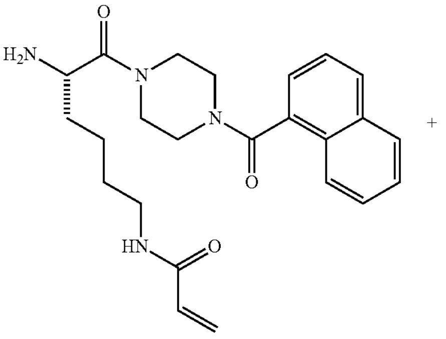

11

-continued

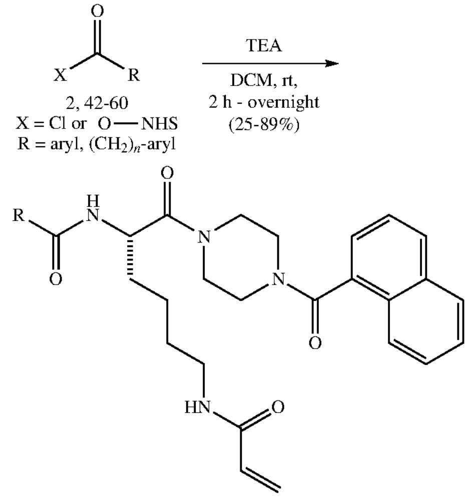

61-81

Sulfonamide compounds (87-91). To produce inhibitors spaced by a sulfonamide on the N-terminus, commercially available sulfonyl chlorides 82-86 were coupled to key intermediate amine 11. The sulfonamide coupling with triethylamine yielded inhibitors 87-91, as shown in Scheme 5.

Scheme 5 Sulfonylation of amine 11 to give sulfonamide inhibitors 87-91.

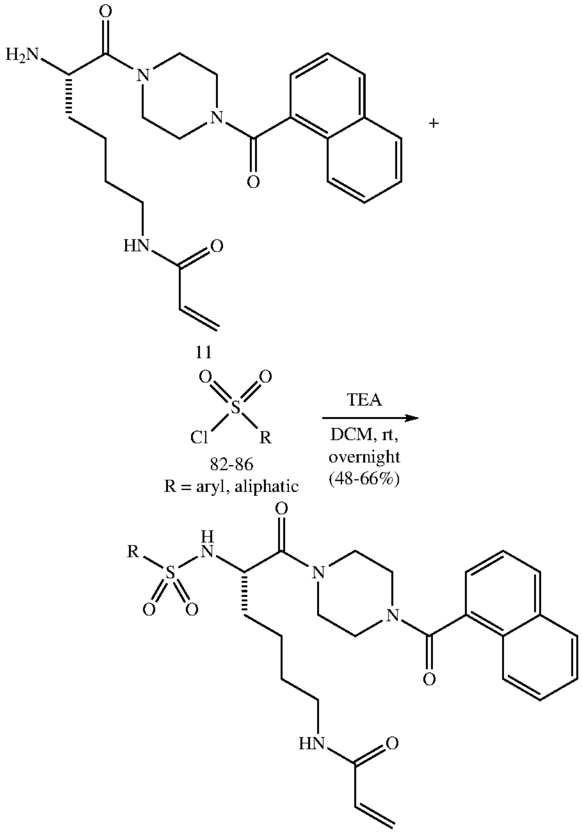

87-91

Example 2. Characterization of TG2 Inhibitor Compounds

The ability of the compounds to inhibit TG2 transamidase activity and the kinetics of TG2 inhibition were investigated using a colorimetric activity assay, as follows:

Colorimetric transamidase activity assay. The activities of hTG1, hTG2 and hTG6 were measured via a colorimetric assay using the chromogenic substrate Cbz-Glu(γ-p-nitrophenyl ester)Gly (AL5), as described (Leblanc, A. et al., "Kinetic studies of guinea pig liver transglutaminase reveal a general-base-catalyzed deacylation mechanism." Biochemistry 2001, 40 (28), 8335-8342). Assays were conducted at 25° C. in 50 mM MOPS buffer (pH 6.95) containing 7.5 mM $CaCl_2$. Enzymatic inhibition assays were run under Kitz & Wilson conditions established for each transglutaminase isoform by varying the concentration of substrate to be 112 μM, 100 μM, and 436 μM of AL5 for hTG1, hTG2, and hTG6, respectively (Akbar, A. et al., "Structure-Activity Relationships of Potent, Targeted Covalent Inhibitors That Abolish Both the Transamidation and GTP Binding Activities of Human Tissue Transglutaminase." *J. Med. Chem.* 2017, 60 (18), 7910-7927; Kitz, R. and Wilson, I. B., "Esters of methanesulfonic acid as irreversible inhibitors of acetylcholinesterase." *J. Biol. Chem.* 1962, 237, 3245-49). The substrate AL5 was prepared in as a stock solution in DMSO such that the final concentration of this co-solvent was constant at 2.5% v/v. Stock solutions of the inhibitors were made in water ranging in concentration from 100-500 μM. The reaction was initiated with the addition of enzyme, 0.10 μM hTG1, 0.25 μM hTG2 (4.6 mU/mL) or 0.32 μM hTG6. Formation of hydrolysis product, p-nitrophenolate (pNP), was monitored at 405 nm in a polystyrene 96-well microplate using a BioTek Synergy 4 plate reader. The observed first-order rate constants of inactivation ($k_{obs}$) were determined via non-linear regression fit to a mono-exponential model (Eqn 1) of absorbance versus time curves. These rate constants ($k_{obs}$) were in turn fit to a saturation kinetics model (Eqn 2), by non-linear regression, providing the kinetic parameters $k_{inact}$ and $K_I$, as previously described by Stone and Hofsteenge (Stone, S. R. and Hofsteenge, J., "Specificity of activated human protein C." *Biochem. J.* 1985, 230 (2), 497-502). A double reciprocal plot of Eqn 2 was applied when the observed rate constant of inactivation ($k_{obs}$) did not demonstrate saturation at high inhibitor concentrations, or when inhibitor solubility was limiting. Experiments were completed in triplicate at minimum.

$$f(pNP) = [pNP]_0 + (\text{Plateau} - [pNP]_0)\left(1 - e^{(k_{obs}t)}\right) \quad \text{(Eqn 1)}$$

$$k_{obs} = \frac{k_{inact}[I]}{[I] + K_I\left(1\frac{[S]}{K_M}\right)} \quad \text{(Eqn 2)}$$

All compounds tested showed time-dependent inhibition of TG2, as observed during the reaction of TG2 with its chromogenic substrate AL5 (i.e., Kitz and Wilson conditions). Fitting of this time-dependent inactivation to a mono-exponential equation gave first-order rate constants, $k_{obs}$. The dependence of $k_{obs}$ on the concentration of inhibitor showed saturation behaviour; for almost all test compounds, these data could be fitted to a hyperbolic equation, to provide the kinetic parameters of $K_I$ (inhibition constant) and $k_{inact}$ (rate constant of inactivation). In some cases, the kinetic data were fitted to a linear double reciprocal equation. However, in a few cases it was not possible to test the compound at high enough concentrations to observe saturation behaviour; in these cases, the linear slope of $k_{obs}$ vs [I] was measured to give the ration $k_{inact}/K_I$. Kinetic parameters are shown in Tables 1-5.

TABLE 1

Kinetic parameters of N-terminal heteroaryl inhibitor compounds.

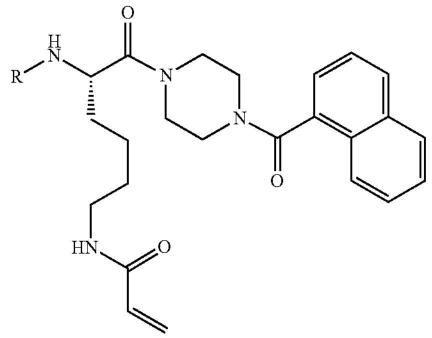

| Inhibitor | R group | $K_I$ (μM) | $k_{inact}$ ($min^{-1}$) | $k_{inact}/K_I$ ($10^3$ $M^{-1}$ $min^{-1}$) |
|---|---|---|---|---|
| 18 | 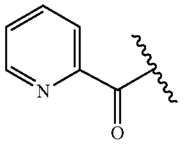 [SMILES: *C(=O)c1ccccn1] | 41.4 ± 3.8* | 0.39 ± 0.04* | 9.6 ± 0.2* |
| 19 | 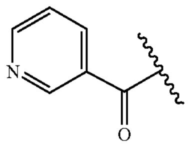 [SMILES: *C(=O)c1cccnc1] | 25.4 ± 2.8* | 0.59 ± 0.07* | 23.3 ± 0.8* |
| 20 | 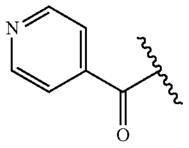 [SMILES: *C(=O)c1ccncc1] | 19.3 ± 4.3* | 0.24 ± 0.05* | 12.7 ± 1.1* |

TABLE 1-continued

Kinetic parameters of N-terminal heteroaryl inhibitor compounds.

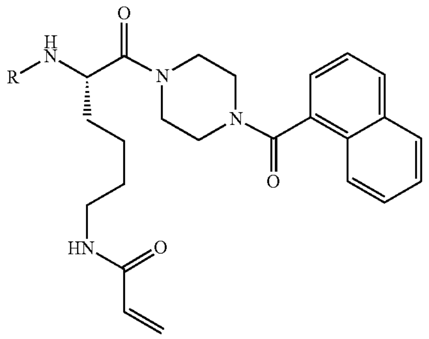

| Inhibitor | R group | $K_I$ (μM) | $k_{inact}$ ($min^{-1}$) | $k_{inact}/K_I$ ($10^3$ $M^{-1}$ $min^{-1}$) |
|---|---|---|---|---|
| 21 | 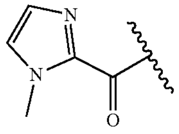 [SMILES: *C(=O)c1nccn1C] | 15.7 ± 4.5 | 0.18 ± 0.03 | 11.5 ± 3.8 |
| 22 | 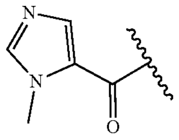 [SMILES: *C(=O)c1cncn1C] | 22.3 ± 5.0 | 0.28 ± 0.04 | 12.6 ± 3.4 |
| 23 | 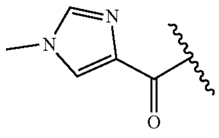 [SMILES: *C(=O)c1cn(C)cn1] | 28.7 ± 5.9 | 0.46 ± 0.06 | 16.0 ± 4.0 |

*values determined using a double-reciprocal analysis

TABLE 2
Kinetic parameters of N-terminal alkyl inhibitors.
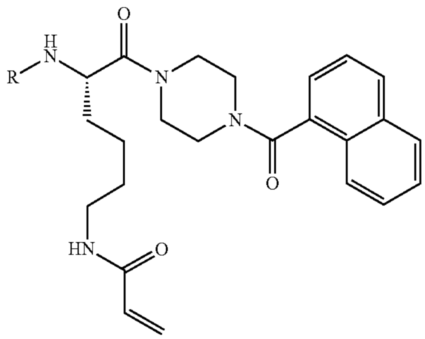
| Inhibitor | R group | $K_I$ (μM) | $k_{inact}$ ($min^{-1}$) | $k_{inact}/K_I$ ($10^3$ $M^{-1}$ $min^{-1}$) |
|---|---|---|---|---|
| 33 | 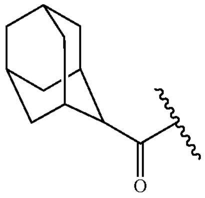 [SMILES: *C(=O)C1C2CC3CC(C2)CC1C3] | 15.3 ± 0.3 | 0.23 ± 0.03 | 14.9 ± 4.2 |
| 34 | 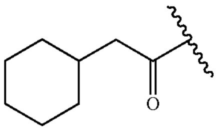 [SMILES: *C(=O)CC1CCCCC1] | 12.2 ± 2.4 | 0.26 ± 0.04 | 20.9 ± 4.9 |
| 35 | 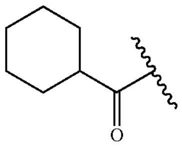 [SMILES: *C(=O)C1CCCCC1] | 9.9 ± 1.3 | 0.33 ± 0.02 | 33.6 ± 4.9 |
| 36 | 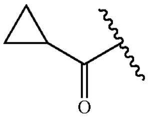 [SMILES: *C(=O)C1CC1] | 10.6 ± 3.6 | 1.02 ± 0.23 | 96.6 ± 39.8 |
| 37 | 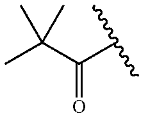 [SMILES: *C(=O)C(C)(C)C] | 8.8 ± 3.6 | 0.49 ± 0.13 | 56.2 ± 27.0 |
| 38 | 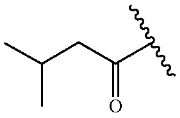 [SMILES: *C(=O)CC(C)C] | 9.7 ± 1.9 | 0.64 ± 0.07 | 66.7 ± 15.4 |
| 39 | 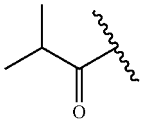 [SMILES: *C(=O)C(C)C] | 9.9 ± 1.4 | 0.65 ± 0.05 | 65.1 ± 10.6 |
| 40 | 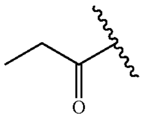 [SMILES: *C(=O)CC] | 5.1 ± 1.0 | 0.53 ± 0.05 | 103 ± 22.3 |

TABLE 2-continued

Kinetic parameters of N-terminal alkyl inhibitors.

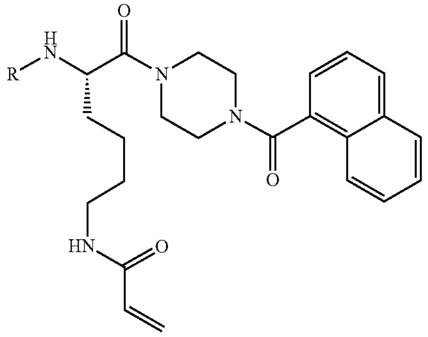

| Inhibitor | R group | $K_I$ (μM) | $k_{inact}$ ($min^{-1}$) | $k_{inact}/K_I$ ($10^3$ $M^{-1}$ $min^{-1}$) |
|---|---|---|---|---|
| 41 | 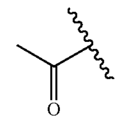 [SMILES: *C(C)=O] | 33.0 ± 14.5* | 1.45 ± 0.64* | 44.1 ± 1.8* |

*values determined using a double-reciprocal analysis

TABLE 3

Kinetic parameters of N-terminal aryl inhibitors.

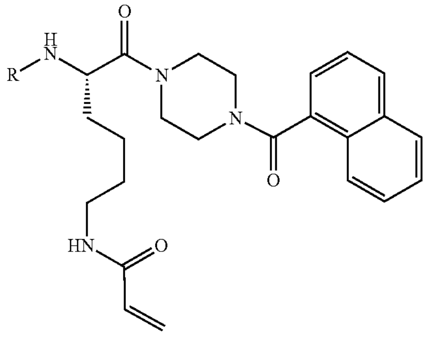

| Inhibitor | R group | $K_I$ (μM) | $k_{inact}$ ($min^{-1}$) | $k_{inact}/K_I$ ($10^3$ $M^{-1}$ $min^{-1}$) |
|---|---|---|---|---|
| 61 | 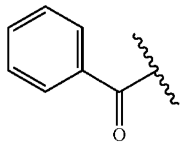 [SMILES: *C(=O)c1ccccc1] | 27.6 ± 8.1<br>12.0 ± 2.8* | 1.34 ± 0.31<br>0.71 ± 0.16* | 48.4 ± 18.1<br>59.0 ± 3.4* |
| 62 | 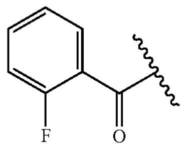 [SMILES: *C(=O)c1ccccc1F] | 10.0 ± 2.6 | 0.39 ± 0.06 | 39.4 ± 11.8 |
| 63 | 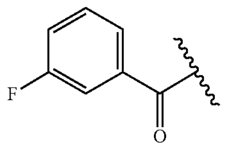 [SMILES: *C(=O)c1cccc(F)c1] | 13.4 ± 3.5<br>9.9 ± 3.1* | 0.64 ± 0.11<br>0.51 ± 0.16* | 47.8 ± 15.2<br>51.6 ± 4.7* |

TABLE 3-continued

Kinetic parameters of N-terminal aryl inhibitors.

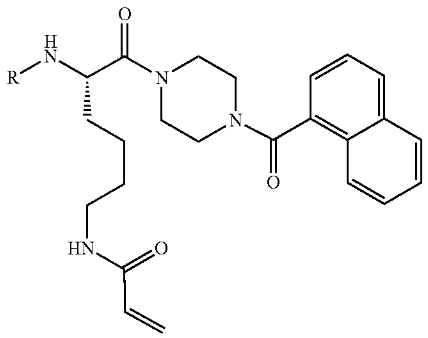

| Inhibitor | R group | $K_I$ (μM) | $k_{inact}$ ($min^{-1}$) | $k_{inact}/K_I$ ($10^3$ $M^{-1}$ $min^{-1}$) |
|---|---|---|---|---|
| 64 | 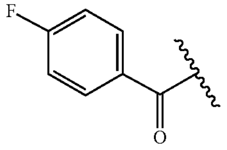 [SMILES: *C(=O)c1ccc(F)cc1] | 16.2 ± 7.5<br>11.6 ± 2.8* | 0.90 ± 0.3<br>0.70 ± 0.2* | 55.4 ± 31.9<br>60.6 ± 3.9* |
| 65 | 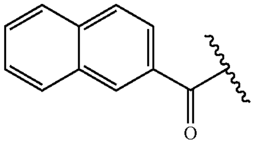 [SMILES: *C(=O)c1ccc2ccccc2c1] | 8.0 ± 1.8 | 0.29 ± 0.03 | 36.5 ± 9.1 |
| 66 | 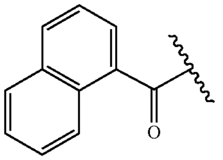 [SMILES: *C(=O)c1cccc2ccccc12] | 20.3 ± 5.1<br>9.3 ± 1.0* | 0.41 ± 0.06<br>0.26 ± 0.03* | 20.1 ± 5.9<br>27.5 ± 1.2* |

*values determined using a double-reciprocal analysis

TABLE 4

Kinetic parameters of select N-terminal arylalkyl inhibitors.

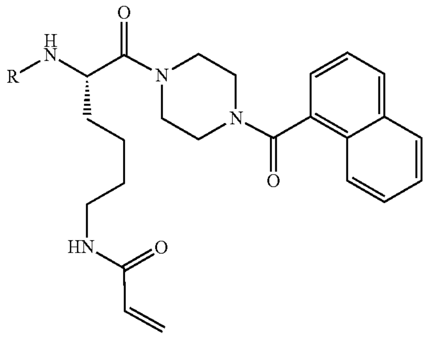

| Inhibitor | R group | $K_I$ (μM) | $k_{inact}$ ($min^{-1}$) | $k_{inact}/K_I$ ($10^3$ $M^{-1}$ $min^{-1}$) |
|---|---|---|---|---|
| 67 | 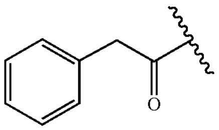 [SMILES: *C(=O)Cc1ccccc1] | 4.1 ± 0.5 | 1.03 ± 0.06 | 250 ± 31.8 |

TABLE 4-continued
Kinetic parameters of select N-terminal arylalkyl inhibitors.
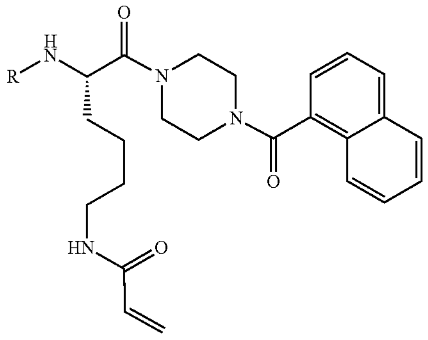
| Inhibitor | R group | $K_I$ (μM) | $k_{inact}$ ($min^{-1}$) | $k_{inact}/K_I$ ($10^3$ $M^{-1}$ $min^{-1}$) |
|---|---|---|---|---|
| 68 | 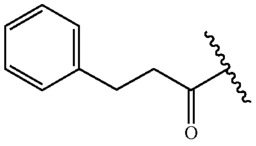 [SMILES: *C(=O)CCc1ccccc1] | 2.8 ± 0.3 | 0.60 ± 0.04 | 214 ± 28.4 |
| 69 | 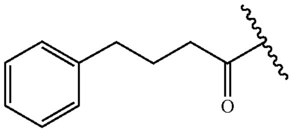 [SMILES: *C(=O)CCCc1ccccc1] | 5.3 ± 0.6 | 0.21 ± 0.01 | 39.6 ± 4.9 |
| 70 | 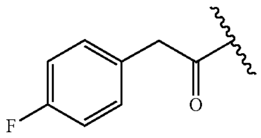 [SMILES: *C(=O)Cc1ccc(F)cc1] | 4.2 ± 0.9 | 0.49 ± 0.06 | 119 ± 28.9 |
| 71 | 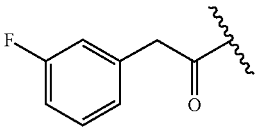 [SMILES: *C(=O)Cc1cccc(F)c1] | 4.9 ± 0.5 | 0.75 ± 0.05 | 155 ± 20.3 |
| 72 | 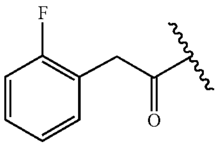 [SMILES: *C(=O)Cc1ccccc1F] | 1.0 ± 0.2 | 0.46 ± 0.03 | 443 ± 88.4 |
| 73 | 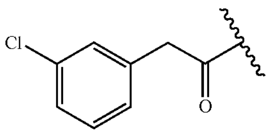 [SMILES: *C(=O)Cc1cccc(Cl)c1] | 1.0 ± 0.5 | 0.30 ± 0.07 | 290 ± 146 |
| 74 | 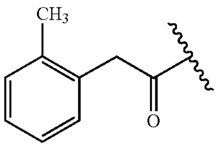 | 6.1 ± 1.8 | 2.1 ± 0.5 | 352 ± 128 |

TABLE 4-continued
Kinetic parameters of select N-terminal arylalkyl inhibitors.
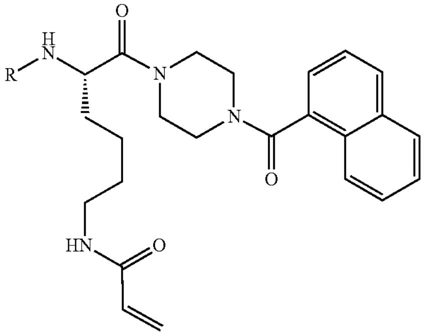
| Inhibitor | R group | $K_I$ (μM) | $k_{inact}$ ($min^{-1}$) | $k_{inact}/K_I$ ($10^3$ $M^{-1}$ $min^{-1}$) |
|---|---|---|---|---|
| 75 | 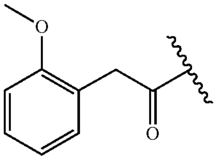 [SMILES: *C(=O)Cc1ccccc1OC] | 4.6 ± 2.9 | 1.4 ± 0.6 | 299 ± 228 |
| 76 | 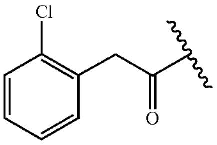 | 18.0 ± 6.9 | 5.3 ± 1.8 | 295 ± 151 |
| 77 | 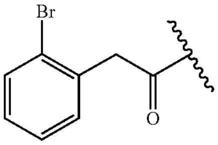 [SMILES: *C(=O)Cc1ccccc1Br] | 9.8 ± 1.5 | 3.1 ± 0.4 | 310 ± 60 |
| 78 | 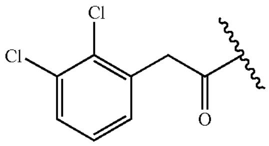 [SMILES: *C(=O)Cc1cccc(Cl)c1Cl] | 2.7 ± 2.8 | 0.46 ± 0.34 | 170 ± 214 |
| 79 | 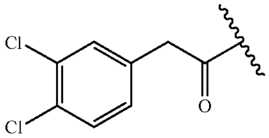 [SMILES: *C(=O)Cc1ccc(Cl)c(Cl)c1] | 0.58 ± 0.30 | 0.08 ± 0.02 | 131 ± 73 |
| 80 | 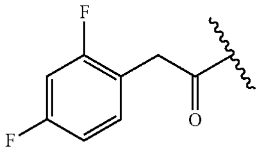 [SMILES: *C(=O)Cc1ccc(F)cc1F] | 2.8 ± 0.9 | 0.62 ± 0.09 | 224 ± 78.9 |
| 81 | 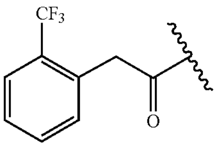 [SMILES: *C(=O)Cc1ccccc1C(F)(F)F] | 10.1 ± 3.1 | 1.0 ± 0.3 | 100 ± 39 |
*values determined using a double-reciprocal analysis

TABLE 5

Kinetic parameters of N-terminal sulfonyl irreversible inhibitors.

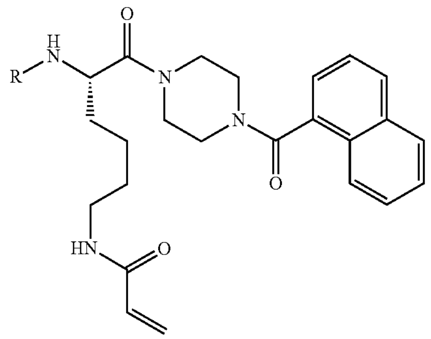

| Inhibitor | R group | $K_I$ (μM) | $k_{inact}$ ($min^{-1}$) | $k_{inact}/K_I$ ($10^3$ $M^{-1}$ $min^{-1}$) |
|---|---|---|---|---|
| 87 | 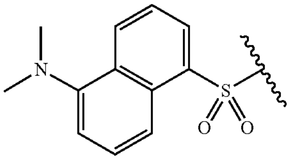 [SMILES: *S(=O)(=O)c1cccc2c(N(C)C)cccc12] | n.d | n.d. | n.d. |
| 88 | 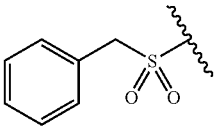 [SMILES: *S(=O)(=O)Cc1ccccc1] | 46.7 ± 10.2 | 0.53 ± 0.09 | 11.4 ± 3.1 |
| 89 | 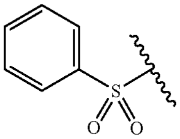 [SMILES: *S(=O)(=O)c1ccccc1] | 88.8 ± 6.7* | 0.63 ± 0.05* | 7.1 ± 1.3* |
| 90 | 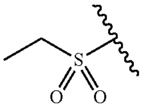 [SMILES: *S(=O)(=O)CC] | 26.6 ± 1.1 | 0.83 ± 0.02 | 31.1 ± 1.6 |
| 91 | 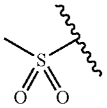 [SMILES: *S(C)(=O)=O] | 25.3 ± 7.1 | 0.57 ± 0.11 | 22.6 ± 7.8 |

*values determined using a double-reciprocal analysis
n.d. = No detectable inhibition

Example 3. GTP Binding Inhibition

Previously we proposed a mechanism of action for the NC9, VA4 and AA9 inhibitors based on their ability to react covalently with the open conformation of TG2, locking the enzyme in that conformation and thereby abolishing the enzyme's ability to bind GTP and act as a G-protein. We showed that VA4 and AA9 can suppress the ability of TG2 to bind GTP-γ-S-FL BODIPY, a non-hydrolysable fluorescent GTP analogue, whose fluorescence increases when it is bound by protein (McEwen, D. P. et al., "Fluorescent BODIPY-GTP analogs: Real-time measurement of nucleotide binding to G proteins." *Anal. Biochem.* 2001, 291 (1), 109-117). We used the same in vitro GTP binding assay to measure the ability of representative phenylacetyl inhibitors 67 and 72 to abolish GTP binding, as follows:

In vitro GTP binding assay. GTP binding was measured using a method similar to that reported previously (McEwen, D. P. et al., "Fluorescent BODIPY-GTP analogs: Real-time measurement of nucleotide binding to G proteins." Anal. Biochem. 2001, 291 (1), 109-117). For all experiments, GTP binding was measured using 3 μM of the fluorescent, non-hydrolysable GTP analogue BODIPY GTP-γ-S(Invitrogen), whose fluorescence increases when bound by protein. hTG2 (8-10 μg) was incubated at 25° C. for 30 minutes with or without irreversible inhibitor (2×$K_I$) with 3.0 mM $CaCl_2$ in 100 mM MOPS (pH=6.54). The buffer was then exchanged to 100 mM MOPS (pH=7.0), 1 mM EGTA and 5 mM $MgCl_2$ to remove calcium via dialysis using a 10-kDa molecular weight cut off membrane. The fluorescent GTP analog was added to give a final concentration of 3.0 μM and fluorescence was measured on a microplate reader after 10 minutes of incubation (Ex/Em: 490/520 nm).

Inhibitor compounds 67 and 72 both abolished the GTP binding ability of human TG2 (hTG2). Results are shown in FIG. 1.

Example 4. Transglutaminase Isozyme Selectivity

Given the broad range of localization and biological roles played by the transglutaminase family, isozyme selectivity is a high priority in inhibitor optimization. Previously we showed that inhibitors NC9 and VA4 both demonstrate good selectivity for TG2, compared to the other major transglutaminase isozymes (Akbar, A. et al., "Structure-Activity Relationships of Potent, Targeted Covalent Inhibitors That Abolish Both the Transamidation and GTP Binding Activities of Human Tissue Transglutaminase." J. Med. Chem. 2017, 60 (18), 7910-7927). Here, we tested the selectivity of our starting compound AA9 and inhibitor compounds 72 and 74, against four other therapeutically relevant human transglutaminase isozymes: FXIIIa, hTG1, hTG3 and hTG6.

Kitz and Wilson conditions were applied, using two different transglutaminase activity assays: the reaction with chromogenic substrate AL5 for hTG1, hTG2, and hTG6 (using the colorimetric transamidase activity assay described above), and a commercially available peptidic FRET-quenched substrate for FXIIIa and hTG3 using a fluorescence isopeptidase activity assay, as follows:

Fluorescence isopeptidase activity assay. The isopeptidase activity of pre-activated TG3a and FXIIIa (purchased from Zedira) was measured via a fluorescence-based assay as described (Kirily, R. et al., "Isopeptidase activity of human transglutaminase 2: disconnection from transamidation and characterization by kinetic parameters." *Amino Acids* 2016, 48 (1), 31-40) using the commercially available peptidic FRET quenched probe A101. Briefly, the final concentration in the reaction mixture contained 50 mM Tris (pH 7.0), 10 mM $CaCl_2$, 100 mM NaCl, 2.8 mM TCEP, 50 μM A101 and 14 mM H-Gly-OMe. The reaction was monitored at 25° C. using a BioTek Synergy 4 plate reader (Ex/Em: 318/413 nm). Enzymatic inhibition assays were run under Kitz and Wilson conditions (Kitz, R. and Wilson, I. B., "Esters of methanesulfonic acid as irreversible inhibitors of acetylcholinesterase." *J. Biol. Chem.* 1962, 237, 3245-49), which were established for TG3a and FXIIIa at a substrate (A101) concentration of 50 μM using enzyme concentrations of 0.17 μM and 0.11 μM for TG3a and FXIIIa, respectively.

To ensure each isozyme was exposed to the same relative binding potential of AA9, 72 and 74, the concentrations of inhibitors and substrates were adjusted according to the $K_M$ value of each substrate with its respective isozyme. This approach established equal values of $[I]/\alpha$ in each assay, where a is a measure of the competition posed by the assay substrate (i.e. $\alpha=(1+[S]/K_M)$).

Under these normalized experimental conditions, the activity of each isozyme was then measured in the presence of inhibitors AA9, 72 and 74. All three of these inhibitors inactivated TG2 almost completely, in less than five minutes. However, none of these inhibitors showed any detectable inhibition of any of the other isozymes tested. Results are shown in FIGS. 2A-2E for compound 72 and FIGS. 3A-3E for compound 74.

In summary, in the above Examples we investigated the effect of changing the N-terminal benzyloxy group of the benchmark compound AA9, which was one of the best inhibitors identified previously (WO 2017/179018). We found that changing the N-terminal benzyloxy group of AA9 to polar aromatic (heteroaryl) groups resulted in decreased TG2 inhibition efficiency. Changing the N-terminal group back to a hydrophobic alkyl group was able to restore some of the initial activity, showing slightly more inhibition activity than heteroaryl groups, whereas hydrophobic aryl groups at the N-terminal position gave about the same amount of TG2 inhibition activity. Surprisingly, compounds with an arylalkyl group at the N-terminal position were significantly better than the other test compounds in the series. Moreover, the arylalkyl compounds were significantly better than the previous benchmark inhibitor compound AA9.

Since the phenylacetyl series of compounds showed particularly strong inhibition activity, we explored this further and tested a series of substituted phenylacetyl derivatives. This series demonstrated significantly higher TG2 inhibition efficiency than the benchmark inhibitor compound AA9.

A few sulfonyl analogue compounds were also tested, but these compounds were found to be much less effective, emphasizing the unique effectiveness of the arylalkyl carboxamide inhibitors.

Furthermore, compounds 67 and 72 were both shown to suppress completely the GTP binding ability of TG2, indicating strong potential for therapeutic application via this mechanism of action. Both compounds also demonstrated excellent selectivity in vitro in their reaction with TG2 relative to other human transglutaminases, consistent with potential therapeutic use as TG2 inhibitors.

Example 5. Synthesis of Representative TG2 Inhibitor Compounds

Commercially available reagents and solvents were used without further purification. $^1H$- and $^{13}C$-NMR spectra were recorded on a Bruker 300-, 400- or 500-MHz instrument and chemical shifts were reported in ppm referenced to the deuterated solvent peak. High-resolution mass spectra were obtained with a quadrupole time-of-flight (QTOF) analyzer and electrospray ionization (ESI). Inhibitors were prepared by methods analogous to those previously reported (de Macedo, P. et al., "Synthesis of dipeptide-bound epoxides and α,β-unsaturated amides as potential irreversible transglutaminase inhibitors." *Bioorg. Med. Chem.* 2001, 10 (2), 355-360; Akbar, A. et al., "Structure-Activity Relationships of Potent, Targeted Covalent Inhibitors That Abolish Both the Transamidation and GTP Binding Activities of Human Tissue Transglutaminase." J. Med. Chem. 2017, 60 (18), 7910-7927). Final compounds used for in vitro analysis were of >95% purity as judged by the HPLC chromatogram obtained using a Phenomenex C18 reversed-phase column, 4.6×150 mm; solvent: acetonitrile/water. An isocratic elution of 40:60 acetonitrile/water or a gradient elution of 75:25 to 30:70 acetonitrile/water over 20 minutes or 80:20 to 30:70 acetonitrile/water with 0.1% TFA over 15 minutes was used depending on the compound. All compounds were eluted with a flow rate of 1.0 mL/min and monitored by UV detection at 260 nm.

Synthesis of tert-Butyl 4-(1-naphthoyl)piperazine-1-carboxylate (3)

(Akbar, A. et al., "Structure-Activity Relationships of Potent, Targeted Covalent Inhibitors That Abolish Both the Transamidation and GTP Binding Activities of Human Tissue Transglutaminase." J. Med. Chem. 2017, 60 (18), 7910-7927):

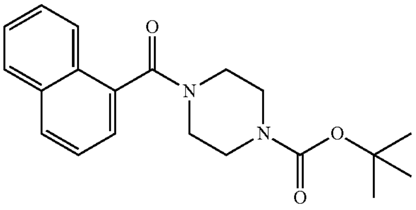 [SMILES: CC(C)(C)OC(=O)N1CCN(C(=O)c2cccc3ccccc23)CC1]

Mono-Boc-piperazine 1 (1.07 g, 5.74 mmol) was dissolved in 50 mL of DCM and cooled to 0° C. Diisopropylethylamine (1.19 mL, 6.89 mmol) was added, followed by the addition of 1-naphthoyl chloride 2 (1.31 g, 6.89 mmol). The solution was stirred for 4 h and allowed to warm to room temperature. The reaction was quenched by addition of 10 mL 1M HCl. The DCM was separated and washed with acidic water and brine, dried with anhydrous magnesium sulfate, filtered and concentrated under reduced pressure to afford the crude product as a brown oil. The oil was purified by flash chromatography over silica gel (elution with gradient DCM to DCM:MeOH(2%)) to afford 1.776 g (91%) of the desired product as a light brown, sticky foam. $^1$H NMR (400 MHz, $CDCl_3$) δ 7.92-7.85 (m, 2H), 7.85-7.80 (m, 1H), 7.56-7.46 (m, 3H), 7.41 (dd, J=7.0, 1.3 Hz, 1H), 3.97 (dt, J=13.0, 5.2 Hz, 1H), 3.86 (dt, J=12.8, 5.3 Hz, 1H), 3.70-3.56 (m, 2H), 3.33-3.25 (m, 1H), 3.19-3.12 (m, 2H), 1.45 (s, 9H); $^{13}$C NMR (100 MHz, $CDCl_3$) δ 169.7, 154.6, 133.9, 133.6, 129.7, 129.5, 128.6, 127.3, 126.7, 125.3, 124.7, 124.0, 80.5, 47.1, 41.8, 28.5; HRMS (ESI-QTOF) m/z $[M+Na]^+$ calcd for $C_{20}H_{24}N_2O_3Na$ 363.1685; found 363.1676.

Synthesis of Naphthalen-1-yl(piperazin-1-yl)methanone (4)

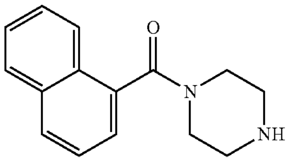 [SMILES: O=C(c1cccc2ccccc12)N1CCNCC1]

tert-Butyl 4-(1-naphthoyl)piperazine-1-carboxylate (200 mg, 0.587 mmol) was dissolved in 10 mL of DCM and cooled to 0° C. TFA (0.5 mL, excess) was slowly added and the mixture was warmed to room temperature and left stirring for 4 h. The reaction was considered complete by TLC and quenched by addition of 5 mL of 1M NaOH solution. The DCM was washed with 5 mL 1M NaOH and 5 mL brine, dried with anhydrous magnesium sulfate, filtered and concentrated to afford a clear oil. The oil solidified into a 122 mg (87%) of a sticky white solid.

$^1$H NMR (400 MHz, $CDCl_3$) δ 7.91-7.82 (m, 3H), 7.57-7.44 (m, 3H), 7.41 (dd, J=7.0, 1.3 Hz, 1H), 3.99 (dt, J=13.1, 5.0 Hz, 1H), 3.87 (dt, J=13.0, 5.2 Hz, 1H), 3.22-3.14 (m, 2H), 3.03 (t, J=5.1 Hz, 2H), 2.74-2.67 (m, 2H), 2.20 (br s, 1H); $^{13}$C NMR (100 MHz, $CDCl_3$) δ 169.6, 134.3, 133.6, 129.7, 129.3, 128.6, 127.2, 126.6, 125.3, 124.9, 123.9, 48.4, 46.7, 46.1, 42.9: HRMS (ESI-QTOF) m/z $[M+Na]^+$ calcd for $C_{15}H_{16}N_2ONa$ 263.1160; found 263.1168.

Synthesis of (S)-Benzyl tert-butyl (6-(4-(1-naphthoyl)piperazin-1-yl)-6-oxohexane-1,5-diyl)dicarbamate (7)

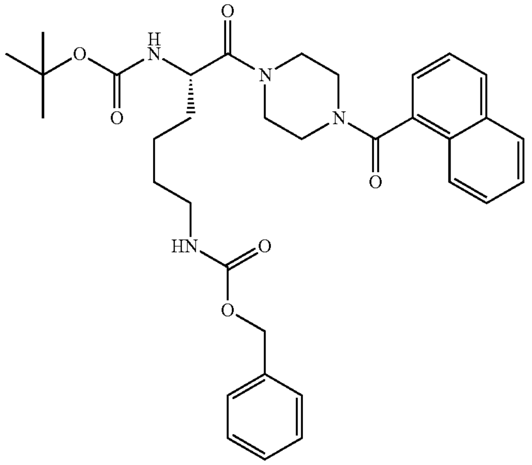 [SMILES: CC(C)(C)OC(=O)N[C@@H](CCCCNC(=O)OCc1ccccc1)C(=O)N1CCN(C(=O)c2cccc3ccccc23)CC1]

Commercially available Boc-Lys(Z)-OH 5 (225 mg, 0.591 mmol) was dissolved in 10 mL of acetonitrile. EDC-HCl (136 mg, 0.709 mmol) and N-hydroxysuccinamide (82 mg, 0.709 mmol) were added to the solution and left stirring at room temperature overnight. The solution was concentrated to afford a clear oil that was re-dissolved in 10 mL of DCM. The DCM was washed with saturated bicarbonate solution (2×5 mL) and brine (1×5 mL). The DCM was dried with anhydrous magnesium sulfate, filtered and concentrated to afford 281 mg (99%) of the crude NHS ester (6) as a clear oil. The crude product was dissolved in 5 mL of acetonitrile and used in the subsequent reaction.

Compound 4 (122 mg, 0.506 mmol) was dissolved in 5 mL of acetonitrile and diisopropylethylamine (0.10 mL, 0.588 mmol) was added. The solution of NHS ester 6 was added and the solution was left stirring at room temperature overnight. The acetonitrile solution was concentrated by rotary evaporation and the residue was dissolved in 5 mL of DCM. The DCM was washed with $H_2O$ (1×5 mL), saturated sodium bicarbonate solution (1×5 mL) and brine (1×5 mL). The solution was dried with anhydrous magnesium sulfate, filtered and concentrated to afford 261 mg of crude product (7). This was purified by flash chromatography (elution with 40% ethyl acetate and hexanes) to afford 166 mg (54%) of the desired product as a white foam. $^1$H NMR (300 MHz, 373 K $(CD_3)_2SO$) δ 8.03-7.91 (m, 2H), 7.86-7.77 (m, 1H), 7.60-7.52 (m, 3H), 7.46 (dd, J=7.0, 1.3 Hz, 1H), 7.36-7.22 (m, 5H), 6.72 (br s, 1H), 6.34 (br d, J=8.1 Hz, 1H), 5.01 (s, 2H), 4.35 (q, J=7.8 Hz, 1H), 3.55 (br s, 8H), 3.01 (q, J=6.6 Hz, 2H), 1.69-1.42 (m, 4H), 1.38 (s, 9H), 1.34-1.26 (m, 2H); $^{13}$C NMR (76 MHz, $(CD_3)_2SO$) δ 170.2, 167.9, 155.5, 154.5, 136.9, 133.6, 132.6, 128.7, 128.3, 127.7, 127.6, 127.0, 126.9, 126.3, 125.8, 124.6, 124.1, 123.3, 77.7, 64.7, 49.9, 30.9, 28.6, 27.8, 21.8, signals for 4×C of piperazine not visible; HRMS (ESI-QTOF) m/z $[M+Na]^+$ calcd for $C_{34}H_{42}N_4O_6Na$ 625.3002; found 625.2990.

Synthesis of (S)-tert-Butyl (1-(4-(1-naphthoyl)piperazin-1-yl)-6-amino-1-oxohexan-2-yl)carbamate (8)

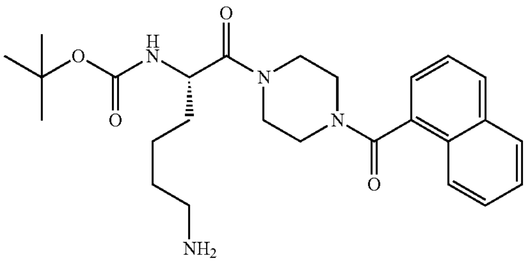 [SMILES: CC(C)(C)OC(=O)N[C@@H](CCCCN)C(=O)N1CCN(C(=O)c2cccc3ccccc23)CC1]

Compound 7 (1.6 g, 2.659 mmol) was dissolved in 50 mL of dry MeOH under nitrogen atmosphere. Pd/C (56 mg, 20 mol %) was added and the flask was evacuated and flushed with nitrogen three times. The flask was subsequently evacuated and flushed with hydrogen three times with vigorous stirring. After 2 h, starting material was still present and fresh Pd/C was added. After 8 h, the solution was filtered over celite and the collected MeOH solution was put under nitrogen atmosphere and Pd/C (20 mol %) was added. The mixture was left stirring vigorously overnight. Starting material was not observed via TLC. The solution was filtered over celite and the methanol was concentrated to afford 1.3 g (94%) of the compound 8 as a white foam.

$^{1}$H NMR (300 MHz, 353 K $(CD_3)_2SO$) δ 8.05-7.93 (m, 2H), 7.89-7.78 (m, 1H), 7.63-7.52 (m, 3H), 7.47 (dd, J=7.0, 1.3 Hz, 1H), 6.48 (br s, 1H), 4.34 (br s, 1H), 3.60 (br s, 8H), 1.66-1.45 (m, 3H), 1.38 (s, 9H), 1.34-1.27 (m, 5H); $^{13}$C NMR (76 MHz, 353 K $(CD_3)_2SO$) δ 170.3, 167.9, 154.6, 133.7, 132.7, 128.8, 128.4, 127.9, 126.5, 125.9, 124.8, 124.2, 123.4, 78.7, 77.7, 50.0, 40.9, 32.6, 31.2, 27.8, 22.1; HRMS (ESI-QTOF) m/z $[M+Na]^+$ calcd for $C_{26}H_{36}N_4O_4Na$ 491.2634; found 491.2644.

Synthesis of (S)-tert-Butyl (1-(4-(1-naphthoyl)piperazin-1-yl)-6-acrylamido-1-oxohexan-2-yl)carbamate (10)

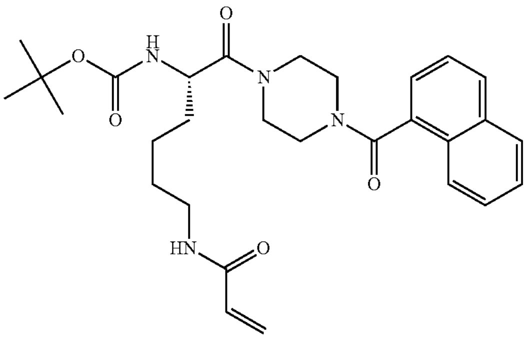 [SMILES: C=CC(=O)NCCCC[C@H](NC(=O)OC(C)(C)C)C(=O)N1CCN(C(=O)c2cccc3ccccc23)CC1]

Free amine 8 (896 mg, 1.913 mmol) was dissolved in 30 mL of DCM and cooled to 0° C. Triethylamine (0.80 mL, 5.74 mmol) was added, followed by a catalytic amount of DMAP (10 mol %). In a small vial, acyrloyl chloride (0.23 mL, 2.87 mmol) was dissolved in 5 mL of DCM and this solution was added dropwise to the solution of free amine. The solution was warmed to room temperature and was stirred for 6 h, becoming light yellow in colour. The solution was diluted by the addition of 25 mL of DCM. The solution was washed with 1M HCl (2×20 mL) and saturated sodium bicarbonate solution (1×20 mL). The DCM was dried with sodium sulfate, filtered and concentrated to afford the crude product as a yellow oil. The crude product was purified by flash chromatography (elution with gradient 60% ethyl acetate:hexanes to 100% ethyl acetate) to afford 711 mg (71%) of product 10 as a white solid. mp 94-96° C.; $^{1}$H NMR (300 MHz, 353 K $(CD_3)_2SO$) δ 8.05-7.94 (m, 2H), 7.86-7.79 (m, 1H), 7.74 (bs, 1H), 7.63-7.53 (m, 3H), 7.47 (dd, J=7.0, 1.3 Hz, 1H), 6.48 (bs, 1H), 6.19 (dd, J=17.2, 10.0 Hz, 1H), 6.04 (dd, J=17.1, 2.4 Hz, 1H), 5.52 (dd, J=10.0, 2.4 Hz, 1H), 4.34 (bs, 1H), 3.56 (very bs, 8H), 3.12 (q, J=6.5 Hz, 1H), 1.80-1.12 (m, 15H); $^{13}$C NMR (75 MHz, 353 K $(CD_3)_2SO$) δ 170.3, 167.9, 164.2, 154.7, 133.7, 132.7, 131.7, 128.8, 128.4, 127.9, 126.5, 125.9, 124.8, 124.2, 123.8, 123.5, 77.8, 50.0, 49.9, 37.9, 30.9, 28.4, 27.8, 22.2; HRMS (ESI-QTOF) m/z [M+Na]+ calcd for $C_{29}H_{38}N_4O_5Na$ 545.2740; found 545.2759.

Synthesis of (S)-N-(6-(4-(1-naphthoyl)piperazin-1-yl)-5-amino-6-oxohexyl)acrylamide (11)

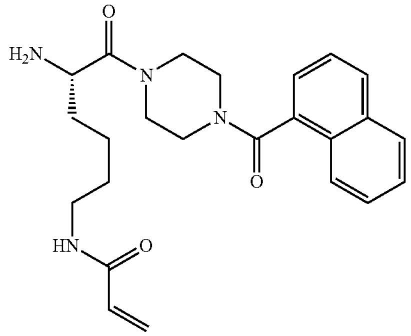 [SMILES: C=CC(=O)NCCCC[C@H](N)C(=O)N1CCN(C(=O)c2cccc3ccccc23)CC1]

Boc-protected intermediate 10 (250 mg, 0.478 mmol) was dissolved in 3 mL of dichloromethane. TFA (0.5 mL, excess) was added and the homogeneous solution was left stirring at room temperature. The reaction was monitored via thin layer chromatography and was determined to be complete after 1 h. The solution was diluted to a final volume of 15 mL in dichloromethane and washed with saturated sodium bicarbonate solution (2×5 mL), dried with anhydrous sodium sulfate, filtered and concentrated under vacuum to afford 162 mg (80%) of the crude product 11 as a white solid. This product was used in subsequent reactions without further purification. HRMS (ESI-QTOF) m/z $[M+Na]^+$ calcd for $C_{24}H_{30}N_4O_3Na$ 445.2216; found 445.2201.

General Procedure A: Synthesis of NHS Esters 6, 25-27, 46, and 48-52:

The carboxylic acid was dissolved in acetonitrile (0.1 M) and EDC-HCl (1.2 equiv.) and NHS (1.2 equiv.) were added. The solution is typically homogeneous. If the solution is not homogeneous; otherwise, a small amount of DMF was added. The solution was left stirring at room temperature overnight. This reaction can also be completed in dichloromethane. The acetonitrile was removed under vacuum and the residue was dissolved in dichloromethane. The dichloromethane was washed with 1 M HCl, saturated sodium bicarbonate solution and dried with anhydrous magnesium sulfate, filtered and concentrated to afford white, sticky solids (50-99%), which were subsequently used without further purification.

General Procedure B: Synthesis of NHS Esters 12-17:

The commercially available carboxylic acid was dissolved in dichloromethane (0.1 M), to which was added EDC-HCl (1.2 equiv.) and NHS (1.2 equiv.). The solution was typically homogeneous, otherwise a small amount of DMF was added. The solution was left stirring at room temperature overnight. The solution was diluted with dichloromethane, washed with saturated sodium bicarbonate solution and dried with anhydrous magnesium sulfate, filtered and concentrated to afford white, sticky solids (24-31% for imidazoles, 56-96% for pyridines), which were subsequently used without further purification.

General Procedure C: Coupling of Free Amine (11) with N-Heterocyclic NHS Esters 12-17 to Give Heteroaryl Inhibitors 18-23:

Free amine intermediate was dissolved in dichloromethane (0.1 M) and triethylamine (2.5 equiv.) were added. The NHS ester (1.5 equiv.) was added and the homogeneous solution was left stirring at room temperature for 16 h. The solution was diluted with dichloromethane and subsequently washed with saturated sodium bicarbonate solution (2×20 mL). The dichloromethane was dried with sodium sulfate, filtered and concentrated to afford the crude product. Compounds were purified by flash chromatography over silica, eluting with dichloromethane-methanol gradients to afford the final compounds in 22-90% yields as sticky white foams.

General Procedure D: Coupling of Free Amine (11) with NHS Esters 24-26, 46, and 48-60:

The free amine intermediate was dissolved in dichloromethane (0.1 M) and triethylamine (2.5 equiv.) was added. The NHS ester (1.5 equiv.) was then added, and the homogeneous solution was left stirring at room temperature for 16 h. The solution was diluted with dichloromethane and subsequently washed with 1 M HCl (2×20 mL), followed by saturated sodium bicarbonate solution (2×20 mL). The dichloromethane was dried with sodium sulfate, filtered and concentrated to afford the crude product. Compounds were purified by flash chromatography over silica, elution with dichloromethane-methanol gradients to afford the final compounds in 30-89% yields as sticky white foams.

General Procedure E: Coupling of Free Amine (11) with Acid Chlorides and Anhydrides 2, 27-32, 42-45 and 47:

The free amine intermediate was dissolved in dichloromethane (0.1 M) and triethylamine (2.5 equiv.) was added. The solution was cooled to 0° C. and the acid chloride was added dropwise. The solution was warmed to room temperature and left stirring for 2-16 h. The solution was diluted in dichloromethane and washed with water and saturated sodium bicarbonate solution, dried with anhydrous magnesium sulfate, filtered and concentrated to afford the crude product as a sticky yellow-to-white solid. Compounds were purified by flash chromatography over silica, elution with dichloromethane-methanol gradients to afford the final compounds in 25-91% yields as sticky white foams.

General Procedure F: Coupling of Free Amine 11 with Sulfonyl Chlorides 81-85 to Give Sulfonamides 86-90:

The free amine intermediate was dissolved in dichloromethane (0.1 M) and triethylamine (2.5 equiv.) was added. The solution was cooled to 0° C. and the sulfonyl chloride was added dropwise. The solution was warmed to room temperature and left stirring for 2-16 h. The solution was diluted in dichloromethane and washed with water and saturated sodium bicarbonate solution, dried with anhydrous magnesium sulfate, filtered and concentrated to afford the crude product as a sticky yellow-to-white solid. Compounds were purified by flash chromatography over silica, elution with dichloromethane-methanol gradients to afford the final compounds in 48-66% yields as sticky white foams.

Synthesis of (S)-N-(1-(4-(1-Naphthoyl)piperazin-1-yl)-6-acrylamido-1-oxohexan-2-yl)picolinamide (18)

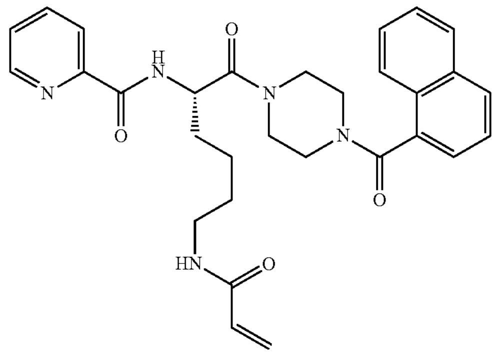 [SMILES: C=CC(=O)NCCCC[C@H](NC(=O)c1ccccn1)C(=O)N1CCN(C(=O)c2cccc3ccccc23)CC1]

Compound 18 was prepared from Boc-deprotected 11 and picolinoyl NHS ester (12) using general procedure C to collect 19 mg (44%) of the desired product as a white foam. $^{1}H$ NMR (300 MHz, $(CD_3)_2SO$) δ 8.73 (br d, J=7.9 Hz, 1H), 8.67 (dt, J=4.7, 1.4 Hz, 1H), 8.08-7.96 (m, 5H), 7.81 (br s, 1H), 7.66-7.54 (m, 4H), 7.53-7.44 (m, 1H), 6.26-5.93 (m, 2H), 5.51 (t, J=11.1 Hz, 1H), 5.05 (br s, 0.5H), 4.88 (br s, 0.5H), 3.92-3.65 (m, 4H), 3.57-3.40 (m, 2H), 3.19-2.91 (m, 4H), 1.86-1.52 (m, 2H), 1.54-1.12 (m, 6H). $^{1}H$ NMR (300 MHz, 353 K $(CD_3)_2SO$) δ 8.65 (ddd, J=4.7, 1.7, 1.0 Hz, 1H), 8.59 (d, J=8.1 Hz, 1H), 8.06-7.94 (m, 4H), 7.87-7.79 (m, 1H), 7.73 (br s, 1H), 7.63-7.53 (m, 4H), 7.48 (dd, J=7.0, 1.3 Hz, 1H), 6.17 (dd, J=17.1, 10.1 Hz, 1H), 6.01 (dd, J=17.1, 2.4 Hz, 1H), 5.49 (dd, J=10.0, 2.4 Hz, 1H), 4.97 (br s, 1H), 3.63 (br s, 8H), 3.11 (q, J=6.5 Hz, 2H), 1.90-1.63 (m, 2H), 1.54-1.42 (m, 2H), 1.41-1.24 (m, 2H); $^{13}C$ NMR (76 MHz, 353 K $(CD_3)_2SO$) δ 169.5, 167.9, 164.2, 162.7, 149.1, 148.1, 137.3, 133.6, 132.7, 131.7, 128.8, 128.5, 127.9, 126.5, 126.1, 125.9, 124.8, 124.2, 123.7, 123.5, 121.3, 48.3, 37.9, 31.5, 28.4, 21.8, signals for 4×C of piperazine not visible; HRMS (ESI-QTOF) m/z $[M+Na]^+$ calcd for $C_{30}H_{33}N_5O_4Na$ 550.2430; found 550.2430.

Synthesis of (S)-N-(1-(4-(1-naphthoyl)piperazin-1-yl)-6-acrylamido-1-oxohexan-2-yl)nicotinamide (19)

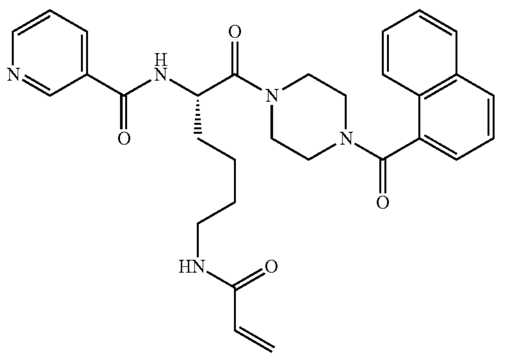 [SMILES: C=CC(=O)NCCCC[C@H](NC(=O)c1cccnc1)C(=O)N1CCN(C(=O)c2cccc3ccccc23)CC1]

Compound 19 was prepared from Boc-deprotected 11 and nicotinoyl NHS ester (13) using general procedure C to collect 27 mg (52%) of the desired product as a white foam. $^1$H NMR (300 MHz, 353 K $(CD3)_2SO$) δ 9.03-9.00 (m, 1H), 8.69 (dd, J=4.8, 1.7 Hz, 1H), 8.52 (d, J=7.7 Hz, 1H), 8.19 (dt, J=7.9, 2.0 Hz, 1H), 8.01-7.94 (m, 2H), 7.87-7.79 (m, 1H), 7.75 (br s, 1H), 7.63-7.51 (m, 3H), 7.51-7.43 (m, 2H), 6.18 (dd, J=17.1, 10.0 Hz, 1H), 6.03 (dd, J=17.2, 2.4 Hz, 1H), 5.51 (dd, J=10.0, 2.4 Hz, 1H), 5.03-4.75 (m, 1H), 3.62 (br s, 8H), 3.14 (q, J=6.5 Hz, 2H), 1.88-1.67 (m, 2H), 1.59-1.29 (m, 4H); 13C NMR (75 MHz, 353 K $(CD3)_2SO$) δ 169.8, 167.9, 164.5, 164.3, 151.4, 148.2, 134.6, 133.7, 132.7, 131.7, 129.28, 128.8, 128.5, 127.9, 126.5, 126.0, 124.8, 124.2, 123.8, 123.5, 122.8, 49.1, 37.9, 30.5, 28.4, 22.4, signals for 4×C of piperazine not visible; HRMS (ESI-QTOF) m/z [M+Na]+ calcd for $C_{30}H_{33}N_5O_4Na$ 550.2430; found 550.2444.

Synthesis of (S)-N-(1-(4-(1-naphthoyl)piperazin-1-yl)-6-acrylamido-1-oxohexan-2-yl)isonicotinamide (19)

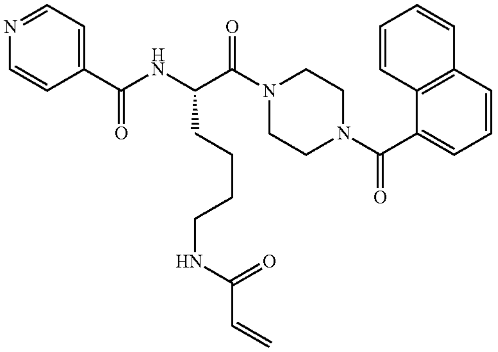 [SMILES: C=CC(=O)NCCCC[C@H](NC(=O)c1ccncc1)C(=O)N1CCN(C(=O)c2cccc3ccccc23)CC1]

Compound 19 was prepared from Boc-deprotected 11 and isonicotinoyl NHS ester (14) using general procedure C to collect 21 mg (48%) of the desired product as a white foam. $^1$H NMR (300 MHz, $(CD_3)_2SO$) δ 8.74 (dd, J=8.2, 3.5 Hz, 1H), 8.67 (d, J=4.8 Hz, 1H), 8.11-7.95 (m, 5H), 7.81 (br s, 1H), 7.68-7.51 (m, 4H), 7.53-7.44 (m, 1H), 6.28-5.92 (m, 2H), 5.52 (t, J=10.8 Hz, 1H), 5.11-4.97 (m, 0.5H), 4.94-4.81 (m, 0.5H), 3.96-3.63 (m, 4H), 3.59-3.42 (m, 2H), 3.28-2.98 (m, 4H), 1.87-1.57 (m, 2H), 1.54-1.17 (m, 4H). $^1$H NMR (300 MHz, 353 K $(CD_3)_2SO$) δ 8.69-8.55 (m, 2H), 8.07-7.93 (m, 4H), 7.87-7.76 (m, 1H), 7.73 (br s, 1H), 7.63-7.52 (m, 4H), 7.48 (dd, J=7.0, 1.3 Hz, 1H), 6.17 (dd, J=17.2, 10.0 Hz, 1H), 6.01 (dd, J=17.2, 2.4 Hz, 1H), 5.49 (dd, J=10.0, 2.4 Hz, 1H), 4.97 (br s, 1H), 3.63 (br s, 8H), 3.19-3.09 (m, 2H), 1.90-1.59 (m, 2H), 1.57-1.40 (m, 2H), 1.42-1.24 (m, 2H); $^{13}$C NMR (75 MHz, 353 K $(CD_3)_2SO$) δ 169.6, 168.0, 164.3, 162.8, 149.2, 148.1, 137.4, 133.7, 132.7, 131.7, 128.9, 128.5, 127.9, 126.6, 126.2, 126.0, 124.9, 124.3, 123.8, 123.5, 121.4, 48.4, 37.9, 31.5, 28.4, 21.9, signals for 4×C of piperazine not visible; HRMS (ESI-QTOF) m/z $[M+Na]^+$ calcd for $C_{30}H_{33}N_5O_4Na$ 550.2430; found 550.2458.

Synthesis of (S)-N-(1-(4-(1-naphthoyl)piperazin-1-yl)-6-acrylamido-1-oxohexan-2-yl)-1-methyl-1H-imidazole-2-carboxamide (21)

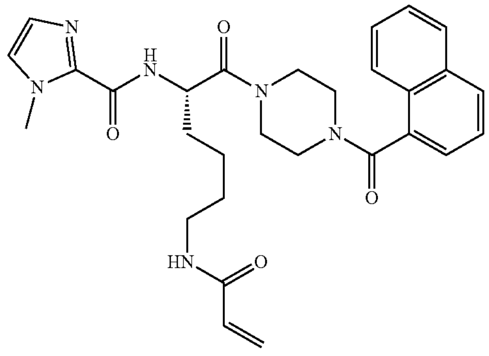 [SMILES: C=CC(=O)NCCCC[C@H](NC(=O)c1nccn1C)C(=O)N1CCN(C(=O)c2cccc3ccccc23)CC1]

Compound 21 was prepared from Boc-deprotected 11 and imidazoyl NHS ester (15) using general procedure C to collect 26 mg (63%) of the desired product as a white foam. $^1$H NMR (300 MHz, $(CD_3)_2SO$) δ 8.18 (t, J=7.6 Hz, 1H), 8.10-7.95 (m, 3H), 7.80 (br s, 1H), 7.63-7.53 (m, 3H), 7.54-7.42 (m, 1H), 7.37-7.30 (m, 1H), 6.98 (d, J=1.0 Hz, 1H), 6.41-5.91 (m, 2H), 5.54 (d, J=11.5 Hz, 1H), 5.12-4.87 (m, 0.5H), 4.89-4.73 (m, 0.5H), 4.07-3.64 (m, 7H), 3.64-3.35 (m, 2H), 3.20-2.90 (m, 4H), 1.84-1.55 (m, 2H), 1.54-1.08 (m, 4H). $^1$H NMR (300 MHz, 353 K $(CD_3)_2SO$) δ 8.11-7.92 (m, 3H), 7.90-7.81 (m, 1H), 7.73 (br s, 1H), 7.62-7.53 (m, 3H), 7.48 (dd, J=7.0, 1.3 Hz, 1H), 7.28 (d, J=1.0 Hz, 1H), 6.97 (d, J=1.1 Hz, 1H), 6.18 (dd, J=17.1, 10.0 Hz, 1H), 6.02 (dd, J=17.2, 2.4 Hz, 1H), 5.50 (dd, J=10.0, 2.4 Hz, 1H), 4.87 (br s, 1H), 3.94 (s, 3H), 3.61 (br s, 8H), 3.12 (q, J=6.6 Hz, 2H), 1.88-1.58 (m, 2H), 1.55-1.39 (m, 2H), 1.42-1.23 (m, 2H); $^{13}$C NMR (75 MHz, 353 K $(CD_3)_2SO$) δ 169.5, 167.9, 164.2, 157.9, 138.0, 133.6, 132.7, 131.7, 128.8, 128.5, 127.9, 126.8, 126.5, 125.9, 125.7, 124.8, 124.2, 123.7, 123.5, 47.9, 37.9, 34.4, 31.4, 28.4, 21.9, signals for 4×C of piperazine not visible; HRMS (ESI-QTOF) m/z [M+Na]+ calcd for $C_{29}H_{34}N_6O_4Na$ 553.2539; found 553.2546.

Synthesis of (S)-N-(1-(4-(1-naphthoyl)piperazin-1-yl)-6-acrylamido-1-oxohexan-2-yl)-1-methyl-1H-imidazole-4-carboxamide (22)

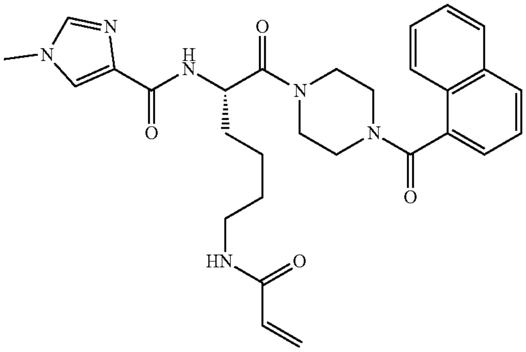 [SMILES: C=CC(=O)NCCCC[C@H](NC(=O)c1cn(C)cn1)C(=O)N1CCN(C(=O)c2cccc3ccccc23)CC1]

Compound 22 was prepared from Boc-deprotected 11 and imidazoyl NHS ester (16) using general procedure C to collect 22 mg (54%) of the desired product as a white foam. $^{1}H$ NMR (300 MHz, $(CD_3)_2SO$) δ 8.00 (d, J=8.3 Hz, 3H), 7.86-7.72 (m, 2H), 7.65 (s, 1H), 7.63-7.51 (m, 3H), 7.53-7.40 (m, 1H), 6.31-5.86 (m, 2H), 5.60-5.34 (m, 1H), 5.07-4.89 (m, 0.5H), 4.88-4.71 (m, 0.5H), 3.90-3.55 (m, 7H), 3.55-3.35 (m, 2H), 3.23-2.80 (m, 4H), 1.83-1.07 (m, 7H). $^{1}H$ NMR (300 MHz, 353 K $(CD_3)_2SO$) δ 8.03-7.93 (m, 2H), 7.86-7.78 (m, 1H), 7.72 (s, 1H), 7.65-7.52 (m, 6H), 7.47 (dd, J=7.0, 1.3 Hz, 1H), 6.18 (dd, J=17.1, 10.1 Hz, 1H), 6.02 (dd, J=17.1, 2.5 Hz, 1H), 5.50 (dd, J=10.0, 2.4 Hz, 1H), 4.89 (br s, 1H), 3.95-3.39 (m, 10H), 3.16-3.08 (m, 2H), 1.86-1.56 (m, 2H), 1.51-1.17 (m, 5H); $^{13}C$ NMR (75 MHz, 353 K $(CD_3)_2SO$) 169.9, 167.9, 164.2, 160.9, 137.6, 135.8, 133.6, 132.7, 131.7, 128.8, 128.4, 127.9, 126.5, 125.9, 124.8, 124.2, 123.7, 123.4, 122.7, 47.4, 37.9, 32.8, 31.7, 28.4, 21.9, signals for 4×C of piperazine not visible; HRMS (ESI-QTOF) m/z [M+Na]+ calcd for C29H34N6O4Na 553.2539; found 553.2539.

Synthesis of (S)-N-(1-(4-(1-naphthoyl)piperazin-1-yl)-6-acrylamido-1-oxohexan-2-yl)-1-methyl-1H-imidazole-5-carboxamide (23)

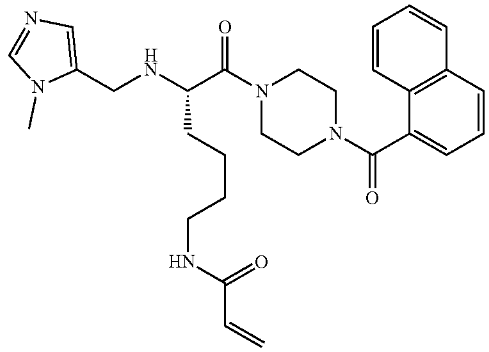 [SMILES: C=CC(=O)NCCCC[C@H](NCc1cncn1C)C(=O)N1CCN(C(=O)c2cccc3ccccc23)CC1]

Compound 23 was prepared from Boc-deprotected 11 and imidazoyl NHS ester (17) using general procedure C to collect 28 mg (41%) of the desired product as a white foam. $^{1}H$ NMR (300 MHz, 353 K $(CD_3)_2SO$) δ 8.37 (dd, J=19.0, 7.9 Hz, 1H), 8.17-7.95 (m, 3H), 7.85-7.64 (m, 3H), 7.64-7.35 (m, 4H), 6.40-5.89 (m, 2H), 5.64-5.41 (m, 1H), 4.97-4.82 (m, 0.5H), 4.77-4.64 (m, 0.5H), 3.92-3.60 (m, 7H), 3.54-3.38 (m, 2H), 3.23-2.96 (m, 4H), 1.75-1.60 (m, 2H), 1.50-0.92 (m, 4H). $^{1}H$ NMR (300 MHz, 353 K $(CD_3)_2SO$) δ 8.05 (d, J=7.9 Hz, 1H), 8.02-7.94 (m, 2H), 7.87-7.79 (m, 1H), 7.74 (br s, 1H), 7.66 (br s, 2H), 7.62-7.52 (m, 3H), 7.47 (dd, J=7.0, 1.3 Hz, 1H), 6.18 (dd, J=17.1, 10.1 Hz, 1H), 6.03 (dd, J=17.1, 2.4 Hz, 1H), 5.51 (dd, J=10.0, 2.4 Hz, 1H), 4.92-4.73 (m, 1H), 3.79 (s, 3H), 3.61 (br s, 8H), 3.13 (q, J=6.5 Hz, 2H), 1.70 (q, J=7.7 Hz, 2H), 1.63-1.13 (m, 4H); $^{13}C$ NMR (75 MHz, 353 K $(CD_3)_2SO$) δ 169.9, 167.9, 164.2, 159.3, 141.4, 133.7, 132.7, 132.0, 131.7, 128.8, 128.4, 127.9, 126.5, 125.9, 125.2, 124.8, 124.2, 123.7, 123.5, 48.1, 45.9, 37.9, 32.8, 30.6, 28.4, 22.4; HRMS (ESI-QTOF) m/z $[M+Na]^+$ calcd for $C_{29}H_{34}N_6O_4Na$ 553.2539; found 553.2549.

Synthesis of (1S,3S,5S,7S)-N-((S)-1-(4-(1-naphthoyl)piperazin-1-yl)-6-acrylamido-1-oxohexan-2-yl)adamantane-2-carboxamide (33)

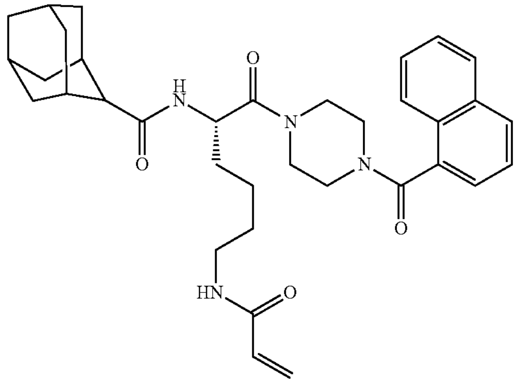 [SMILES: C=CC(=O)NCCCC[C@H](NC(=O)C1C2CC3CC(C2)CC1C3)C(=O)N1CCN(C(=O)c2cccc3ccccc23)CC1]

Compound 33 was prepared from Boc-deprotected 11 and adamanecarboxyl NHS ester (24) using general procedure D to collect 33 mg (53%) of the desired product as a white foam. $^{1}H$ NMR (300 MHz, $CDCl_3$) δ 8.10-7.95 (m, 3H), 7.80 (br s, 1H), 7.62-7.53 (m, 3H), 7.49 (dd, J=7.0, 1.3 Hz, 1H), 7.44-7.31 (m, 1H), 6.32-5.89 (m, 2H), 5.53 (t, J=11.4 Hz, 1H), 4.72 (dd, J=14.2, 7.3 Hz, 0.5H), 4.63-4.49 (m, 0.5H), 3.92-3.56 (m, 4H), 3.48-3.36 (m, 2H), 3.20-2.77 (m, 4H), 2.02-1.87 (m, 3H), 1.86-1.06 (m, 19H). $^{1}H$ NMR (300 MHz, 353 K $(CD_3)_2SO$) δ 8.11-7.94 (m, 2H), 7.89-7.78 (m, 1H), 7.73 (br s, 1H), 7.64-7.51 (m, 3H), 7.47 (dd, J=7.0, 1.4 Hz, 1H), 7.05 (d, J=7.9 Hz, 1H), 6.19 (dd, J=17.1, 10.1 Hz, 1H), 6.03 (dd, J=17.1, 2.4 Hz, 1H), 5.51 (dd, J=10.0, 2.4 Hz, 1H), 4.68 (br d, J=7.2 Hz, 1H), 3.56 (br s, 8H), 3.11 (q, J=6.6 Hz, 2H), 1.97 (br s, 3H), 1.79 (br s, 6H), 1.75-1.51 (m, 8H), 1.49-1.36 (m, 2H), 1.35-1.17 (m, 2H); $^{13}C$ NMR (75 MHz, 353 K $(CD_3)_2SO$) δ 175.9, 170.1, 167.9, 164.2, 133.7, 132.7, 131.7, 128.8, 128.5, 127.9, 126.5, 125.9, 124.8, 124.2, 123.7, 123.5, 47.9, 39.6, 38.3, 37.9, 35.8, 30.8, 28.4, 27.4, 21.9, signals for 4×C of piperazine not visible; HRMS (ESI-QTOF) m/z $[M+Na]^+$ calcd for $C_{35}H_{44}N_4O_4Na$ 607.3260; found 607.3269.

Synthesis of (S)-N-(6-(4-(1-naphthoyl)piperazin-1-yl)-5-(2-cyclohexylacetamido)-6-oxohexyl)acrylamide (34)

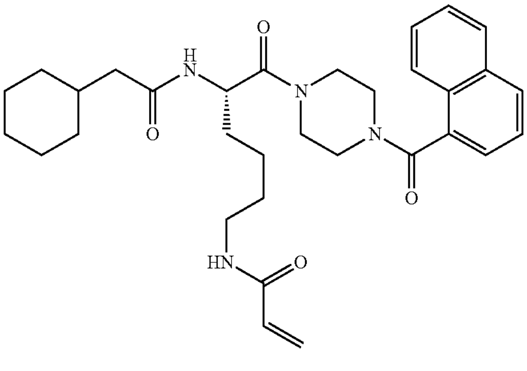 [SMILES: C=CC(=O)NCCCC[C@H](NC(=O)CC1CCCCC1)C(=O)N1CCN(C(=O)c2cccc3ccccc23)CC1]

Compound 34 was prepared from Boc-deprotected 11 and cyclohexylacetyl NHS ester (25) using general procedure D to collect 37 mg (63%) of the desired product as a white foam. $^1$H NMR (300 MHz, $CDCl_3$) δ 8.11-7.93 (m, 4H), 7.80 (br s, 1H), 7.65-7.52 (m, 3H), 7.48 (dd, J=7.0, 1.3 Hz, 1H), 6.33-5.91 (m, 2H), 5.54 (t, J=11.8 Hz, 1H), 4.73 (d, J=6.8 Hz, 0.5H), 4.56 (d, J=7.1 Hz, 0.5H), 3.89-3.57 (m, 4H), 3.52-3.33 (m, 2H), 3.20-2.94 (m, 4H), 2.17-1.83 (m, 2H), 1.74-1.03 (m, 15H), 0.98-0.75 (m, 2H). $^1$H NMR (300 MHz, 353 K $(CD_3)_2SO$) δ 8.04-7.94 (m, 2H), 7.85-7.78 (m, 1H), 7.77-7.64 (m, 2H), 7.62-7.53 (m, 3H), 7.47 (dd, J=7.0, 1.3 Hz, 1H), 6.19 (dd, J=17.1, 10.0 Hz, 1H), 6.04 (dd, J=17.1, 2.4 Hz, 1H), 5.52 (dd, J=10.0, 2.4 Hz, 1H), 4.67 (q, J=7.8 Hz, 1H), 3.57 (s, 6H), 3.11 (q, J=6.6 Hz, 2H), 2.13-1.93 (m, 2H), 1.76-1.51 (m, 8H), 1.54-1.36 (m, 3H), 1.37-1.07 (m, 6H), 1.01-0.84 (m, 2H); $^{13}$C NMR (75 MHz, 353 K $(CD_3)_2SO$) δ 170.6, 170.1, 167.9, 164.2, 133.7, 132.7, 131.7, 128.8, 128.4, 127.9, 126.51, 125.9, 124.8, 124.2, 123.7, 123.4, 47.8, 42.4, 37.9, 34.2, 32.1, 32.1, 30.9, 28.4, 25.5, 25.1, 22.2; HRMS (ESI-QTOF) m/z $[M+Na]^+$ calcd for $C_{32}H_{42}N_4O_4Na$; 569.3104; found 569.3213.

Synthesis of (S)-N-(1-(4-(1-naphthoyl)piperazin-1-yl)-6-acrylamido-1-oxohexan-2-yl)cyclohexanecarboxamide (35)

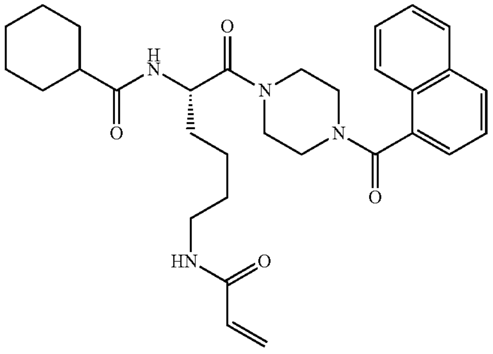 [SMILES: C=CC(=O)NCCCC[C@H](NC(=O)C1CCCCC1)C(=O)N1CCN(C(=O)c2cccc3ccccc23)CC1]

Compound 35 was prepared from Boc-deprotected 11 and cyclohexanecarboxy NHS ester 26 using general procedure D to collect 21 mg (37%) of the desired product as a white foam. $^1$H NMR (300 MHz, $CDCl_3$) δ 8.11-7.96 (m, 3H), 7.90 (dd, J=17.6, 8.1 Hz, 1H), 7.84-7.76 (m, 1H), 7.64-7.53 (m, 3H), 7.53-7.42 (m, 1H), 6.34-5.89 (m, 2H), 5.54 (t, J=11.7 Hz, 1H), 4.71 (dd, J=13.8, 6.8 Hz, 0.5H), 4.61-4.46 (m, 0.5H), 3.70 (br s, 4H), 3.54-3.36 (m, 2H), 3.19-3.01 (m, 4H), 2.33-2.05 (m, 1H), 1.81-1.04 (m, 16H). $^1$H NMR (300 MHz, 353 K $(CD_3)_2SO$) δ 8.03-7.93 (m, 2H), 7.87-7.78 (m, 1H), 7.73 (br s, 1H), 7.63-7.52 (m, 4H), 7.47 (dd, J=6.9, 1.3 Hz, 1H), 6.19 (dd, J=17.1, 10.0 Hz, 1H), 6.04 (dd, J=17.1, 2.4 Hz, 1H), 5.52 (dd, J=10.0, 2.4 Hz, 1H), 4.65 (d, J=8.0 Hz, 1H), 3.56 (br s, 6H), 3.11 (dd, J=13.2, 6.9 Hz, 2H), 2.37-2.06 (m, 1H), 1.74-1.11 (m, 18H); $^{13}$C NMR (75 MHz, 353 K $(CD_3)_2SO$) δ 174.4, 170.1, 167.9, 164.2, 133.7, 132.7, 131.7, 128.8, 128.5, 127.9, 126.5, 125.9, 124.8, 124.2, 123.7, 123.5, 47.7, 43.3, 37.9, 30.9, 28.9, 28.6, 28.4, 25.1, 24.8, 24.7, 22.1, signals for 4×C of piperazine not visible; HRMS (ESI-QTOF) m/z $[M+Na]^+$ calcd for $C_{31}H_{40}N_4O_4Na$ 555.2947; found 555.2925.

Synthesis of (S)-N-(1-(4-(1-naphthoyl)piperazin-1-yl)-6-acrylamido-1-oxohexan-2-yl)cyclopropanecarboxamide (36)

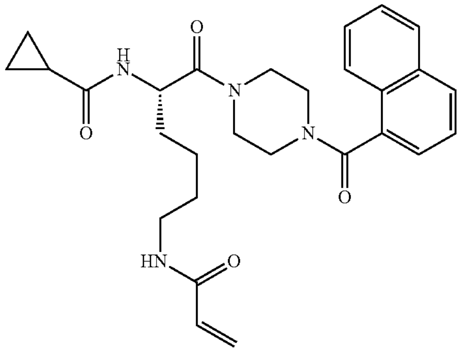 [SMILES: C=CC(=O)NCCCC[C@H](NC(=O)C1CC1)C(=O)N1CCN(C(=O)c2cccc3ccccc23)CC1]

Compound 36 was prepared from Boc-deprotected 11 and commercially available cyclopropanecarboxyl chloride (27) using general procedure E to collect 21 mg (91%) of the desired product as a white foam. $^1$H NMR (300 MHz, $(CD_3)_2SO$) δ 8.40-8.32 (m, 1H), 8.12-7.96 (m, 3H), 7.85-7.72 (m, 1H), 7.64-7.55 (m, 3H), 7.48 (d, J=7.0 Hz, 1H), 6.54-5.89 (m, 2H), 5.70-5.43 (m, 1H), 4.87-4.69 (m, 0.5H), 4.65-4.51 (m, 0.5H), 4.04-3.60 (m, 4H), 3.49-3.32 (m, 2H), 3.21-2.94 (m, 4H), 1.80-1.17 (m, 7H), 0.72-0.51 (m, 4H). $^1$H NMR (300 MHz, 353 K $(CD_3)_2SO$) δ 8.05-7.96 (m, 2H), 7.88-7.80 (m, 2H), 7.62-7.54 (m, 4H), 7.47 (dd, J=7.0, 1.3 Hz, 1H), 6.19 (dd, J=17.2, 10.1 Hz, 1H), 6.04 (dd, J=17.2, 2.4 Hz, 1H), 5.51 (dd, J=10.1, 2.4 Hz, 1H), 4.70 (q, J=7.6 Hz, 1H), 3.56 (br s, 7H), 3.27-3.06 (m, 2H), 1.93-1.13 (m, 8H), 0.79-0.41 (m, 4H); $^{13}$C NMR (75 MHz, 353 K $(CD_3)_2SO$) δ 173.7, 171.2, 169.3, 165.9, 133.8, 133.3, 131.8, 129.4, 129.3, 128.7, 127.4, 126.8, 125.6, 125.4, 124.6, 124.2, 55.90, 55.86, 49.1, 38.8, 32.0, 31.5, 29.6, 28.8, 22.7, 13.8, 6.7; HRMS (ESI-QTOF) m/z [M+Na]+ calcd for $C_{28}H_{34}N_4O_4Na$ 513.2478; found 513.2473.

Synthesis of (S)-N-(6-(4-(1-naphthoyl)piperazin-1-yl)-6-oxo-5-pivalamidohexyl)acrylamide (37)

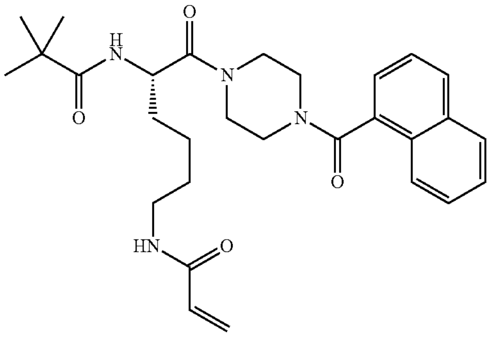 [SMILES: C=CC(=O)NCCCC[C@H](NC(=O)C(C)(C)C)C(=O)N1CCN(C(=O)c2cccc3ccccc23)CC1]

Compound 37 was prepared from Boc-deprotected 11 and commercially available t-butoxycarbonyl chloride (28) using general procedure E to collect 43 mg (76%) of the desired product as a white foam. $^1$H NMR (300 MHz, $(CD_3)_2SO$) δ 8.04 (br s, 0.5H), 8.09-7.92 (m, 2H), 7.86-7.75 (m, 1H), 7.63-7.53 (m, 3H), 7.49 (dd, J=7.0, 1.3 Hz, 1H), 7.43 (d, J=7.9 Hz, 0.5H), 6.36-5.88 (m, 2H), 5.53 (t, J=11.6 Hz, 1H), 4.72 (dd, J=13.1, 5.9 Hz, 0.5H), 4.55 (q, J=7.2 Hz, 0.5H), 3.98-3.58 (m, 4H), 3.50-3.32 (m, 3H), 3.18-2.90 (m, 4H), 1.73-1.49 (m, 2H), 1.49-1.16 (m, 4H), 1.16-1.02 (br m, 9H). $^1$H NMR (300 MHz, 353 K $(CD_3)_2SO$) δ 8.03-7.95 (m, 2H), 7.88-7.79 (m, 1H), 7.73 (br s, 1H), 7.62-7.53 (m, 3H), 7.47 (dd, J=7.0, 1.3 Hz, 1H), 7.15 (d, J=7.9 Hz, 1H), 6.19 (dd, J=17.1, 10.0 Hz, 1H), 6.03 (dd, J=17.1, 2.4 Hz, 1H), 5.51 (dd, J=10.0, 2.4 Hz, 1H), 4.68 (q, J=7.4 Hz, 1H), 3.56 (br s, 8H), 3.11 (q, J=6.6 Hz, 2H), 1.79-1.54 (m, 2H), 1.53-1.38 (m, 2H), 1.36-1.21 (m, 2H), 1.12 (s, 9H); $^{13}$C NMR (75 MHz, 353 K $(CD_3)_2SO$) δ 176.6, 170.1, 167.9, 164.2, 133.7, 132.7, 131.7, 128.8, 128.5, 127.9, 126.5, 125.9, 124.8, 124.2, 123.7, 123.4, 48.2, 37.9, 37.6, 30.7, 28.4, 26.9, 22.0, signals for 4×C of piperazine not visible; HRMS (ESI-QTOF) m/z [M+Na]+ calcd for $C_{29}H_{38}N_4O_4Na$ 529.2791; found 529.2784.

Synthesis of (S)-N-(1-(4-(1-naphthoyl)piperazin-1-yl)-6-acrylamido-1-oxohexan-2-yl)-3-methylbutanamide (38)

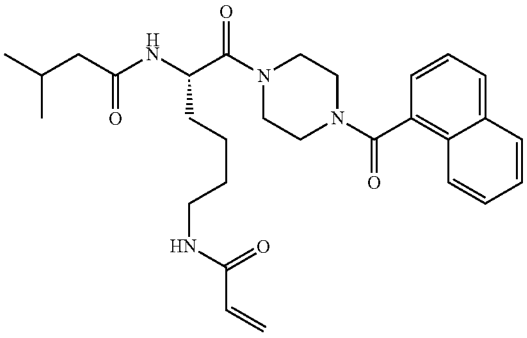 [SMILES: C=CC(=O)NCCCC[C@H](NC(=O)CC(C)C)C(=O)N1CCN(C(=O)c2cccc3ccccc23)CC1]

Compound 38 was prepared from Boc-deprotected 11 and commercially available 3-methylbutyryl chloride (29) using general procedure E to collect 52 mg (91%) of the desired product as a white foam. $^1$H NMR (300 MHz, $(CD_3)_2SO$) δ 8.10-7.96 (m, 4H), 7.87-7.71 (m, 1H), 7.64-7.52 (m, 3H), 7.49 (dd, J=7.0, 1.3 Hz, 1H), 6.38-5.93 (m, 2H), 5.54 (t, J=11.5 Hz, 1H), 4.74 (q, J=7.1 Hz, 0.5H), 4.58 (q, J=7.1 Hz, 0.5H), 4.08-3.61 (m, 4H), 3.52-3.34 (m, 2H), 3.22-2.90 (m, 4H), 2.05-1.83 (m, 3H), 1.71-1.06 (m, 6H), 0.93-0.66 (m, 6H). $^1$H NMR (300 MHz, 353 K $(CD_3)_2SO$) δ 8.04-7.95 (m, 2H), 7.86-7.79 (m, 1H), 7.75-7.66 (m, 2H), 7.61-7.53 (m, 3H), 7.47 (dd, J=7.0, 1.3 Hz, 1H), 6.19 (dd, J=17.1, 10.0 Hz, 1H), 6.04 (dd, J=17.2, 2.4 Hz, 1H), 5.52 (dd, J=10.0, 2.4 Hz, 1H), 4.68 (d, J=7.6 Hz, 1H), 3.58 (br s, 8H), 3.11 (q, J=6.6 Hz, 2H), 2.09-1.91 (m, 3H), 1.69-1.20 (m, 7H), 0.88 (d, J=6.0 Hz, 6H); $^{13}$C NMR (75 MHz, 353 K $(CD_3)_2SO$) δ 170.8, 170.1, 167.9, 164.2, 133.7, 132.7, 131.7, 128.8, 128.4, 127.9, 126.5, 125.9, 124.8, 124.2, 123.7, 123.4, 47.8, 44.0, 37.9, 30.9, 28.4, 25.0, 22.2, 21.82, 21.76; HRMS (ESI-QTOF) m/z $[M+Na]^+$ calcd for $C_{29}H_{38}N_4O_4Na$ 529.2791; found 529.2770.

Synthesis of (S)-N-(6-(4-(1-naphthoyl)piperazin-1-yl)-5-isobutyramido-6-oxohexyl)acrylamide (39)

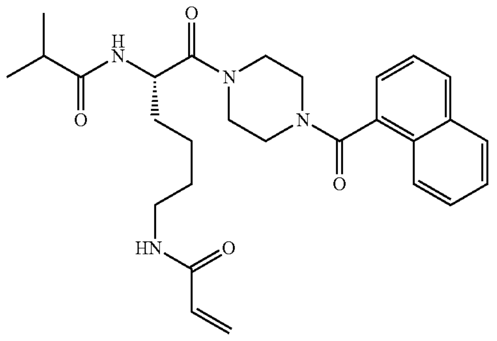 [SMILES: C=CC(=O)NCCCC[C@H](NC(=O)C(C)C)C(=O)N1CCN(C(=O)c2cccc3ccccc23)CC1]

Compound 39 was prepared from Boc-deprotected 11 and commercially available isobutyryl chloride (30) using general procedure E to collect 47 mg (85%) of the desired product as a white foam. $^1$H NMR (300 MHz, $(CD_3)_2SO$) δ 8.15-7.88 (m, 4H), 7.86-7.73 (m, 1H), 7.64-7.52 (m, 3H), 7.53-7.44 (m, 1H), 6.32-5.89 (m, 2H), 5.75-5.36 (m, 1H), 4.72 (q, J=7.6 Hz, 0.5H), 4.55 (q, J=7.9, 7.5 Hz, 0.5H), 4.00-3.60 (m, 4H), 3.55-3.33 (m, 2H), 3.21-2.93 (m, 4H), 2.47-2.28 (m, 1H), 1.73-1.12 (m, 6H), 1.10-0.73 (m, 6H). $^1$H NMR (300 MHz, 353 K $(CD_3)_2SO$) δ 8.05-7.94 (m, 2H), 7.87-7.78 (m, 1H), 7.73 (br s, 1H), 7.67-7.53 (m, 4H), 7.47 (dd, J=7.0, 1.3 Hz, 1H), 6.19 (dd, J=17.1, 10.0 Hz, 1H), 6.04 (dd, J=17.1, 2.4 Hz, 1H), 5.52 (dd, J=10.0, 2.4 Hz, 1H), 4.67 (q, J=7.3 Hz, 1H), 3.57 (br s, 8H), 3.11 (q, J=6.6 Hz, 2H), 2.48-2.31 (m, 1H), 1.77-1.37 (m, 4H), 1.36-1.20 (m, 2H), 1.00 (dd, J=8.3, 6.8 Hz, 6H); $^{13}$C NMR (75 MHz, 353 K $(CD_3)_2SO$) δ 175.4, 170.1, 167.9, 164.2, 133.7, 132.7, 131.7, 128.8, 128.4, 127.9, 126.5, 125.9, 124.8, 124.2, 123.7, 123.4, 47.7, 37.9, 33.3, 30.9, 28.4, 22.1, 19.1, 18.8; HRMS (ESI-QTOF) m/z $[M+Na]^+$ calcd for $C_{28}H_{36}N_4O_4Na$; 515.2634 found 515.2646.

Synthesis of (S)-N-(6-(4-(1-naphthoyl)piperazin-1-yl)-6-oxo-5-propionamidohexyl)acrylamide (40)

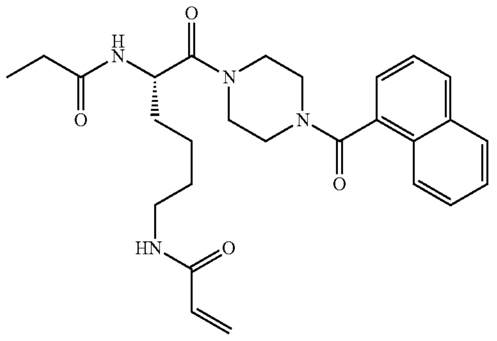 [SMILES: C=CC(=O)NCCCC[C@H](NC(=O)CC)C(=O)N1CCN(C(=O)c2cccc3ccccc23)CC1]

Compound 40 was prepared from Boc-deprotected 11 and commercially available propanoyl chloride (31) using general procedure E to collect 42 mg (79%) of the desired product as a white foam. $^1$H NMR (300 MHz, $(CD_3)_2SO$) δ 8.12-7.94 (m, 4H), 7.85-7.78 (m, 1H), 7.62-7.53 (m, 3H), 7.49 (d, J=7.0 Hz, 1H), 6.36-5.93 (m, 2H), 5.65-5.44 (m, 1H), 4.74 (q, J=7.6 Hz, 0.5H), 4.56 (q, J=7.6 Hz, 0.5H), 3.90-3.61 (m, 4H), 3.56-3.34 (m, 2H), 3.18-3.00 (m, 4H), 2.24-2.01 (m, 2H), 1.69-1.14 (m, 6H), 1.03-0.83 (m, 3H). $^{1}H$ NMR (300 MHz, 353 K $(CD_3)_2SO$) δ 8.04-7.95 (m, 2H), 7.89-7.79 (m, 1H), 7.73 (br s, 1H), 7.68 (d, J=8.0 Hz, 1H), 7.62-7.52 (m, 3H), 7.47 (dd, J=7.0, 1.3 Hz, 1H), 6.19 (dd, J=17.1, 10.0 Hz, 1H), 6.04 (dd, J=17.1, 2.4 Hz, 1H), 5.52 (dd, J=10.0, 2.4 Hz, 1H), 4.67 (dd, J=14.3, 6.5 Hz, 1H), 3.60 (br s, 8H), 3.11 (q, J=6.6 Hz, 2H), 2.25-1.98 (m, 2H), 1.71-1.38 (m, 4H), 1.37-1.18 (m, 2H), 1.00 (t, J=7.5 Hz, 3H); $^{13}C$ NMR (75 MHz, 353 K $(CD_3)_2SO$) δ 172.2, 170.1, 167.9, 164.2, 133.7, 132.7, 131.7, 128.8, 128.4, 127.9, 126.5, 125.9, 124.8, 124.2, 123.8, 123.4, 47.8, 37.9, 30.9, 28.4, 27.8, 22.2, 9.3, signals for 4×C of piperazine not visible; HRMS (ESI-QTOF) m/z $[M+Na]^+$ calcd for $C_{27}H_{34}N_4O_4Na$; 501.2478 found 501.2465.

Synthesis of (S)-N-(6-(4-(1-naphthoyl)piperazin-1-yl)-5-acetamido-6-oxohexyl)acrylamide (41)

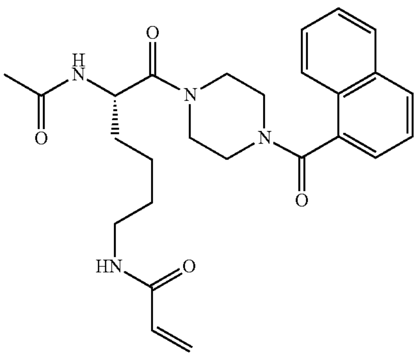 [SMILES: C=CC(=O)NCCCC[C@H](NC(C)=O)C(=O)N1CCN(C(=O)c2cccc3ccccc23)CC1]

Compound 41 was prepared from Boc-deprotected 11 and commercially available acetic anhydride (32) using general procedure E to collect 22 mg (58%) of the desired product as a white foam. $^{1}H$ NMR (300 MHz, $(CD_3)_2SO$) δ 8.17-8.04 (m, 1H), 8.05-7.97 (m, 3H), 7.86-7.66 (m, 1H), 7.61-7.53 (m, 3H), 7.53-7.38 (m, 1H), 6.38-5.92 (m, 2H), 5.61-5.46 (m, 1H), 4.73 (dd, J=14.7, 7.7 Hz, 0.5H), 4.64-4.46 (m, 0.5H), 3.95-3.55 (m, 4H), 3.50-3.15 (m, 2H), 3.24-2.90 (m, 4H), 1.98-1.72 (m, 3H), 1.63-1.17 (m, 6H). $^{1}H$ NMR (300 MHz, 353 K $(CD_3)_2SO$) δ 8.06-7.92 (m, 2H), 7.88-7.67 (m, 3H), 7.63-7.53 (m, 3H), 7.46 (d, J=1.3 Hz, 1H), 6.19 (dd, J=17.1, 10.0 Hz, 1H), 6.04 (dd, J=17.2, 2.4 Hz, 1H), 5.52 (dd, J=10.0, 2.4 Hz, 1H), 4.73-4.61 (m, 1H), 3.57 (br s, 8H), 3.11 (q, J=6.6 Hz, 2H), 1.84 (s, 3H), 1.69-1.41 (m, 4H), 1.35-1.22 (m, 2H); $^{13}C$ NMR (75 MHz, 353 K $(CD_3)_2SO$) δ 170.1, 168.4, 167.9, 164.2, 133.7, 132.7, 131.7, 128.8, 128.4, 127.9, 126.5, 125.9, 124.8, 124.2, 123.7, 123.4, 47.9, 37.9, 30.9, 28.4, 22.2, 21.8, signals for 4×C of piperazine not visible; HRMS (ESI-QTOF) m/z $[M+Na]^+$ calcd for $C_{26}H_{32}N_4O_4Na$ 487.2321; found 487.2314.

Synthesis of (S)-N-(1-(4-(1-naphthoyl)piperazin-1-yl)-6-acrylamido-1-oxohexan-2-yl)benzamide (61)

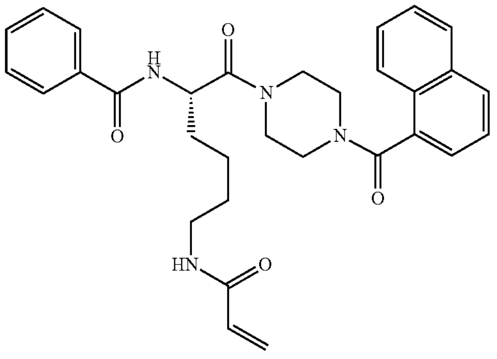 [SMILES: C=CC(=O)NCCCC[C@H](NC(=O)c1ccccc1)C(=O)N1CCN(C(=O)c2cccc3ccccc23)CC1]

Compound 61 was prepared from Boc-deprotected 11 and commercially available benzoyl chloride 42 using general procedure E to collect 19 mg (76%) of the desired product as a white foam. $^{1}H$ NMR (300 MHz, $(CD_3)_2SO$) δ 8.58 (dd, J=17.7, 7.6 Hz, 1H), 8.10 (br s, 0.5H), 8.00 (d, J=8.2 Hz, 2.5H), 7.95-7.78 (m, 3H), 7.65-7.32 (m, 7H), 6.38-5.84 (m, 2H), 5.62-5.41 (m, 1H), 4.93 (q, J=7.2 Hz, 0.5H), 4.75 (q, J=6.8 Hz, 0.5H), 4.08-3.65 (m, 4H), 3.59-3.32 (m, 1.5H), 3.26-2.87 (m, 4H), 1.84-1.59 (m, 2H), 1.52-1.17 (m, 5H). $^{1}H$ NMR (300 MHz, 353 K $(CD_3)_2SO$) δ 8.11 (br d, J=7.7 Hz, 1H), 8.07-7.93 (m, 2H), 7.91-7.78 (m, 3H), 7.70-7.32 (m, 7H), 6.18 (dd, J=17.2, 10.1 Hz, 1H), 6.03 (dd, J=17.2, 2.4 Hz, 1H), 5.50 (dd, J=10.1, 2.4 Hz, 1H), 4.89 (q, J=7.2 Hz, 1H), 3.62 (br s, 8H), 3.15 (q, J=6.5 Hz, 2H), 1.89-1.66 (m, 2H), 1.57-1.26 (m, 6H); $^{13}C$ NMR (75 MHz, 353 K $(CD_3)_2SO$) δ 170.0, 167.9, 165.8, 164.2, 133.8, 133.7, 132.7, 131.7, 130.7, 128.8, 128.4, 127.9, 127.7, 126.9, 126.5, 125.9, 124.8, 124.2, 123.7, 123.4, 48.9, 37.9, 30.6, 28.4, 22.4, signals for 4×C of piperazine not visible; HRMS (ESI-QTOF) m/z [M+Na]+ calcd for $C_{31}H_{34}N_4O_4Na$ 549.2478; found 549.2465.

Synthesis of (S)-N-(1-(4-(1-naphthoyl)piperazin-1-yl)-6-acrylamido-1-oxohexan-2-yl)-2-fluorobenzamide (62)

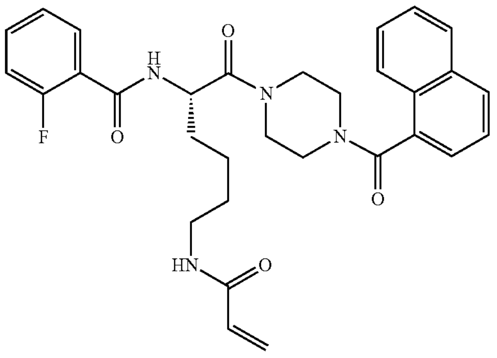 [SMILES: C=CC(=O)NCCCC[C@H](NC(=O)c1ccccc1F)C(=O)N1CCN(C(=O)c2cccc3ccccc23)CC1]

Compound 62 was prepared from Boc-deprotected 11 and commercially available 2-fluorobenzoyl chloride 43 using general procedure E to collect 20 mg (45%) of the desired product as a white foam. $^{1}H$ NMR (300 MHz, $(CD_3)_2SO$) δ

8.47 (dd, J=14.5, 7.3 Hz, 1H), 8.14-8.03 (m, 0.5H), 8.01 (d, J=8.5 Hz, 3H), 7.88-7.77 (m, 1H), 7.71-7.45 (m, 7H), 7.41-7.14 (m, 2.5H), 6.28-5.86 (m, 2H), 5.72-5.30 (m, 1H), 5.12-4.88 (m, 0.5H), 4.84-4.71 (m, 0.5H), 4.05-3.60 (m, 3H), 3.21-3.02 (m, 4H), 1.85-1.55 (m, 2H), 1.53-1.21 (m, 4H). $^{1}$H NMR (300 MHz, 353 K $(CD_3)_2SO$) δ 8.10-7.92 (m, 3H), 7.91-7.77 (m, 1H), 7.73-7.42 (m, 7H), 7.38-7.16 (m, 2H), 6.18 (dd, J=17.1, 10.1 Hz, 1H), 6.02 (dd, J=17.2, 2.4 Hz, 1H), 5.50 (dd, J=10.1, 2.3 Hz, 1H), 4.92 (dd, J=11.8, 5.1 Hz, 1H), 3.62 (br s, 8H), 3.14 (q, J=6.5 Hz, 2H), 1.88-1.61 (m, 2H), 1.55-1.30 (m, 4H); $^{19}$F NMR (283 MHz, 353 K $(CD_3)_2SO$) δ−114.2; $^{13}$C NMR (75 MHz, 353 K $(CD_3)_2SO$) δ 169.9, 168.4, 164.9, 163.2, 159.3 (d, $^{1}J_{CF}$=249 Hz), 133.8, 132.9, 132.6 (d, $^{3}J_{CF}$=8.8 Hz), 131.77, 130.0 (d, $^{4}J_{CF}$=2.8 Hz), 129.0, 128.8, 128.2, 126.9, 126.3, 125.2, 124.4, 124.4, 124.3, 123.8, 123.0, 122.8, 115.9 (d, $^{2}J_{CF}$=22.7 Hz), 49.3, 38.2, 31.0, 28.5, 22.2, signals for 4×C of piperazine not visible; HRMS (ESI-QTOF) m/z [M+Na]+ calcd for $C_{31}H_{33}FN_4O_4Na$ 567.2384; found 567.2383.

Synthesis of (S)-N-(1-(4-(1-naphthoyl)piperazin-1-yl)-6-acrylamido-1-oxohexan-2-yl)-3-fluorobenzamide (63)

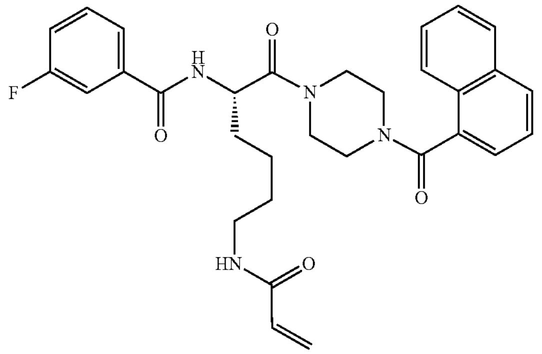 [SMILES: C=CC(=O)NCCCC[C@H](NC(=O)c1cccc(F)c1)C(=O)N1CCN(C(=O)c2cccc3ccccc23)CC1]

Compound 63 was prepared from Boc-deprotected 11 and commercially available 3-fluorobenzoyl chloride 44 using general procedure E to collect 32 mg (74%) of the desired product as a white foam. $^{1}$H NMR (300 MHz, $(CD_3)_2SO$) δ 8.69 (dd, J=16.6, 7.5 Hz, 1H), 8.15-8.04 (m, 0.5H), 8.00 (d, J=8.2 Hz, 2.5H), 7.84-7.21 (m, 10H), 6.28-5.85 (m, 2H), 5.70-5.45 (m, 1H), 4.92 (q, J=8.4, 7.9 Hz, 0.5H), 4.83-4.66 (m, 0.5H), 4.01-3.63 (m, 4H), 3.56-3.42 (m, 1.5H), 3.24-2.99 (m, 4H), 1.84-1.58 (m, 2H), 1.54-1.24 (m, 4H). $^{1}$H NMR (300 MHz, 353 K $(CD_3)_2SO$) δ 8.37 (d, J=7.7 Hz, 1H), 8.07-7.94 (m, 2H), 7.89-7.44 (m, 10H), 7.34 (tdd, J=8.5, 2.6, 1.0 Hz, 1H), 6.18 (dd, J=17.1, 10.1 Hz, 1H), 6.03 (dd, J=17.1, 2.4 Hz, 1H), 5.51 (dd, J=10.0, 2.4 Hz, 1H), 4.87 (q, J=7.2 Hz, 1H), 3.62 (br s, 8H), 3.14 (q, J=6.5 Hz, 3H), 1.75 (q, J=7.4 Hz, 2H), 1.59-1.29 (m, 4H); $^{19}$F NMR (283 MHz, 353 K $(CD_3)_2SO$) δ−113.1; $^{13}$C NMR (76 MHz, 353 K $(CD_3)_2SO$) δ 169.9, 167.9, 164.5 (d, $^{3}J_{CF}$=2.4 Hz), 164.2, 161.6 (d, $^{1}J_{CF}$=244 Hz), 136.1 (d, $^{4}J_{CF}$=6.7 Hz), 133.7, 132.7, 131.7, 129.8 (d, $^{3}J_{CF}$=8.1 Hz), 128.8, 128.5, 127.9, 126.5, 125.9, 124.8, 124.2, 123.8, 123.5, 123.1, 123.1, 117.6 (d, $^{2}J_{CF}$=21.2 Hz), 113.8 (d, $^{2}J_{CF}$=22.7 Hz), 49.1, 37.9, 30.5, 28.4, 22.4, signals for 4×C of piperazine not visible; HRMS (ESI-QTOF) m/z [M+Na]+ calcd for $C_{31}H_{33}FN_4O_4Na$ 567.2384; found 567.2399.

Synthesis of (S)-N-(1-(4-(1-naphthoyl)piperazin-1-yl)-6-acrylamido-1-oxohexan-2-yl)-4-fluorobenzamide (64)

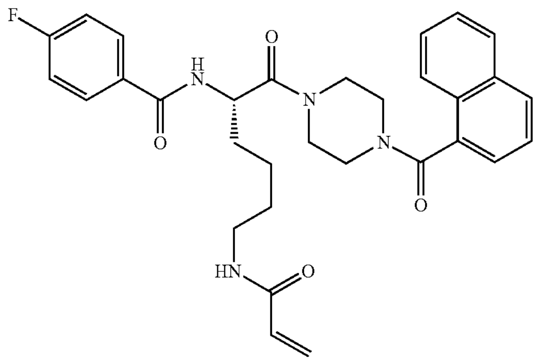 [SMILES: C=CC(=O)NCCCC[C@H](NC(=O)c1ccc(F)cc1)C(=O)N1CCN(C(=O)c2cccc3ccccc23)CC1]

Compound 64 was prepared from Boc-deprotected 11 and commercially available 4-fluorobenzoyl chloride 45 using general procedure E to collect 11 mg (25%) of the desired product as a white foam. $^{1}$H NMR (300 MHz, $(CD_3)_2SO$) δ 8.59 (dd, J=15.4, 7.3 Hz, 1H), 8.15-7.86 (m, 5H), 7.81 (d, J=6.6 Hz, 1H), 7.65-7.52 (m, 3H), 7.53-7.40 (m, 1H), 7.36-7.20 (m, 2H), 6.40-5.89 (m, 2H), 5.61-5.44 (m, 1H), 4.91 (q, J=7.1 Hz, 0.5H), 4.84-4.65 (m, 0.5H), 4.08-3.63 (m, 4H), 3.25-3.04 (m, 4H), 1.82-1.62 (m, 2H), 1.52-1.24 (m, 4H). $^{1}$H NMR (300 MHz, 353 K $(CD_3)_2SO$) δ 8.27 (d, J=7.8 Hz, 1H), 8.01-7.89 (m, 4H), 7.85-7.80 (m, 1H), 7.78-7.67 (m, 1H), 7.59-7.53 (m, 3H), 7.47 (dd, J=7.0, 1.3 Hz, 1H), 7.31-7.05 (m, 2H), 6.18 (dd, J=17.1, 10.1 Hz, 1H), 6.02 (dd, J=17.1, 2.4 Hz, 1H), 5.51 (dd, J=10.0, 2.4 Hz, 1H), 4.96-4.73 (m, 1H), 3.61 (br, 8H), 3.26-3.09 (m, 2H), 1.74 (q, J=7.5 Hz, 2H), 1.54-1.29 (m, 4H); $^{19}$F NMR (283 MHz, 353 K $(CD_3)_2SO$) δ−109.5; $^{13}$C NMR (75 MHz, 353 K $(CD_3)_2SO$) δ 170.1, 168.0, 164.91, 164.36, 163.6 (d, $^{1}J_{CF}$=249 Hz), 133.7, 132.7, 131.7, 130.3 (d, $^{4}J_{CF}$=2.8 Hz), 129.7 (d, $^{3}J_{CF}$=9.2 Hz), 128.8, 128.5, 127.9, 126.6, 126.0, 124.9, 124.3, 123.9, 123.5, 114.6 (d, $^{2}J_{CF}$=21.8 Hz), 49.1, 38.0, 30.6, 28.4, 22.4, signals for 4×C of piperazine not visible; HRMS (ESI-QTOF) m/z $[M+Na]^+$ calcd for $C_{31}H_{33}FN_4O_4Na$ 567.2384; found 567.2383.

Synthesis of (S)-N-(1-(4-(1-naphthoyl)piperazin-1-yl)-6-acrylamido-1-oxohexan-2-yl)-2-naphthamide (65)

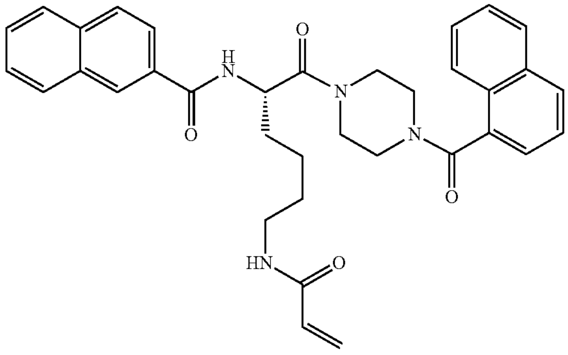 [SMILES: C=CC(=O)NCCCC[C@H](NC(=O)c1ccc2ccccc2c1)C(=O)N1CCN(C(=O)c2cccc3ccccc23)CC1]

Compound 65 was prepared from Boc-deprotected 11 and 2-naphthoyl NHS ester (46) according to procedure D to collect 23 mg (50%) of the desired product as a white foam. $^1$H NMR (300 MHz, $(CD_3)_2SO$) δ 8.73 (dd, J=15.6, 7.6 Hz, 1H), 8.49 (d, J=15.3 Hz, 1H), 8.07-7.92 (m, 9H), 7.80 (br s, 1H), 7.70-7.26 (m, 9H), 6.33-5.86 (m, 2H), 5.64-5.45 (m, 1H), 5.00 (d, J=7.3 Hz, 0.5H), 4.82 (d, J=7.3 Hz, 0.5H), 3.78 (br s, 4H), 3.23-2.98 (m, 5H), 1.88-1.64 (m, 2H), 1.59-1.26 (m, 5H). $^1$H NMR (300 MHz, 353 K $(CD_3)_2SO$) δ 8.47 (s, 1H), 8.39 (d, J=7.7 Hz, 1H), 8.06-7.88 (m, 6H), 7.85-7.77 (m, 1H), 7.75 (br s, 1H), 7.66-7.51 (m, 5H), 7.47 (dd, J=7.0, 1.4 Hz, 1H), 6.18 (dd, J=17.1, 10.1 Hz, 1H), 6.02 (dd, J=17.1, 2.4 Hz, 1H), 5.49 (dd, J=10.1, 2.4 Hz, 1H), 4.95 (q, J=9.0, 7.4 Hz, 1H), 3.65 (br s, 6H), 3.25-3.11 (m, 2H), 1.79 (q, J=7.5 Hz, 2H), 1.59-1.23 (m, 6H); $^{13}$C NMR (75 MHz, 353 K $(CD_3)_2SO$) δ 170.2, 168.0, 166.0, 164.4, 133.9, 133.7, 132.7, 131.9, 131.8, 131.1, 128.9, 128.5, 128.4, 128.0, 127.4, 127.2, 127.18, 127.16, 126.6, 126.2, 126.0, 124.9, 124.3, 123.9, 123.5, 49.1, 38.0, 30.8, 28.5, 22.5, signals for 4×C of piperazine not visible; HRMS (ESI-QTOF) m/z $[M+Na]^+$ calcd for $C_{35}H_{36}N_4O_4Na$ 599.2634; found 599.2623.

Synthesis of (S)-N-(1-(4-(1-naphthoyl)piperazin-1-yl)-6-acrylamido-1-oxohexan-2-yl)-1-naphthamide (66)

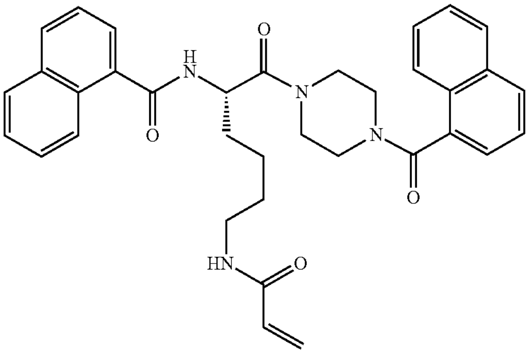 [SMILES: C=CC(=O)NCCCC[C@H](NC(=O)c1cccc2ccccc12)C(=O)N1CCN(C(=O)c2cccc3ccccc23)CC1]

Compound 66 was prepared from Boc-deprotected 11 and commercially available 1-naphthoyl chloride 2 using general procedure E to collect 29 mg (63%) of the desired product as a white foam. $^1$H NMR (300 MHz, $(CD_3)_2SO$) δ 8.72 (dd, J=16.2, 7.6 Hz, 1H), 8.25-7.74 (m, 7H), 7.70-7.38 (m, 8H), 6.34-5.89 (m, 2H), 5.65-5.37 (m, 1H), 5.10-4.94 (m, 0.5H), 4.90-4.76 (m, 0.5H), 4.15-3.42 (m, 6H), 3.27-3.01 (m, 4H), 1.85-1.60 (m, 2H), 1.54-1.37 (m, 4H). $^1$H NMR (300 MHz, 353 K $(CD_3)_2SO$) δ 8.36 (d, J=7.6 Hz, 1H), 8.32-8.16 (m, 1H), 8.03-7.87 (m, 4H), 7.89-7.79 (m, 1H), 7.76 (br s, 1H), 7.63-7.38 (m, 8H), 6.19 (dd, J=17.1, 10.1 Hz, 1H), 6.02 (dd, J=17.1, 2.4 Hz, 1H), 5.50 (dd, J=10.1, 2.3 Hz, 1H), 5.04-4.73 (m, 1H), 3.93-3.45 (br m, 6H), 3.16 (q, J=6.4 Hz, 2H), 3.01-2.80 (m, 2H), 1.87-1.63 (m, 2H), 1.57-1.44 (m, 4H); $^{13}$C NMR (75 MHz, 353 K $(CD_3)_2SO$) δ 170.0, 168.03, 168.0 164.3, 134.0, 133.7, 132.8, 132.7, 131.7, 129.6, 129.4, 128.9, 128.5, 127.9, 127.7, 126.6, 126.2, 126.0, 125.7, 124.98, 124.9, 124.9, 124.4, 124.3, 123.8, 123.5, 49.1, 38.0, 30.6, 28.5, 22.5, signals for 4×C of piperazine not visible; HRMS (ESI-QTOF) m/z $[M+Na]^+$ calcd for $C_{35}H_{36}N_{404}Na$ 599.2634; found 599.2630.

Synthesis of (S)-N-(6-(4-(1-naphthoyl)piperazin-1-yl)-6-oxo-5-(2-phenylacetamido)hexyl)acrylamide (67)

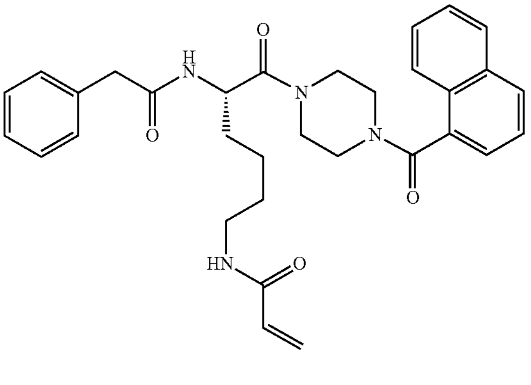 [SMILES: C=CC(=O)NCCCC[C@H](NC(=O)Cc1ccccc1)C(=O)N1CCN(C(=O)c2cccc3ccccc23)CC1]

Compound 67 was prepared from Boc-deprotected 11 and commercially available phenylacetyl chloride 47 using general procedure E to collect 24 mg (84%) of the desired product as a white foam. $^1$H NMR (300 MHz, $(CD_3)_2SO$) δ 8.38 (d, J=8.0 Hz, 1H), 8.13-7.89 (m, 3H), 7.78 (s, 1H), 7.66-7.53 (m, 3H), 7.49-7.43 (m, 1H), 7.38-7.06 (m, 5H), 6.32-5.91 (m, 2H), 5.67-5.47 (m, 1H), 4.73 (q, J=5.9, 4.2 Hz, 0.5H), 4.54 (q, J=7.4 Hz, 0.5H), 3.91-3.49 (m, 4H), 3.50-3.38 (m, 2H), 3.30-3.18 (m, 1H) 3.19-2.66 (m, 4H), 1.75-1.07 (m, 6H). $^1$H NMR (300 MHz, 353 K $(CD_3)_2SO$) δ 8.01-7.95 (m, 2H), 7.89-7.76 (m, 2H), 7.63-7.52 (m, 4H), 7.45 (dd, J=7.0, 1.3 Hz, 1H), 7.25 (d, J=4.3 Hz, 4H), 7.22-7.15 (m, 1H), 6.19 (dd, J=17.2, 10.1 Hz, 1H), 6.04 (dd, J=17.1, 2.4 Hz, 1H), 5.51 (dd, J=10.0, 2.3 Hz, 1H), 4.68 (q, J=7.7 Hz, 1H), 3.74-3.28 (m, 10H), 3.11 (q, J=6.7 Hz, 2H), 1.78-1.61 (m, 1H), 1.61-1.50 (m, 1H), 1.53-1.36 (m, 2H), 1.36-1.22 (m, 2H); $^{13}$C NMR (75 MHz, 353 K $(CD_3)_2SO$) δ 171.3, 171.0, 169.5, 166.1, 136.1, 133.9, 133.8, 133.4, 131.8, 129.5, 129.4, 129.3, 128.8, 128.6, 127.58, 126.98, 126.95, 125.73, 124.66, 124.3, 99.9, 55.9, 49.2, 42.5, 32.1, 31.4, 29.7, 28.8, 22.7; HRMS (ESI-QTOF) m/z $[M+Na]^+$ calcd for $C_{32}H_{36}N_4O_4Na$ 563.2634; found 563.2645.

Synthesis of (S)-N-(6-(4-(1-naphthoyl)piperazin-1-yl)-6-oxo-5-(3-phenylpropanamido)hexyl)acrylamide (68)

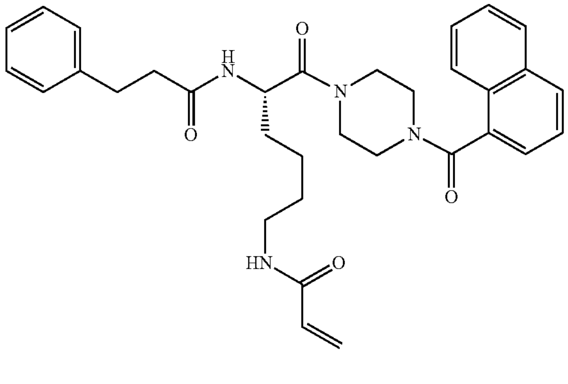 [SMILES: C=CC(=O)NCCCC[C@H](NC(=O)CCc1ccccc1)C(=O)N1CCN(C(=O)c2cccc3ccccc23)CC1]

Compound 68 was prepared from Boc-deprotected 11 and hydrocinnamoyl NHS ester (48) using general procedure D to collect 25 mg (41%) of the desired product as a white foam. $^1H$ NMR (300 MHz, $(CD_3)_2SO$) δ 8.21-7.95 (m, 4H), 7.86-7.76 (m, 1H), 7.65-7.52 (m, 3H), 7.48 (d, J=7.1 Hz, 1H), 7.33-7.08 (m, 5H), 6.29-5.94 (m, 2H), 5.63-5.43 (m, 1H), 4.74 (q, J=8.5, 7.6 Hz, 0.5H), 4.64-4.46 (m, 0.5H), 3.88-3.58 (br m, 4H), 3.34 (br s, 1H), 3.18-2.98 (m, 4H), 2.91-2.68 (m, 2H), 2.49-2.37 (m, 2H), 1.63-0.91 (m, 7H). $^1H$ NMR (300 MHz, 353 K $(CD_3)_2SO$) δ 8.08-7.93 (m, 2H), 7.89-7.77 (m, 2H), 7.73 (br s, 1H), 7.63-7.52 (m, 3H), 7.47 (dd, J=7.0, 1.3 Hz, 1H), 7.28-7.07 (m, 5H), 6.19 (dd, J=17.1, 10.0 Hz, 1H), 6.04 (dd, J=17.1, 2.4 Hz, 1H), 5.51 (dd, J=10.0, 2.4 Hz, 1H), 4.68 (br s, 1H), 3.60 (br s, 8H), 3.10 (q, J=6.7 Hz, 2H), 2.82 (t, J=7.6 Hz, 2H), 2.51-2.36 (m, 2H), 1.76-1.34 (m, 4H), 1.32-1.17 (m, 2H); $^{13}C$ NMR (75 MHz, 353 K $(CD_3)_2SO$) δ 170.6, 169.9, 167.9, 164.2, 140.8, 133.7, 132.7, 131.7, 128.8, 128.4, 127.9, 127.7, 127.6, 126.5, 125.9, 125.3, 124.8, 124.2, 123.7, 123.4, 47.8, 37.9, 36.0, 30.9, 30.5, 28.4, 22.1, signals for 4×C of piperazine not visible; HRMS (ESI-QTOF) m/z [M+Na]+ calcd for $C_{33}H_{38}N_4O_4Na$; 577.2791 found 577.2794.

Synthesis of (S)-N-(1-(4-(1-naphthoyl)piperazin-1-yl)-6-acrylamido-1-oxohexan-2-yl)-4-phenylbutanamide (69)

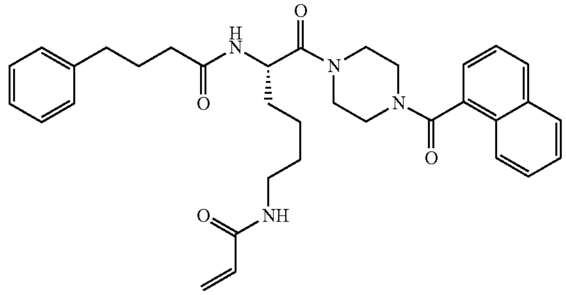 [SMILES: C=CC(=O)NCCCC[C@H](NC(=O)CCCc1ccccc1)C(=O)N1CCN(C(=O)c2cccc3ccccc23)CC1]

Compound 69 was prepared from Boc-deprotected 11 and 4-phenylbutanoyl NHS ester (49) using general procedure C to collect 24 mg (30%) of the desired product as a white foam. $^1H$ NMR (300 MHz, $(CD_3)_2SO$) δ 8.16-7.94 (m, 4H), 7.79 (td, J=7.7, 6.1, 2.7 Hz, 1H), 7.64-7.51 (m, 3H), 7.48 (d, J=7.0 Hz, 1H), 7.32-7.22 (m, 2H), 7.23-7.06 (m, 3H), 6.33-5.92 (m, 2H), 5.62-5.40 (m, 1H), 4.75 (q, J=8.3, 7.3 Hz, 0.5H), 4.63-4.51 (m, 0.5H), 3.92-3.61 (m, 4H), 3.53-3.36 (m, 2H), 3.24-2.91 (m, 4H), 2.62-2.52 (m, 2H), 2.30-1.90 (m, 2H), 1.88-1.66 (m, 2H), 1.64-1.07 (m, 6H). $^1H$ NMR (300 MHz, 353 K $(CD_3)_2SO$) δ 8.03-7.95 (m, 2H), 7.87-7.77 (m, 1H), 7.70 (br s, 2H), 7.60-7.52 (m, 3H), 7.50-7.44 (m, 1H), 7.30-7.23 (m, 2H), 7.22-7.11 (m, 3H), 6.18 (dd, J=17.1, 10.1 Hz, 1H), 6.03 (dd, J=17.1, 2.4 Hz, 1H), 5.50 (dd, J=10.0, 2.5 Hz, 1H), 4.69 (dd, J=15.0, 7.9 Hz, 1H), 3.56 (br s, 8H), 3.12 (q, J=6.6 Hz, 2H), 2.57 (t, J=7.6 Hz, 2H), 2.25-2.10 (m, 2H), 1.81 (p, J=7.5 Hz, 2H), 1.72-1.49 (m, 2H), 1.53-1.34 (m, 2H), 1.36-1.24 (m, 2H); $^{13}C$ NMR (75 MHz, 353 K $(CD_3)_2SO$) δ 171.2, 170.1, 167.9, 164.2, 141.3, 133.6, 132.6, 131.7, 128.8, 128.4, 127.8, 127.7, 127.7, 126.4, 125.9, 125.1, 124.7, 124.2, 123.6, 123.4, 47.9, 37.9, 34.2, 34.2, 30.9, 28.4, 26.4, 22.2, signals for 4×C of piperazine not visible; HRMS (ESI-QTOF) m/z [M+Na]+ calcd for $C_{34}H_{40}N_4O_4Na$; 591.2947 found 591.2947.

Synthesis of (S)-N-(6-(4-(1-naphthoyl)piperazin-1-yl)-5-(2-(4-fluorophenyl)acetamido)-6-oxohexyl) acrylamide (70)

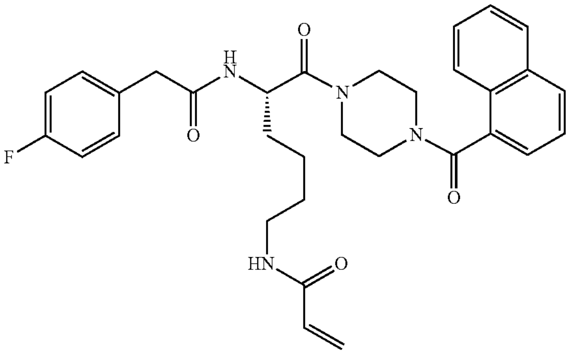 [SMILES: C=CC(=O)NCCCC[C@H](NC(=O)Cc1ccc(F)cc1)C(=O)N1CCN(C(=O)c2cccc3ccccc23)CC1]

Compound 70 was prepared from Boc-deprotected 11 and 4-fluorophenylacetyl NHS ester (50) using general procedure D to collect 34 mg (58%) of the desired product as a white foam. $^1H$ NMR (300 MHz, $CDCl_3$) δ 7.93-7.86 (m, 2H), 7.79 (d, J=16.6 Hz, 1H), 7.59-7.45 (m, 3H), 7.45-7.36 (m, 1H), 7.24-7.13 (m, 2H), 7.08-6.91 (m, 2H), 6.60 (d, J=7.7 Hz, 1H), 6.32-6.16 (m, 1H), 6.10-5.85 (m, 2H), 5.66-5.51 (m, 1H), 5.02-4.86 (m, 0.5H), 4.76 (dt, J=8.3, 4.6 Hz, 0.5H), 4.25-3.11 (m, 13H), 1.82-1.16 (m, 7H). $^1H$ NMR (300 MHz, 353 K $(CD_3)_2SO$) δ 8.05-7.92 (m, 3H), 7.85-7.77 (m, 1H), 7.72 (br s, 1H), 7.63-7.52 (m, 3H), 7.47-7.43 (m, 1H), 7.32-7.20 (m, 2H), 7.13-6.97 (m, 2H), 6.19 (dd, J=17.1, 10.0 Hz, 1H), 6.04 (dd, J=17.1, 2.5 Hz, 1H), 5.52 (dd, J=10.0, 2.5 Hz, 1H), 4.67 (s, 1H), 3.77-3.28 (br s, 8H), 1.74-1.49 (m, 3H), 1.51-1.35 (m, 2H), 1.35-1.19 (m, 3H); $^{19}F$ NMR (283 MHz, 353 K $(CD_3)_2SO$) δ−116.9; $^{13}C$ NMR (75 MHz, 353 K $(CD_3)_2SO$) δ 169.8, 169.2, 167.9, 164.2, 160.7 (d, $^1J_{CF}$=242 Hz), 133.6, 132.7, 132.0 (d, $^4J_{CF}$=3.1 Hz), 131.7, 130.3 (d, $^3J_{CF}$=8.1 Hz), 128.8, 128.4, 127.9, 126.5, 125.9, 124.8, 124.2, 123.8, 123.4, 114.3 (d, $^2J_{CF}$=21.3 Hz), 48.0, 40.7, 37.9, 30.9, 28.4, 22.1, signals for 4×C of piperazine not visible; HRMS (ESI-QTOF) m/z [M+Na]+ calcd for $C_{32}H_{35}FN_4O_4Na$ 581.2540; found 581.2545.

Synthesis of (S)-N-(6-(4-(1-naphthoyl)piperazin-1-yl)-5-(2-(3-fluorophenyl)acetamido)-6-oxohexyl) acrylamide (71)

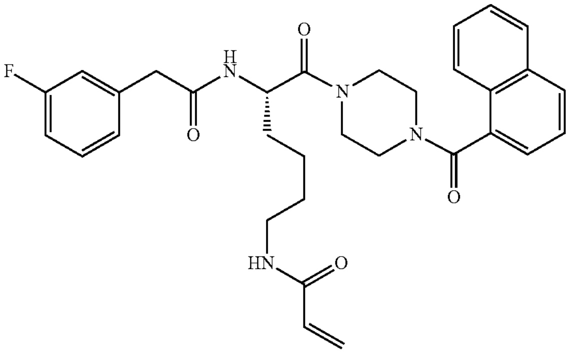 [SMILES: C=CC(=O)NCCCC[C@H](NC(=O)Cc1cccc(F)c1)C(=O)N1CCN(C(=O)c2cccc3ccccc23)CC1]

Compound 71 was prepared from Boc-deprotected 11 and 3-fluorophenylacetyl NHS ester (51) using general procedure D to collect 48 mg (82%) of the desired product as a white foam. $^1$H NMR (300 MHz, $(CD_3)_2SO$) δ 8.44-8.34 (m, 1H), 8.08-7.95 (m, 3H), 7.78 (br s, 1H), 7.65-7.52 (m, 3H), 7.47 (d, J=6.9 Hz, 1H), 7.39-7.27 (m, 1H), 7.19-6.93 (m, 3H), 6.34-5.91 (m, 2H), 5.74-5.46 (m, 1H), 4.74 (q, J=7.6 Hz, 0.5H), 4.56 (q, J=7.5 Hz, 0.5H), 3.91-3.34 (m, 7H), 3.20-2.93 (m, 4H), 1.78-1.06 (m, 7H); $^{19}$F NMR (283 MHz, 353 K $(CD_3)_2SO$) δ−113.9. $^1$H NMR (300 MHz, 353 K $(CD_3)_2SO$) δ 8.07 (d, J=7.9 Hz, 1H), 8.02-7.95 (m, 2H), 7.85-7.78 (m, 1H), 7.73 (br s, 1H), 7.60-7.53 (m, 3H), 7.45 (dd, J=6.9, 1.3 Hz, 1H), 7.37-7.21 (m, 1H), 7.13-6.93 (m, 3H), 6.19 (dd, J=17.1, 10.0 Hz, 1H), 6.04 (dd, J=17.1, 2.4 Hz, 1H), 5.52 (dd, J=10.0, 2.4 Hz, 1H), 4.68 (br s, 1H), 3.50 (br s, 8H), 3.10 (q, J=6.9 Hz, 2H), 1.80-1.14 (m, 7H); $^{19}$F NMR (283 MHz, 353 K $(CD_3)_2SO$) δ−114.0; $^{13}$C NMR (75 MHz, 353 K $(CD_3)_2SO$) δ 169.8, 168.8, 167.8, 164.2, 161.7 (d, $^1J_{CF}$=243 Hz), 138.6 (d, $^3J_{CF}$=7.8 Hz), 133.6, 132.7, 131.7, 129.4 (d, $^3J_{CF}$=8.3 Hz), 128.79, 128.44, 127.89, 126.51, 125.95, 124.79, 124.6 (d, $^4J_{CF}$=2.8 Hz), 124.2, 123.7, 123.4, 115.2 (d, $^2J_{CF}$=21.5 Hz), 112.6 (d, $^2J_{CF}$=20.9 Hz), 48.1, 41.2, 37.9, 30.9, 28.4, 22.1, signals for 4×C of piperazine not visible; HRMS (ESI-QTOF) m/z $[M+Na]^+$ calcd for $C_{32}H_{35}FN_4O_4Na$ 581.2540 found 581.2560.

Synthesis of (S)-N-(6-(4-(1-naphthoyl)piperazin-1-yl)-5-(2-(2-fluorophenyl)acetamido)-6-oxohexyl) acrylamide (72)

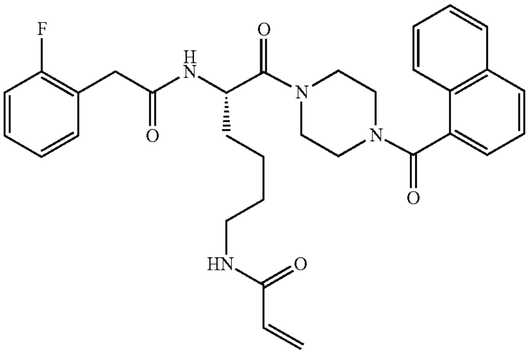

Compound 72 was prepared from Boc-deprotected 11 and 2-fluorophenylacetyl NHS ester (52) using general procedure D to collect 49 mg (83%) of the desired product as a white foam. $^1$H NMR (300 MHz, $(CD_3)_2SO$) δ 8.40 (t, J=7.1 Hz, 1H), 8.08 (t, J=5.4 Hz, 0.5H), 8.06-7.97 (m, 2.5H), 7.82-7.74 (m, 1H), 7.64-7.53 (m, 3H), 7.48 (dd, J=6.9, 1.3 Hz, 1H), 7.38-6.99 (m, 5H), 6.31-5.94 (m, 2H), 5.67-5.46 (m, 1H), 4.75 (q, J=7.5 Hz, 0.5H), 4.57 (q, J=7.6 Hz, 0.5H), 3.98-3.43 (m, 7H), 3.19-2.94 (m, 4H), 1.71-1.18 (m, 7H); $^{19}$F NMR (283 MHz, $(CD_3)_2SO$) δ−117.3, −117.4. $^1$H NMR (300 MHz, 353 K $(CD_3)_2SO$) δ 8.08-7.93 (m, 3H), 7.85-7.77 (m, 1H), 7.74 (br s, 1H), 7.63-7.51 (m, 3H), 7.46 (dd, J=7.0, 1.2 Hz, 1H), 7.36-6.97 (m, 4H), 6.19 (dd, J=17.1, 10.0 Hz, 1H), 6.04 (dd, J=17.1, 2.4 Hz, 1H), 5.52 (dd, J=10.0, 2.4 Hz, 1H), 4.69 (d, J=7.4 Hz, 1H), 3.54 (br s, 4H), 3.25-2.94 (m, 6H), 1.83-1.14 (m, 7H); $^{19}$F NMR (283 MHz, 353 K $(CD_3)_2SO$) δ−117.3; $^{13}$C NMR (75 MHz, 353 K $(CD_3)_2SO$) δ 169.8, 168.2, 167.9, 164.2, 160.2 (d, $^1J_{CF}$=244 Hz), 133.6, 132.7, 131.7, 131.1 (d, $^3J_{CF}$=4.6 Hz), 128.8, 128.4, 128.0 (d, $^3J_{CF}$=8.1 Hz), 127.9, 126.5, 125.9, 124.8, 124.2, 123.8, 123.6 (d, $^4J_{CF}$=3.3 Hz), 123.4, 122.8 (d, $^2J_{CF}$=15.8 Hz), 114.4 (d, $^2J_{CF}$=21.8 Hz), 48.1, 37.9, 34.60, 34.57, 30.9, 28.4, 22.1; HRMS (ESI-QTOF) m/z $[M+Na]^+$ calcd for $C_{32}H_{35}FN_4O_4Na$ 581.2540; found 581.2547.

Synthesis of (S)-N-(6-(4-(1-naphthoyl)piperazin-1-yl)-5-(2-(3-chlorophenyl)acetamido)-6-oxohexyl) acrylamide (73)

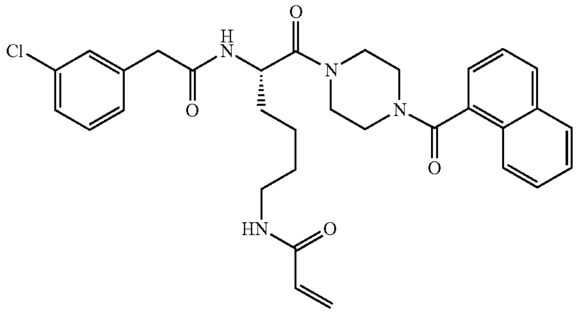 [SMILES: C=CC(=O)NCCCC[C@H](NC(=O)Cc1cccc(Cl)c1)C(=O)N1CCN(C(=O)c2cccc3ccccc23)CC1]

Compound 73 was prepared from Boc-deprotected 11 and 3-chlorophenylacetyl NHS ester (53) using general procedure D to collect the desired product as a white foam in 75% yield. $^1$H NMR (500 MHz, $CDCl_3$) δ 7.94-7.86 (m, 2H), 7.86-7.75 (m, 1H), 7.58-7.47 (m, 3H), 7.47-7.37 (m, 1H), 7.31-7.07 (m, 4H), 7.04-6.93 (m, 1H), 6.31-6.11 (m, 2H), 6.04 (ddd, J=24.0, 16.9, 10.3 Hz, 1H), 5.65-5.51 (m, 1H), 5.03-4.66 (m, 1H), 4.20-3.61 (m, 4H), 3.59-3.30 (m, 4H), 3.31-3.08 (m, 4H), 1.79-1.36 (m, 4H), 1.37-1.18 (m, 2H); $^{13}$C NMR (126 MHz, $CDCl_3$) δ 170.4, 170.2, 169.6, 165.8, 136.7, 134.4, 133.4, 133.2, 130.8, 130.0, 129.6, 129.2, 128.6, 127.4, 126.6, 126.2, 125.2, 124.3, 124.0, 48.4, 46.6, 45.4, 42.8, 42.1, 41.4, 38.7, 32.3, 28.6, 22.1; HRMS (ESI-QTOF) m/z $[M+Na]^+$ calcd for $C_{32}H_{35}C_1N_4O_4Na$ 597.2242; found 597.2245.

Synthesis of (S)-N-(6-(4-(1-naphthoyl)piperazin-1-yl)-5-(2-(2-methylphenyl)acetamido)-6-oxohexyl) acrylamide (74)

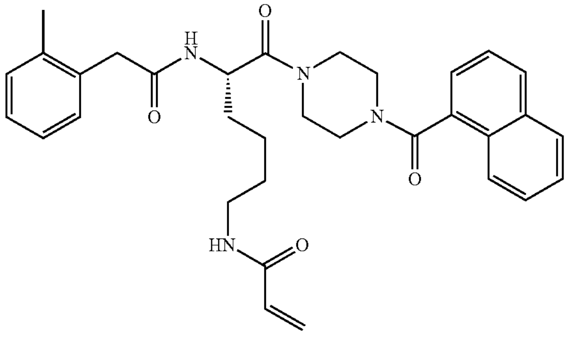 [SMILES: C=CC(=O)NCCCC[C@H](NC(=O)Cc1ccccc1C)C(=O)N1CCN(C(=O)c2cccc3ccccc23)CC1]

Compound 74 was prepared from Boc-deprotected 11 and 2-methylphenylacetyl NHS ester (54) using general procedure D to collect the desired product as a white foam in 89% yield. $^1$H NMR (500 MHz, $CDCl_3$) δ 7.91 (t, J=7.5 Hz, 2H), 7.83-7.78 (m, 1H), 7.55-7.49 (m, 3H), 7.45-7.50 (m, 1H), 7.21-7.19 (m, 4H), 6.48 (d, J=7.9 Hz, 1H), 6.29-6.01 (m, 3H), 5.60-5.53 (m, 1H), 4.98-4.76 (dtd, J=90.8, 8.3, 4.4 Hz, 1H), 4.16-3.73 (m, 3H), 3.66-3.52 (m, 4H), 3.46-3.32 (m, 1H), 3.28-3.18 (m, 4H), 2.29 (d, J=12.8 Hz, 3H), 1.71-1.44 (m, 4H), 1.34-1.21 (m, 2H); $^{13}C$ NMR (126 MHz, $CDCl_3$) δ 170.8, 170.2, 169.6, 165.7, 136.8, 133.4, 133.2, 133.0, 131.0, 130.7, 130.3, 129.6, 128.6, 127.8, 127.3, 126.6, 126.1, 125.1, 124.3, 124.0, 48.2, 46.7, 45.4, 42.5, 41.8, 41.4, 38.8, 32.5, 28.5, 22.1, 19.5; HRMS (ESI-QTOF) m/z [M+Na]+ calcd for $C_{33}H_{38}N_4O_4Na$ 577.2798; found 577.2791.

Synthesis of (S)-N-(6-(4-(1-naphthoyl)piperazin-1-yl)-5-(2-(2-methoxyphenyl)acetamido)-6-oxohexyl) acrylamide (75)

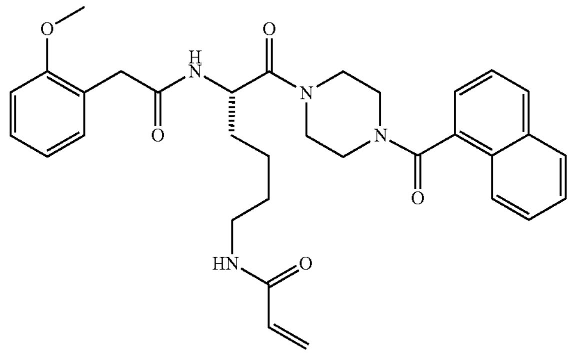 [SMILES: C=CC(=O)NCCCC[C@H](NC(=O)Cc1ccccc1OC)C(=O)N1CCN(C(=O)c2cccc3ccccc23)CC1]

Compound 75 was prepared from Boc-deprotected 11 and 2-methoxyphenylacetyl NHS ester (55) using general procedure D to collect the desired product as a white foam in 83% yield. $^1H$ NMR (500 MHz, $CDCl_3$) δ 7.94-7.91 (m, 2H), 7.85-7.79 (m, 1H), 7.58-7.51 (m, 3H), 7.46-7.40 (m, 1H), 7.32-7.17 (m, 2H), 6.98-6.90 (m, 2H), 6.79-6.76 (m, 1H), 6.26 (dd, J=30.8, 16.4 Hz, 1H), 6.11-6.00 (m, 2H), 5.59 (dd, J=20.6, 10.3 Hz, 1H), 4.97-4.75 (m, 1H), 4.14-3.95 (m, 1H), 3.86 (s, 3H), 3.77-3.48 (m, 4H), 3.41-3.13 (m, 6H), 1.72-1.45 (m, 4H), 1.35-1.25 (m, 2H); $^{13}C$ NMR (126 MHz, $CDCl_3$) δ 171.3, 170.2, 169.6, 165.7, 157.0, 133.5, 133.2, 131.1, 130.8, 129.6, 130.0, 128.6, 127.3, 126.6, 126.0, 125.1, 124.4, 124.0, 123.2, 121.0, 110.6, 55.3, 48.0, 47.0, 45.3, 42.4, 42.0, 41.4, 38.8, 32.7, 28.1, 22.0; HRMS (ESI-QTOF) m/z $[M+Na]^+$ calcd for $C_{33}H_{38}N_4O_5Na$ 593.2736; found 593.2740.

Synthesis of (S)-N-(6-(4-(1-naphthoyl)piperazin-1-yl)-5-(2-(2-chlorophenyl)acetamido)-6-oxohexyl) acrylamide (76)

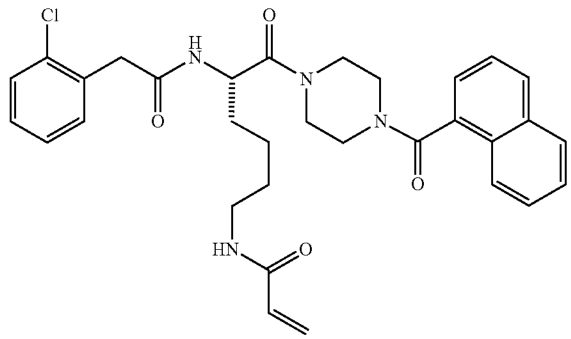

Compound 76 was prepared from Boc-deprotected 11 and 2-chlorophenylacetyl NHS ester (56) using general procedure D to collect the desired product as a white foam in 79% yield. $^1H$ NMR (500 MHz, $CDCl_3$) δ 7.94-7.85 (m, 2H), 7.86-7.77 (m, 1H), 7.56-7.47 (m, 3H), 7.44-7.31 (m, 2H), 7.25-7.23 (m, 2H), 6.73 (d, J=7.7 Hz, 1H), 6.30-6.13 (m, 2H), 6.01 (ddd, J=26.4, 17.0, 10.2 Hz, 1H), 5.61-5.49 (m, 1H), 4.88 (m, 1H), 4.13-3.81 (m, 2H), 3.79-3.50 (m, 4H), 3.49-3.12 (m, 5H), 1.75-1.39 (m, 4H), 1.39-1.19 (m, 2H); $^{13}C$ NMR (126 MHz, $CDCl_3$) δ 170.3, 170.2, 169.7, 165.7, 134.3, 133.4, 133.2, 132.7, 131.7, 131.0, 129.7, 129.0, 128.6, 127.3, 126.6, 126.0, 125.1, 124.3, 124.0, 48.3, 46.6, 45.4, 42.5, 41.8, 41.2, 39.0, 32.5, 28.4, 22.1; HRMS (ESI-QTOF) m/z $[M+Na]^+$ calcd for $C_{32}H_{35}C_1N_4O_4Na$ 597.2233; found 597.2245.

Synthesis of (S)-N-(6-(4-(1-naphthoyl)piperazin-1-yl)-5-(2-(2-bromophenyl)acetamido)-6-oxohexyl) acrylamide (77)

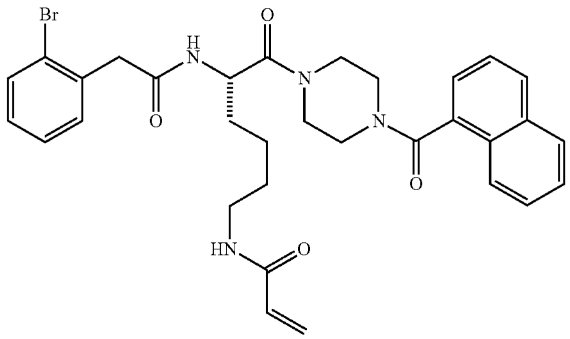 [SMILES: C=CC(=O)NCCCC[C@H](NC(=O)Cc1ccccc1Cl)C(=O)N1CCN(C(=O)c2cccc3ccccc23)CC1]

Compound 77 was prepared from Boc-deprotected 11 and 2-bromophenylacetyl NHS ester (57) using general procedure D to collect the desired product as a white foam in 88% yield. $^1H$ NMR (500 MHz, $CDCl_3$) δ 7.95-7.89 (m, 2H), 7.87-7.79 (m, 1H), 7.61-7.50 (m, 4H), 7.44 (dt, J=13.8, 6.9 Hz, 1H), 7.38-7.29 (m, 2H), 7.21-7.16 (m, 1H), 6.57 (m, 1H), 6.31-6.18 (m, 1H), 6.02 (ddd, J=29.7, 19.0, 11.6 Hz, 2H), 5.64-5.54 (m, 1H), 5.04-4.77 (m, 1H), 4.20-3.81 (m, 2H), 3.80-3.51 (m, 4H), 3.48-3.13 (m, 5H), 1.79-1.44 (m, 4H), 1.44-1.26 (m, 2H); $^{13}C$ NMR (126 MHz, $CDCl_3$) δ 170.2, 170.1, 179.5, 165.7, 133.5, 133.2, 133.1, 131.7, 130.8, 129.6, 129.3, 128.6, 128.0, 127.3, 126.6, 126.1, 125.1, 125.0, 124.3, 124.0, 48.2, 46.7, 45.4, 44.0, 42.5, 41.4, 39.0, 32.6, 28.3, 22.1; HRMS (ESI-QTOF) m/z [M+Na]+ calcd for $C_{32}H_{35}BrN_4O_4Na$ 641.1743; found 641.1739.

Synthesis of (S)-N-(6-(4-(1-naphthoyl)piperazin-1-yl)-5-(2-(2,3-dichlorophenyl)acetamido)-6-oxo-hexyl)acrylamide (78)

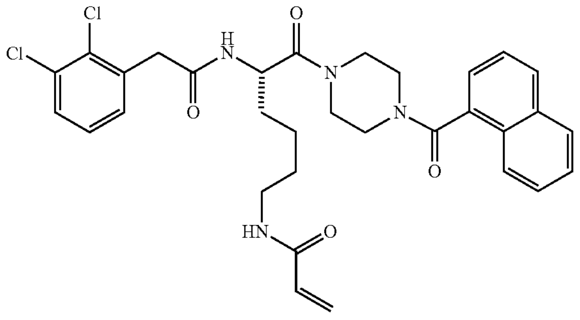 [SMILES: C=CC(=O)NCCCC[C@H](NC(=O)Cc1cccc(Cl)c1Cl)C(=O)N1CCN(C(=O)c2cccc3ccccc23)CC1]

Compound 78 was prepared from Boc-deprotected 11 and 2,3-dichlorophenylacetyl NHS ester (58) using general procedure D to collect the desired product as a white foam in 71% yield. $^1$H NMR (500 MHz, $CDCl_3$) δ 7.94-7.86 (m, 2H), 7.87-7.75 (m, 1H), 7.58-7.47 (m, 3H), 7.40 (ddd, J=14.9, 9.9, 5.5 Hz, 2H), 7.27-7.12 (m, 2H), 6.87 (d, J=8.3 Hz, 1H), 6.30-6.12 (m, 2H), 6.08-5.89 (m, 1H), 5.65-5.29 (m, 1H), 4.88 (dtd, J=88.0, 8.4, 4.4 Hz, 1H), 4.19-3.82 (m, 2H), 3.81-3.68 (m, 3H), 3.69-3.33 (m, 2H), 3.33-3.13 (m, 4H), 1.63-1.43 (m, 4H), 1.39-1.26 (m, 2H); $^{13}$C NMR (126 MHz, $CDCl_3$) δ 170.3, 169.6, 169.2, 165.8, 135.1, 133.4, 133.2, 132.7, 130.7, 130.0, 129.6, 129.4, 128.6, 127.6, 127.3, 126.6, 126.2, 125.2, 124.3, 124.0, 48.4, 46.7, 45.4, 42.5, 42.0, 41.4, 38.8, 32.4, 28.5, 22.1; HRMS (ESI-QTOF) m/z [M+Na]+ calcd for $C_{32}H_{34}Cl_2N_4O_4Na$ 631.1855; found 631.1840.

Synthesis of (S)-N-(6-(4-(1-naphthoyl)piperazin-1-yl)-5-(2-(3,4-dichlorophenyl)acetamido)-6-oxo-hexyl)acrylamide (79)

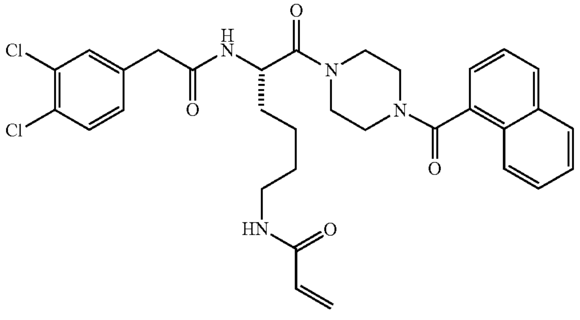 [SMILES: C=CC(=O)NCCCC[C@H](NC(=O)Cc1ccc(Cl)c(Cl)c1)C(=O)N1CCN(C(=O)c2cccc3ccccc23)CC1]

Compound 79 was prepared from Boc-deprotected 11 and 3,4-dichlorophenylacetyl NHS ester (59) using general procedure D to collect the desired product as a white foam in 69% yield. $^1$H NMR (500 MHz, $CDCl_3$) δ 7.91 (q, J=5.5, 3.7 Hz, 2H), 7.87-7.76 (m, 1H), 7.58-7.49 (m, 3H), 7.40 (ddt, J=18.3, 12.2, 7.2 Hz, 3H), 7.20-7.05 (m, 1H), 6.90 (dd, J=15.1, 7.9 Hz, 1H), 6.31-6.16 (m, 1H), 6.03 (ddd, J=26.3, 15.9, 9.7 Hz, 2H), 5.63-5.56 (m, 1H), 4.85 (dtd, J=90.0, 8.2, 4.4 Hz, 1H), 4.20-3.58 (m, 4H), 3.55-3.45 (m, 2H), 3.43-3.11 (m, 5H), 1.84-1.40 (m, 4H), 1.40-1.20 (m, 2H); $^{13}$C NMR (126 MHz, $CDCl_3$) δ 170.3, 169.8, 169.6, 165.7, 134.8, 133.4, 133.2, 132.6, 131.4, 131.1, 130.7, 130.6, 129.6, 128.6, 127.3, 126.6, 126.3, 125.2, 124.4, 124.0, 48.5, 46.7, 46.0, 45.4, 42.1, 41.4, 38.7, 32.3, 28.6, 22.1; HRMS (ESI-QTOF) m/z $[M+Na]^+$ calcd for $C_{32}H_{34}Cl_2N_4O_4Na$ 631.1855; found 631.1838.

Synthesis of (S)-N-(6-(4-(1-naphthoyl)piperazin-1-yl)-5-(2-(2,4-difluorophenyl)acetamido)-6-oxohexyl) acrylamide (80)

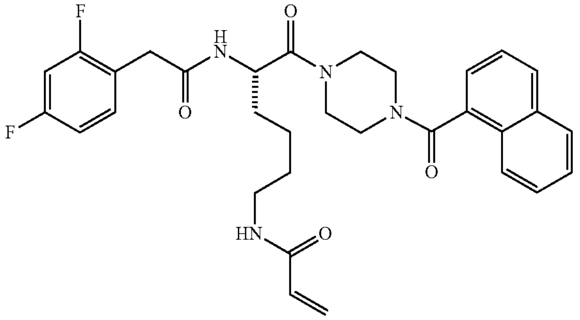 [SMILES: C=CC(=O)NCCCC[C@H](NC(=O)Cc1ccc(F)cc1F)C(=O)N1CCN(C(=O)c2cccc3ccccc23)CC1]

2,4-Difluorophenylacetic acid (60) (40 mg, 0.230 mmol) was dissolved in 0.5 mL DMF and HBTU (87 mg, 0.230 mmol) and DIPEA (100 μL, 0.576 mmol) were added. The solution was stirred for 20 min at 0° C. upon which the TFA salt of amine 11 (103 mg, 0.192 mmol) was dissolved in 0.5 mL DMF with DIPEA (33 μL, 0.192 mmol) and added to the reaction. The solution was stirred for 16 h at room temperature. Upon completion the reaction mixture was concentrated under reduced pressure. The resulting orange oil was diluted with ethyl acetate and washed with 1 M HCl, water, saturated sodium bicarbonate solution, brine, and dried over anhydrous magnesium sulfate. The solution was filtered and concentrated under reduced pressure to afford the crude oil product. The crude oil was purified by chromatography over silica (elution with 5% methanol in dichloromethane) to afford 28 mg (26%) of amide 80 as a white solid. $^1$H NMR (600 MHz, $CDCl_3$) δ 7.93-7.73 (m, 3H), 7.56-7.47 (m, 3H), 7.42 (dt, J=13.5, 7.3 Hz, 1H), 7.26 (s, 2H), 6.91-6.76 (m, 2H), 6.62 (d, J=7.6 Hz, 1H), 6.34-6.14 (m, 1H), 6.06-5.81 (m, 2H), 5.63-5.53 (m, 1H), 4.99-4.73 (m, 1H), 4.17-3.78 (m, 3H), 3.77-3.15 (m, 14H), 1.78-1.20 (m, 7H). $^{13}$C NMR (151 MHz, $CDCl_3$) δ 170.33, 169.72, 165.87, 165.82, 162.52 (dd, $^{1,3}J_{CF}$=249.1, 12.2 Hz), 161.04 (dd, $^{1,3}J_{CF}$=248.2, 12.9 Hz), 133.63, 133.35, 132.37, 130.85, 129.80, 129.61, 128.77, 127.47, 126.81, 126.46, 125.33, 124.51, 124.12, 117.91 (d, $^2J_{CF}$=20.0 Hz), 111.74 (d, $^2J_{CF}$=21.0 Hz), 104.24 (t, $^2J_{CF}$=25.2 Hz), 48.69, 47.22, 46.84, 46.13, 45.57, 42.73, 42.28, 41.90, 41.60, 38.97, 36.27, 32.75, 28.70, 22.13. HRMS (ESI-QTOF) m/z [M+Na]+ calcd for $C_{32}H_{34}F_2N_4O_4Na$ 599.2431; found 599.2446.

Synthesis of (S)-N-(6-(4-(1-naphthoyl)piperazin-1-yl)-5-(2-(2-trifluoromethylphenyl)acetamido)-6-oxohexyl)acrylamide (81)

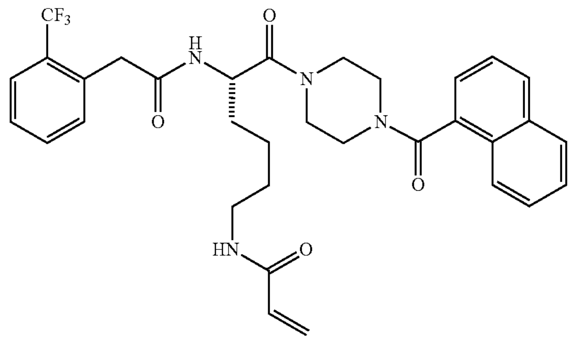 [SMILES: C=CC(=O)NCCCC[C@H](NC(=O)Cc1ccccc1C(F)(F)F)C(=O)N1CCN(C(=O)c2cccc3ccccc23)CC1]

Commercially available 2-trifluoromethylphenylacetic acid (88 mg, 0.431 mmol) was dissolved in 0.75 mL DMF and HATU (154 mg, 0.430 mmol) and DIPEA (150 μL, 0.861 mmol) were added. The solution was stirred for 20 min at 0° C. upon which the TFA salt of amine 11 (154 mg, 0.287 mmol) was dissolved in 0.4 mL DMF with DIPEA (50 μL, 0.287 mmol) and added to the reaction. The solution was stirred for 16 h at room temperature. Upon completion the reaction mixture was concentrated under reduced pressure. The resulting orange oil was diluted with ethyl acetate and washed with 1 M HCl, water, saturated sodium bicarbonate solution, brine, and dried over anhydrous magnesium sulfate. The solution was filtered and concentrated under reduced pressure to afford the crude oil product. The crude oil was purified by chromatography over silica (elution with 5% methanol in dichloromethane) to afford 90 mg (52%) of amide 81 as a white solid. $^{1}H$ NMR (600 MHz, $CDCl_3$) δ 7.91-7.73 (m, 3H), 7.68-7.58 (m, 1H), 7.56-7.44 (m, 4H), 7.44-7.31 (m, 3H), 6.64 (d, J=8.1 Hz, 1H), 6.26-6.14 (m, 1H), 6.11-5.87 (m, 2H), 5.57-5.47 (m, 1H), 4.99-4.73 (m, 1H), 4.15-3.12 (m, 19H), 1.75-1.20 (m, 7H). $^{13}C$ NMR (151 MHz, $CDCl_3$) δ 172.82, 170.39, 169.87, 165.85, 133.51, 133.26, 132.72, 132.25, 131.93, 130.84, 129.68, 128.80 (q, $^{2}J_{CF}$=30.2 Hz), 128.67, 127.63, 127.36, 126.71, 126.29 (q, $^{3}J_{CF}$=5.5 Hz), 126.12, 125.23, 124.44, 124.38, 124.37 (q, $^{1}J_{CF}$=273.5 Hz), 124.01, 48.60, 47.17, 46.74, 46.05, 45.46, 42.56, 42.16, 41.83, 41.49, 40.04, 38.82, 32.52, 28.59, 22.07. HRMS (ESI-QTOF) m/z $[M+Na]^+$ calcd 631.2508 for $C_{33}H_{35}F_3N_4O_4Na$; found 631.2493.

Synthesis of (S)-N-(6-(4-(1-naphthoyl)piperazin-1-yl)-5-(5-(dimethylamino)naphthalene-1-sulfonamido)-6-oxohexyl)acrylamide (87)

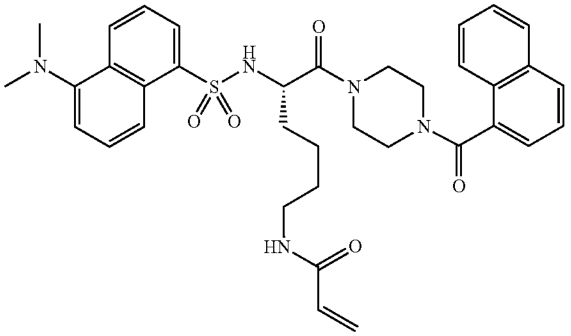 [SMILES: C=CC(=O)NCCCC[C@H](NS(=O)(=O)c1cccc2c(N(C)C)cccc12)C(=O)N1CCN(C(=O)c2cccc3ccccc23)CC1]

Compound 87 was prepared from Boc-deprotected 11 and commercially available dansyl chloride 82 using general procedure F to collect 31 mg (56%) of the desired product as a yellow foam. $^{1}H$ NMR (300 MHz, $(CD_3)_2SO$) δ 8.45 (d, J=8.5 Hz, 1H), 8.31 (t, J=9.5 Hz, 1H), 8.17 (d, J=7.3 Hz, 1H), 8.11-7.84 (m, 4H), 7.76-7.71 (m, 1H), 7.71-7.48 (m, 5H), 7.42 (t, J=6.7 Hz, 1H), 7.24 (d, J=7.6 Hz, 1H), 6.30-5.90 (m, 2H), 5.62-5.45 (m, 1H), 4.16 (t, J=7.5 Hz, 0.5H), 3.98 (t, J=7.3 Hz, 0.5H), 3.79-3.18 (m, 12H), 3.01-2.86 (m, 2H), 2.84-2.63 (m, 2H), 1.52-1.32 (m, 2H), 1.29-0.99 (m, 4H). $^{1}H$ NMR (300 MHz, 353 K $(CD_3)_2SO$) δ 8.47 (d, J=8.6 Hz, 1H), 8.35 (d, J=8.6 Hz, 1H), 8.13 (d, J=7.2 Hz, 1H), 8.03-7.94 (m, 2H), 7.79-7.72 (m, 1H), 7.68 (br s, 1H), 7.65-7.49 (m, 5H), 7.41 (dd, J=7.0, 1.2 Hz, 1H), 7.24 (d, J=7.5 Hz, 1H), 6.17 (dd, J=17.1, 10.0 Hz, 1H), 6.01 (dd, J=17.1, 2.5 Hz, 1H), 5.50 (dd, J=10.0, 2.4 Hz, 1H), 4.09 (br s, 1H), 3.60-2.80 (br s, 14H), 2.94 (q, J=6.4 Hz, 2H), 1.58-1.33 (m, 2H), 1.31-1.02 (m, 4H), signal for 1×NH is not visible; 13C NMR (75 MHz, 353 K $(CD_3)_2SO$) δ 168.9, 167.8, 164.1, 150.9, 136.2, 133.5, 132.7, 131.7, 129.0, 128.9, 128.8, 128.7, 128.5, 127.97, 127.92, 127.2, 126.5, 126.0, 124.8, 124.1, 123.7, 123.4, 122.8, 119.1, 114.7, 51.9, 44.6, 37.8, 31.6, 28.0, 21.8, signals for 4×C of piperazine not visible; HRMS (ESI-QTOF) m/z $[M+Na]^+$ calcd for $C_{36}H_{41}N_{50}O_5SNa$ 678.2726; found 678.2710.

Synthesis of (S)-N-(6-(4-(1-naphthoyl)piperazin-1-yl)-6-oxo-5-phenylmethylsulfonamido)hexyl)acrylamide (88)

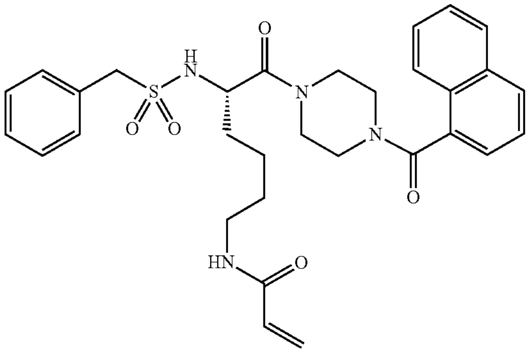 [SMILES: C=CC(=O)NCCCC[C@H](NS(=O)(=O)Cc1ccccc1)C(=O)N1CCN(C(=O)c2cccc3ccccc23)CC1]

Compound 88 was prepared from amine 11 and commercially available benzylsulfonyl chloride 83 using general procedure F to collect 39.6 mg (53%) of the desired product as a white foam. $^1$H NMR (400 MHz, $CDCl_3$) δ 7.91 (d, J=8.3 Hz, 2H), 7.87-7.77 (m, 1H), 7.64-7.48 (m, 3H), 7.45-7.29 (m, 6H), 6.34-5.95 (m, 2H), 5.95-5.82 (m, 1H), 5.68-5.50 (m, 2H), 4.31 (t, J=14.4 Hz, 1H), 4.25-4.09 (m, 1H), 4.06-3.62 (m, 3H), 3.58-3.43 (m, 1H), 3.40-3.07 (m, 5H), 3.02-2.70 (m, 8H); $^{13}$C NMR (100 MHz, $(CD_3)_2SO$) δ 169.8, 167.9, 164.2, 133.6, 132.7, 131.7, 130.3, 129.8, 128.8, 128.5, 127.9, 127.7, 127.5, 126.5, 125.9, 124.8, 124.2, 123.8, 123.5, 58.5, 51.9, 37.9, 32.0, 28.3, 21.8, signals for 4×C of piperazine not visible; HRMS (ESI-QTOF) m/z $[M+Na]^+$ calcd for $C_{31}H_{36}N_4O_5SNa$ 599.2304; found 599.2311.

Synthesis of (S)-N-(6-(4-(1-naphthoyl)piperazin-1-yl)-6-oxo-5-(phenylsulfonamido)hexyl)acrylamide (89)

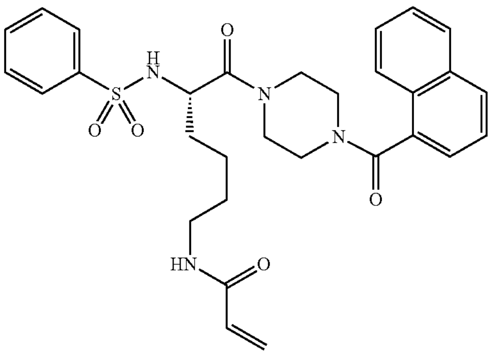 [SMILES: C=CC(=O)NCCCC[C@H](NS(=O)(=O)c1ccccc1)C(=O)N1CCN(C(=O)c2cccc3ccccc23)CC1]

Compound 89 was prepared from amine 11 and commercially available benzenesulfonyl chloride 84 using general procedure F to collect 50 mg (65%) of the desired product as a white foam. $^1$H NMR (300 MHz, 353 K $(CD_3)_2SO$) δ 8.02-7.92 (m, 2H), 7.79-7.70 (m, 3H), 7.67 (br s, 1H), 7.61-7.38 (m, 9H), 6.15 (dd, J=17.2, 10.0 Hz, 1H), 6.00 (dd, J=17.2, 2.6 Hz, 1H), 5.48 (dd, J=10.0, 2.4 Hz, 1H), 4.10 (br s, 1H), 3.33 (br s, 8H), 1.57-1.15 (m, 8H); $^{13}$C NMR (75 MHz, 353 K $(CD_3)_2SO$) δ 168.8, 167.9, 164.2, 140.8, 133.6, 132.7, 131.8, 131.7, 128.8, 128.6, 128.5, 128.4, 128.0, 127.9, 126.5, 126.2, 126.0, 124.8, 124.1, 123.8, 123.4, 51.8, 37.9, 31.6, 28.1, 21.9, signals for 4×C of piperazine not visible; HRMS (ESI-QTOF) m/z [M+Na]+ calcd for $C_{30}H_{34}N_4O_5SNa$ 585.2148; found 585.2169.

Synthesis of (S)-N-(6-(4-(1-naphthoyl)piperazin-1-yl)-5-(ethylsulfonamido)-6-oxohexyl)acrylamide (90)

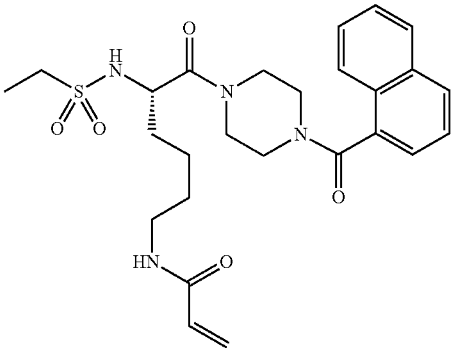 [SMILES: C=CC(=O)NCCCC[C@H](NS(=O)(=O)CC)C(=O)N1CCN(C(=O)c2cccc3ccccc23)CC1]

Compound 90 was prepared from amine 11 and commercially available ethanesulfonyl chloride 85 using general procedure F to collect 43.6 mg (66%) of the desired product as a white foam. $^1$H NMR (400 MHz, $CDCl_3$) δ 7.93-7.85 (m, 2H), 7.86-7.76 (m, 1H), 7.59-7.47 (m, 3H), 7.47-7.37 (m, 1H), 6.32-5.79 (m, 3H), 5.67-5.50 (m, 1H), 5.48-5.39 (m, 1H), 4.41-3.52 (m, 6H), 3.44-3.16 (m, 6H), 3.06-2.75 (m, 2H), 1.65-1.24 (m, 8H); $^{13}$C NMR (75 MHz, $(CD_3)_2SO$) δ 170.0, 167.9, 164.2, 133.6, 132.7, 131.7, 128.8, 128.5, 127.9, 126.5, 125.9, 124.8, 124.2, 123.8, 123.5, 51.8, 46.8, 37.9, 31.8, 28.3, 21.9, 7.4, signals for 4×C of piperazine not visible; HRMS (ESI-QTOF) m/z $[M+Na]^+$ calcd for $C_{26}H_{34}N_4O_5SNa$ 537.2148; found 537.2153.

Synthesis of (S)-N-(6-(4-(1-naphthoyl)piperazin-1-yl)-5-(methylsulfonamido)-6-oxohexyl)acrylamide (91)

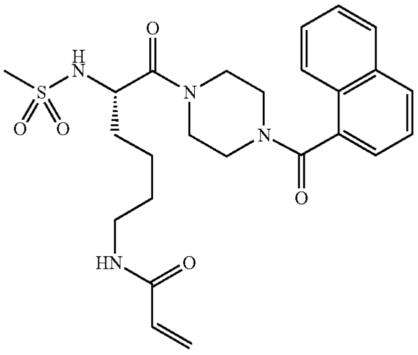 [SMILES: C=CC(=O)NCCCC[C@H](NS(C)(=O)=O)C(=O)N1CCN(C(=O)c2cccc3ccccc23)CC1]

Compound 91 was prepared from amine 11 and commercially available methylsulfonyl chloride 86 using general procedure F to collect 20 mg (48%) of the desired product as a white foam. $^1$H NMR (300 MHz, $(CD_3)_2SO$) δ 8.15-8.05 (m, 0.5H), 8.06-7.97 (m, 2H), 7.87-7.78 (m, 1H), 7.65-7.52 (m, 3H), 7.54-7.43 (m, 1H), 7.34 (d, J=8.6 Hz, 1H), 6.36-5.92 (m, 2H), 5.61-5.46 (m, 1H), 4.35 (q, J=7.4 Hz, 0.5H), 4.16 (q, J=7.3 Hz, 0.5H), 3.86-3.64 (m, 4H), 3.39 (br s, 2H), 3.19-2.99 (m, 4H), 2.83 (d, J=14.8 Hz, 3H), 1.64-1.20 (m, 6H). $^1$H NMR (300 MHz, 353 K $(CD_3)_2SO$) δ 8.03-7.94 (m, 2H), 7.87-7.80 (m, 1H), 7.75 (br s, 1H), 7.64-7.52 (m, 3H), 7.48 (dd, J=7.0, 1.3 Hz, 1H), 6.94 (br s, 1H), 6.19 (dd, J=17.1, 10.1 Hz, 1H), 6.04 (dd, J=17.1, 2.4 Hz, 1H), 5.52 (dd, J=10.0, 2.4 Hz, 1H), 4.27 (br s, 1H), 3.59 (br s, 8H), 3.13 (q, J=6.4 Hz, 2H), 2.86 (s, 3H), 1.74-1.27 (m, 6H); $^{13}C$ NMR (75 MHz, 353 K $(CD_3)_2SO$) δ 169.8, 167.9, 164.2, 133.6, 132.7, 131.7, 128.8, 128.5, 127.9, 126.6, 126.0, 124.8, 124.2, 123.8, 123.5, 51.9, 40.7, 37.9, 31.7, 28.3, 22.0, signals for 4×C of piperazine not visible; HRMS (ESI-QTOF) m/z $[M+Na]^+$ calcd for $C_{25}H_{32}N_4O_5SNa$ 523.1991 found 523.1993.

Example 6. Pharmacokinetic Properties

Inhibitor compounds were evaluated through in vitro pharmacokinetic tests performed at Pharmaron, Inc. Inhibitor 74 displayed kinetic solubility of 39 μM, which is less than an order of magnitude higher than that predicted by the Estimated SOLubility method (Delaney, J. S. ESOL: Estimating Aqueous Solubility Directly from Molecular Structure. *J. Chem. Inf Comp. Sci.* 2004, 44, 1000-1005. https://doi.org/10.1021/ci034243x). As shown in Table 6, the plasma stability displayed by both inhibitors 72 and 74 was excellent. While both of these inhibitors showed significant protein binding, as expected from their hydrophobicity, the excellent recovery showed this binding is reversible. The metabolic stabilities of inhibitors 72 and 74 were also evaluated in a human hepatocyte model. Results are shown in Table 6. The half-lives and calculated intrinsic clearance shown in Table 6 are indicative of moderate stability.

Passive diffusion across a lipid membrane was measured by PAMPA for both inhibitors 72 and 74. The values shown in Table 6 indicate both compounds were at least moderately permeant. MDCK cells were also used as a model for permeability, but both inhibitors exhibited lower apical to basolateral diffusion, and higher basolateral diffusion than expected from the PAMPA assay. Under these conditions, both inhibitors showed problematic efflux ratios of >50. However, when the same assays were performed in the presence of a Pgp inhibitor, the diffusion rates were found to align very closely to those measured in the PAMPA assay, and the efflux ratio of each inhibitor dropped to ~1. This result suggests the inhibitor compounds are most likely substrates of the Pgp transport protein, and N-methylation of their amide groups may be necessary to decrease their affinity and increase their equilibrium intracellular concentration (Seelig, A.; Landwojtowicz, E. Structure-Activity Relationship of P-Glycoprotein Substrates and Modifiers. *Eur. J. Pharm. Sci.* 2000, 12, 31-40. https://doi.org/10.1016/s0928-0987(00)00177-9).

TABLE 6

Pharmacokinetic properties of inhibitors 72 and 74.

| PK Parameter | 72 | 74 |
|---|---|---|
| Plasma t½ (min) | 1075 | 568 |
| Hepatocyte t½ (min) | 584 | 251 |
| Hepatocyte $CL_{int}$ (μL/min/$10^6$ cells) | 2.37 | 5.58 |
| Protein Binding (%) | 84 | 85 |
| Protein Binding Recovery (%) | 86 | 93 |
| PAMPA −Log [$P_e$ ($10^{-6}$ cm/s)] | 5.44 | 5.03 |
| MDCK − MDR1 $P_{app\ (A \rightarrow B)}$ ($10^{-6}$ cm/s) | 0.29 | 0.32 |
| MDCK − MDR1 $P_{app\ (B \rightarrow A)}$ ($10^{-6}$ cm/s) | 18.2 | 16.5 |
| MDCK − MDR1 Efflux Ratio | 61.7 | 51.6 |
| MDCK + Pgp Inh $P_{app\ (A \rightarrow B)}$ ($10^{-6}$ cm/s) | 2.2 | 3.2 |
| MDCK + Pgp Inh $P_{app\ (B \rightarrow A)}$ ($10^{-6}$ cm/s) | 2.8 | 3.0 |
| MDCK + Pgp Inh Efflux Ratio | 1.3 | 0.93 |

TABLE 6-continued

Example 7. Cellular Activity

Several inhibitor compounds were identified as being efficient inhibitors of TG2 in an in vitro biochemical assay, with acceptable pharmacokinetic properties, as discussed above. Four of the most active inhibitors (compounds 72, 74, 76 and 77) were therefore selected for evaluation in a cellular assay, to test the correlation between biochemical and biological activity.

Figure 4:
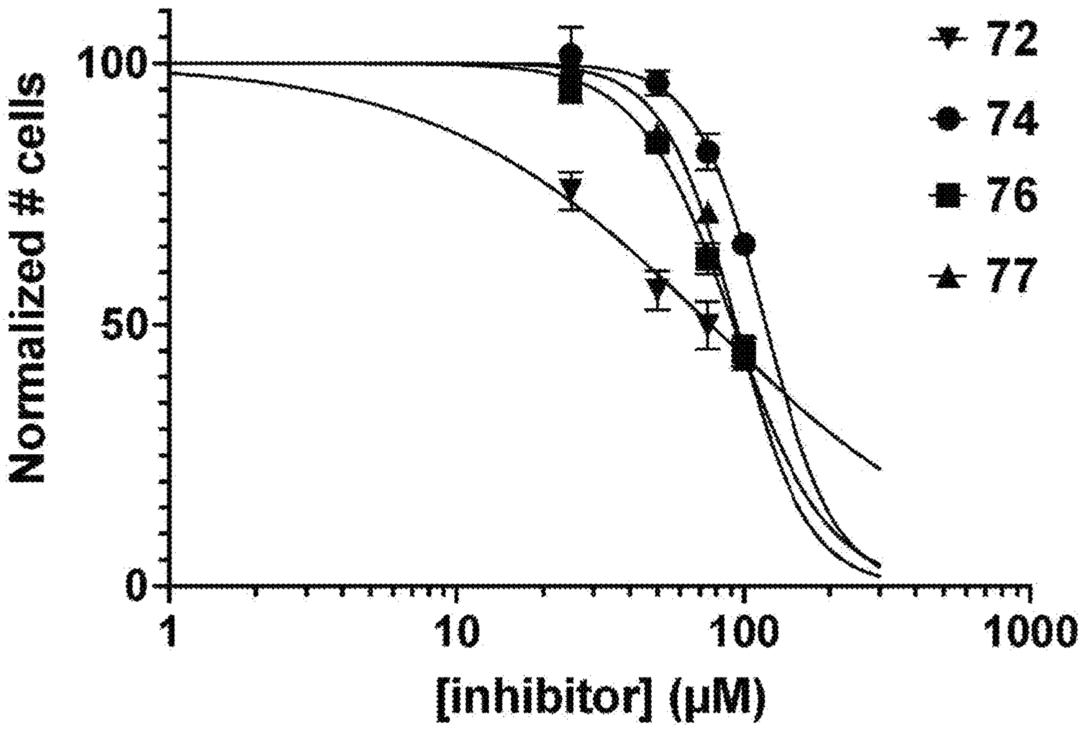
FIG. 4 shows a dose-response curve for inhibition of ECS invasion by TG2 inhibitor compounds 72, 74, 76 and 77. The $EC_{50}$ values for the inhibitors tested herein were 77±5, 119±5, 92±2 and 94±2 μM, respectively.

One well-known property of tumour-initiating cells associated with cancer metastasis is the enhanced ability to invade Matrigel (collagen). For example, it has been shown that epidermal cancer stem (ECS) cells invade Matrigel more efficiently than non-stem cancer cells, and that these properties are associated with enhanced tumour formation (Adhikary, G. et al., *PLoS ONE* 2013, 8, e84324. https://doi.org/10.1371/journal.pone.0084324). We have shown previously that ~20 μM of NC9 and 3.9 μM of VA4 can reduce ECS cell invasion through Matrigel by ~50% relative to vehicle-treated cells (Akbar, A. et al., *J. Med. Chem.* 2017, 60, 7910-7927. https://doi.org/10.1021/acs.jmedchem.7b01070; Fisher, M. L. et al., *Oncotarget* 2015, 6, 20525-20539. https://doi.org/10.18632/oncotarget.3890). Inhibitors 72, 74, 76 and 77 were evaluated using this same assay, over a concentration range of 0-100 μM, representing the approximate limit of solubility. As shown in FIG. 4, all four inhibitors were capable of inhibiting ECS cell invasion in a dose-dependent manner. Inhibitor 72, the most efficient inhibitor in biochemical assays, also showed the most potency in the cellular assay, with an EC50 value of 77 μM.

Materials and Methods for cell invasion data. To measure cell invasion, Matrigel (Corning, catalogue no. 354234) was diluted to 250 μg/mL and 120 μL was added to the upper chambers of a Transwell plate (Corning, no. 353097, 1-cm diameter, 8-μm pore size) and allowed to solidify. SCC-13 cells were suspended in spheroid medium (Fisher, M. L. et al., *Cancer Res.* 2016, 76, 7265-7275. https://doi.org/10.1158/0008-5472.can-16-2032; Adhikary, G. et al., *Carcinogenesis* 2015, 36, 800-810. https://doi.org/10.1093/carcin/bgv064) containing 1% foetal calf serum (FCS), and 20,000 cells were plated into each upper chamber atop the Matrigel. The bottom chamber contained spheroid medium supplemented with 10% FCS and 0-100 μM of inhibitor. After incubation for 18 h in a 37° C. incubator, cells in the top chamber were removed with a swab and cells on the lower surface of the membrane were fixed with 4% paraformaldehyde and the nuclei were stained with 4',6-diamidino-2-phenylindole. Cell number was counted in multiple fields (n=4) using a fluorescence microscope, normalized with respect to the number counted in the presence of vehicle only, and expressed as mean±standard deviation. These data were then fitted to a two-parameter sigmoidal curve using GraphPad Prism (maximum fixed at 100, minimum set at 0), providing the lines shown in FIG. 4.

Although this invention is described in detail with reference to embodiments thereof, these embodiments are offered to illustrate but not to limit the invention. It is possible to make other embodiments that employ the principles of the invention and that fall within its spirit and scope as defined by the claims appended hereto.

The contents of all documents and references cited herein are hereby incorporated by reference in their entirety.

What is claimed is:

1. A compound of Formula I, or a pharmaceutically acceptable salt thereof:

Formula I

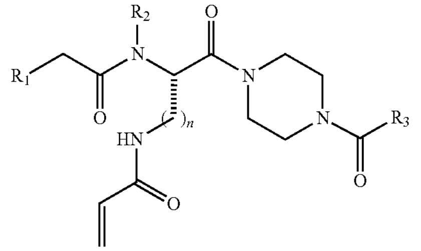

wherein:

$R_1$ is substituted or unsubstituted aryl or substituted or unsubstituted heteroaryl;

$R_2$ is hydrogen or substituted or unsubstituted $C_{1-6}$ alkyl;

$R_3$ is substituted or unsubstituted aryl or substituted or unsubstituted heteroaryl; and n is 1, 2, 3, or 4;

provided that, when $R_1$ is phenyl; $R_2$ is hydrogen; and n is 4, $R_3$ is not 4-fluorophenyl, 4-nitrophenyl or 6-chloro-2-pyridinyl.

2. The compound or pharmaceutically acceptable salt of claim 1, wherein $R_1$ is substituted or unsubstituted aryl, optionally wherein $R_1$ is substituted by hydroxyl, amino, carboxyl, sulfonate, carboxylic ester, amide, carbamate, or aminoalkyl.

3. The compound or pharmaceutically acceptable salt of claim 1, wherein $R_1$ is selected from:

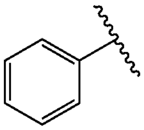 , 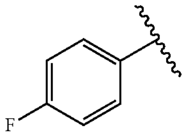 , 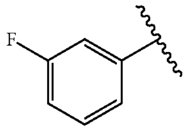 ,

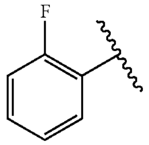 , 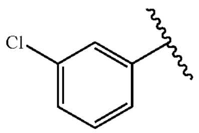 , 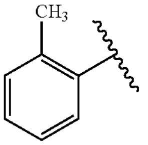 ,

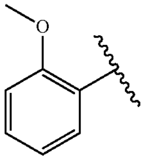 , 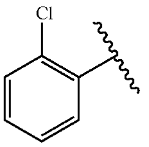 , 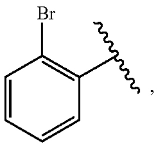 ,

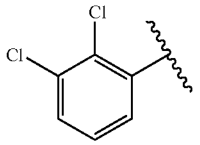 , 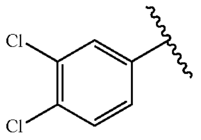 , and

-continued

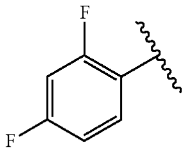 .

4. The compound or pharmaceutically acceptable salt of claim 1, wherein:

$R_2$ is hydrogen, substituted or unsubstituted $C_{1-6}$ alkyl; and/or $R_3$ is:

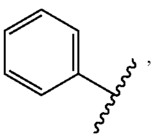 , 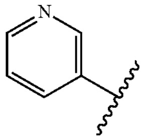 , 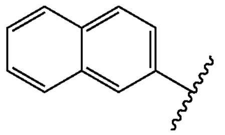 ,

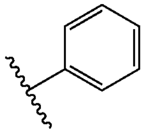 , 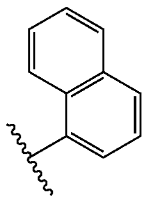 , 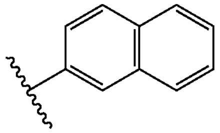 ,

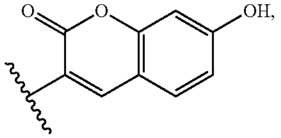

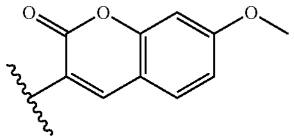 , or 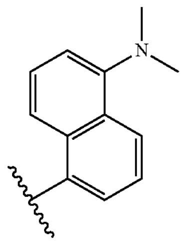 .

5. The compound or pharmaceutically acceptable salt of claim 1, wherein n is 4.

6. The compound or pharmaceutically acceptable salt of claim 1, wherein the compound is any one of compounds 67 and 70-81 as shown:

67

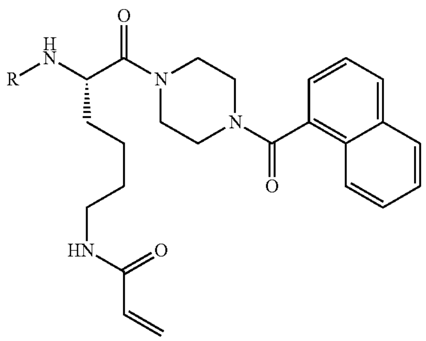

wherein R is

-continued
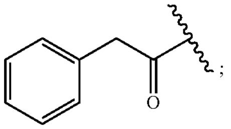
70
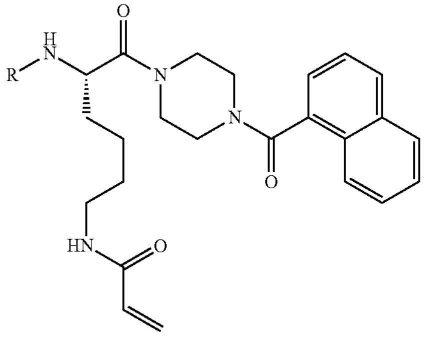
wherein R is
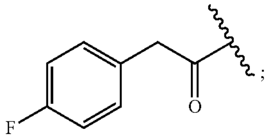
71
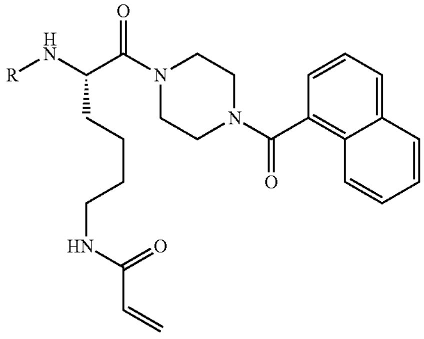
wherein R is
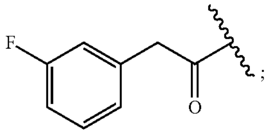
72
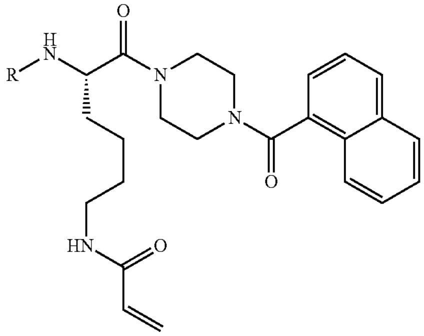
wherein R is
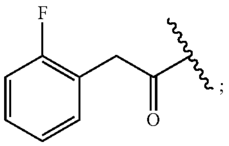
-continued
73
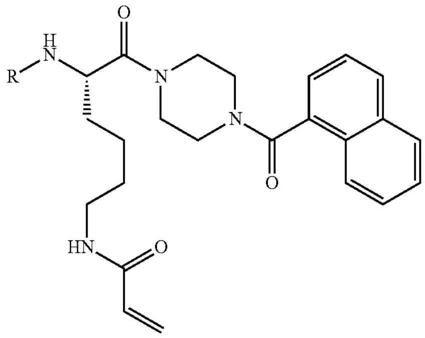
wherein R is
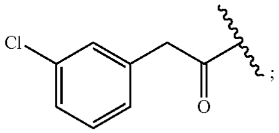
74
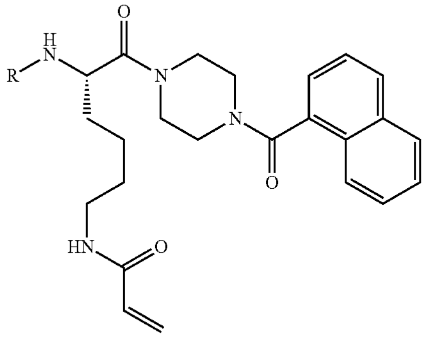
wherein R is
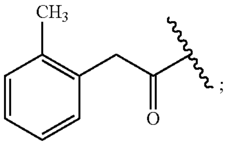
75
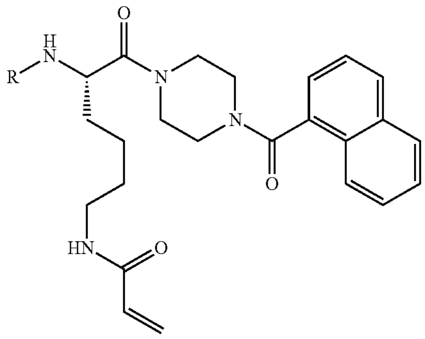
wherein R is
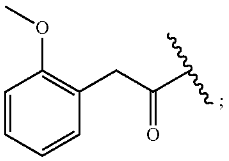

-continued
76
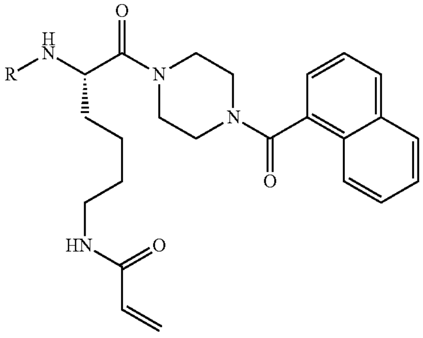
wherein R is
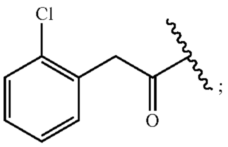
77
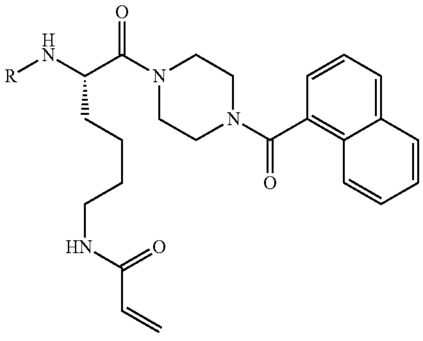
wherein R is
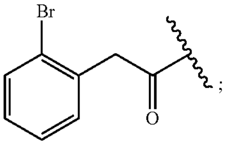
78
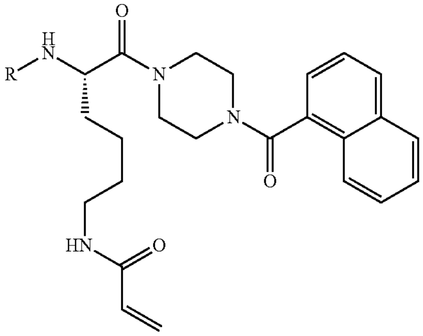
wherein R is
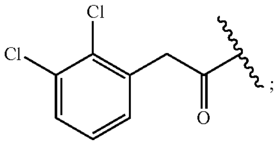
-continued
79
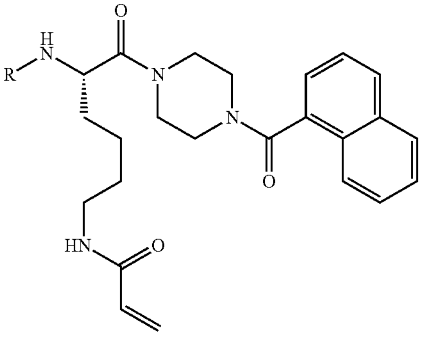
wherein R is
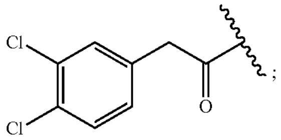
80
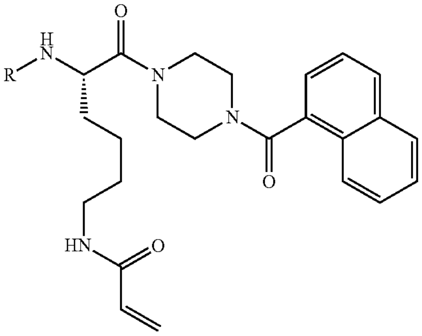
wherein R is
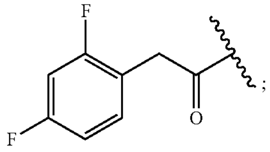
or
81
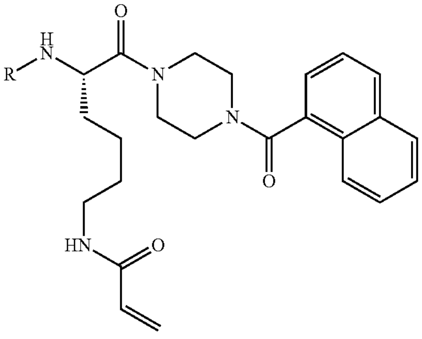
wherein R is
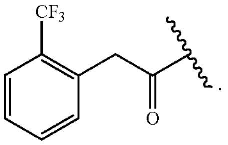
7. The compound or pharmaceutically acceptable salt of claim 4, wherein $R_2$ is substituted or unsubstituted methyl (Me).

8. A compound of Formula II, or a pharmaceutically acceptable salt thereof:

Formula II

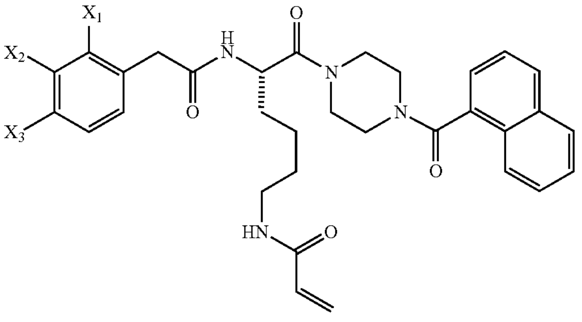

wherein:

$X_1$, $X_2$ and $X_3$ are independently selected from hydrogen, halogen, substituted or unsubstituted $C_{1-6}$ alkyl, and substituted or unsubstituted $C_{1-6}$ alkoxy.

9. The compound or pharmaceutically acceptable salt of claim 8, wherein:

$X_1$ is hydrogen, halogen, substituted or unsubstituted $C_{1-6}$ alkyl, or substituted or unsubstituted $C_{1-6}$ alkoxy, and $X_2$ and $X_3$ are hydrogen; or, $X_2$ is hydrogen, halogen, substituted or unsubstituted $C_{1-6}$ alkyl, or substituted or unsubstituted $C_{1-6}$ alkoxy, and $X_1$ and $X_3$ are hydrogen; or, $X_3$ is hydrogen, halogen, substituted or unsubstituted $C_{1-6}$ alkyl, or substituted or unsubstituted $C_{1-6}$ alkoxy, and $X_1$ and $X_2$ are hydrogen.

10. The compound or pharmaceutically acceptable salt of claim 8, wherein:

$X_1$, $X_2$ and $X_3$ are hydrogen;

$X_1$ and $X_2$ are halogen and $X_3$ is hydrogen;

$X_1$ and $X_3$ are halogen and $X_2$ is hydrogen; or $X_2$ and $X_3$ are halogen and $X_1$ is hydrogen.

11. The compound or pharmaceutically acceptable salt of claim 9, wherein:

$X_1$ is F, Cl, Br, Me, or OMe;

$X_2$ is F, Cl or Br; and/or $X_3$ is F, Cl or Br.

12. A compound of Formula III, or a pharmaceutically acceptable salt thereof:

Formula III

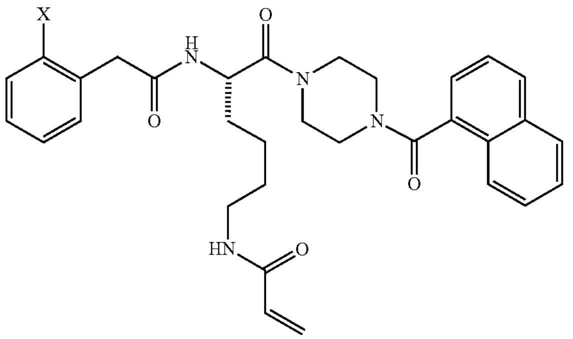

wherein:

X is hydrogen, halogen, substituted or unsubstituted $C_{1-6}$ alkyl, or substituted or unsubstituted $C_{1-6}$ alkoxy.

13. The compound or pharmaceutically acceptable salt of claim 12, wherein X is F, Cl, Br, Me, $CF_3$, or OMe.

14. A pharmaceutical composition comprising the compound of claim 1 or a pharmaceutically acceptable salt thereof, and a pharmaceutically acceptable carrier.

15. A method of treating a TG2-associated disease or disorder in a subject in need thereof, comprising administering to the subject an effective amount of the compound of claim 1 or a pharmaceutically acceptable salt thereof, so as to treat the TG2-associated disease or disorder in the subject, wherein the TG2-associated disease or disorder is fibrosis, Celiac disease, multiple sclerosis, Huntington's disease, Parkinson's disease, Alzheimer's disease, ovarian cancer, breast cancer, colon cancer, lung cancer, prostate cancer, pancreatic cancer, glioblastoma multiforme (GBM), or epidermal squamous cell carcinoma.

16. The method of claim 15, wherein tissue transglutaminase (TG2) is inhibited in the subject.

17. The method of claim 16, wherein GTPase activity of the TG2 is inhibited in the subject; GTP binding activity of the TG2 is inhibited in the subject; and/or transamidation activity of the TG2 is inhibited in the subject; optionally wherein said inhibiting comprises locking the TG2 in an open conformation.

18. The method of claim 15, wherein said compound or pharmaceutically acceptable salt thereof is administered orally, topically, or locally at the site of injury.

19. The method of claim 15, wherein said subject is a human.

* * * * *